(12) United States Patent
Bar-Shalom et al.

(10) Patent No.: US 8,383,154 B2
(45) Date of Patent: Feb. 26, 2013

(54) SWELLABLE DOSAGE FORM COMPRISING GELLAN GUM

(75) Inventors: Daniel Bar-Shalom, Kokkedal (DK); Lillian Slot, Virum (DK); Gina Fischer, Værløse (DK); Pernille Høyrup Hemmingsen, Bagsværd (DK)

(73) Assignee: Egalet A/S, Vaerlose (DK)

( * ) Notice: Subject to any disclaimer, the term of this patent is extended or adjusted under 35 U.S.C. 154(b) by 1259 days.

(21) Appl. No.: 11/596,123

(22) PCT Filed: May 11, 2005

(86) PCT No.: PCT/DK2005/000317
§ 371 (c)(1),
(2), (4) Date: Aug. 14, 2007

(87) PCT Pub. No.: WO2005/107713
PCT Pub. Date: Nov. 17, 2005

(65) Prior Publication Data
US 2008/0299199 A1 Dec. 4, 2008

(30) Foreign Application Priority Data
May 11, 2004 (DK) .................................. 2004 00755

(51) Int. Cl.
A61K 47/36 (2006.01)
A61K 47/38 (2006.01)
A61K 47/32 (2006.01)
A61K 47/02 (2006.01)
A61K 9/00 (2006.01)

(52) U.S. Cl. ........................................ 424/485; 426/573

(58) Field of Classification Search .................. 424/464, 424/473
See application file for complete search history.

(56) References Cited

U.S. PATENT DOCUMENTS

| | | | |
|---|---|---|---|
| 4,590,075 A | 5/1986 | Wei et al. | |
| 4,824,681 A | 4/1989 | Schobel et al. | |
| 4,882,169 A | 11/1989 | Ventouras | |
| 4,994,260 A | 2/1991 | Kallstrand et al. | |
| 5,126,151 A | 6/1992 | Bodor et al. | |
| 6,102,254 A | 8/2000 | Ross | |
| 6,395,298 B1 * | 5/2002 | Flanagan et al. | 424/479 |
| 6,488,962 B1 | 12/2002 | Berner et al. | |
| 6,709,678 B2 | 3/2004 | Gruber | |
| 2003/0232082 A1 * | 12/2003 | Li et al. | 424/473 |
| 2004/0247675 A1 | 12/2004 | Gruber et al. | |

FOREIGN PATENT DOCUMENTS

| | | |
|---|---|---|
| EP | 0272220 | 6/1993 |
| EP | 1 371 360 B1 | 12/2003 |
| JP | 11-187827 | 7/1999 |
| JP | 2004-97114 | 4/2004 |
| WO | WO 92/11084 | 7/1992 |
| WO | WO 97/38679 A2 | 10/1997 |
| WO | WO 98/23292 A1 | 6/1998 |
| WO | WO 99/62498 A1 | 12/1999 |
| WO | WO 01/76610 | 10/2001 |
| WO | WO 02/46571 A2 | 6/2002 |
| WO | WO 02/49571 A2 | 6/2002 |
| WO | WO 03/043638 A1 | 5/2003 |
| WO | WO 2004/096906 | 11/2004 |
| WO | WO 2004/096906 A1 | 11/2004 |
| WO | WO 2005/007074 | 1/2005 |
| WO | WO 2005/007074 A | 1/2005 |

OTHER PUBLICATIONS

JECFA, "Gellan gum". FNP 52 Addendum 4 (1996).*
JECFA, "Talc", FNP 52 Addendum 1 (1992).*
Alterna LLC, "ElixSure, Allergy Formula", description and label directions, online (Feb. 6, 2007).
Hägerström, H., "Polymer gels as pharmaceutical dosage forms", comprehensive summaries of Uppsala dissertations from the faculty of pharmacy, vol. 293 Uppsala (2003).
Lin, "Gellan Gum", U.S. Food and Drug Administration, www.inchem.org, online (Jan. 17, 2005).
Miyazaki, S., et al., "In situ-gelling gellan formulations as vehicles for oral drug delivery", J. Control Release, vol. 60, pp. 287-295 (1999).
Rowe, Raymond C. et al., "Handbook of Pharmaceutical Excipients", Pharmaceutical Press, Fourth Edition, 2003, pp. 257-258.
"Gellan Gum Wins IFT's Food Technology Industrial Achievement Award," *Food Technology*, Institute of Food Technologists, vol. 47, No. 9, Sep. 1, 1993, pp. 94-96.
Monsanto, "Kelcogel Gellan Gum," *Kelcogel*, 1998.
Bar-Shalom et al., "Opportunities and obstacles in Pediatric Oral Controlled Release Dosage Forms," *Parvulet Poster*, Online, Oct. 28, 2004.

* cited by examiner

*Primary Examiner* — Walter Webb
(74) *Attorney, Agent, or Firm* — Foley & Lardner LLP

(57) ABSTRACT

A novel dosage form. The dosage form is presented in particulate form and before oral ingestion the particulate material is subjected to an aqueous medium, whereby it is converted to a semi-solid form by swelling or gelling of one or more of the components, especially of a gellan gum, of the particulate matter. The invention also relates to a vehicle for oral administration of one or more active substances, the vehicle comprising a gellan gum arranged in a configuration allowing optimal water diffusion so that upon addition of a predetermined amount of an aqueous medium, without the necessity of applying shear forces or other mixing forces, within a time period of 5 minutes or less swells and/or gels and the texture of the swelled vehicle being similar to that of a soft pudding and having a viscosity of at least about 10,000 cps as measured by a Brookfield Viscometer with a #4 LV spindle at 6 rpm and at 20-25° C. In one embodiment of the invention, the particulate matter can be molded into a desired shape or pressed onto a dispensing unit such as a spoon.

106 Claims, 10 Drawing Sheets

SWELLABLE DOSAGE FORM COMPRISING GELLAN GUM

FIELD OF THE INVENTION

The present application relates to a novel dosage form. The dosage form is presented in particulate form and before oral ingestion the particulate material is subjected to an aqueous medium, whereby it is converted to a semi-solid form by swelling or gelling of one or more of the components, especially of a gellan gum, of the particulate matter. The invention also relates to a vehicle for oral administration of one or more active substances, the vehicle comprising a gellan gum arranged in a configuration allowing optimal water diffusion so that upon addition of a predetermined amount of an aqueous medium, without the necessity of applying shear forces or other mixing forces, within a time period of 5 minutes or less swells and/or gels and the texture of the swelled vehicle being similar to that of a soft pudding and having a viscosity of at least about 10,000 cps as measured by a Brookfield Viscometer with a #4 LV spindle at 6 rpm and at 20-25° C.

In one embodiment of the invention, the particulate matter can be moulded into a desired shape or pressed onto a dispensing unit such as a spoon.

BACKGROUND OF THE INVENTION

A recurring problem in the treatment of patients, in particular children and the elderly, is their inability or unwillingness to swallow solid oral dosage forms such as tablets or capsules. The problem is, however, not uncommon in healthy adults as well. This problem is not trivial, the inability or unwillingness of some people to take solid oral dosage forms can severely compromise the patient's compliance with a prescribed treatment protocol. Moreover, due to embarrassment, many patients are unwilling to tell their doctor of their problem so that the doctor can consider other drugs and/or alternate dosage forms. Such a lack of compliance can compromise treatment or cure.

If an orally administered drug has such a taste that is acceptable to the patient and the pharmacokinetic characteristics allow reasonable administration regimens, such as once or twice daily, the drug might be formulated in a syrup, elixir, suspension or other liquid dosage forms. Unfortunately, in many cases the native taste of the drug is unpleasant and not amenable to taste-masking by the addition of sweeteners of flavours. Also, many drugs have such pharmacokinetic parameters that demand administration at short intervals, disrupting sleep and other activities. The taste and/or pharmacokinetic deficiencies can be corrected by the use of various coating and/or matrices and/or by modifying the crystalline structure, et cetera. U.S. Pat. No. 6,589,955 illustrates such an approach. The resulting material after micro-encapsulation or crystallization or other strategies might be a monolithical unit, one unit containing the whole dose, or multi-particles, each particle containing a fraction of the total dosage. The monolithical units are often unacceptable to people having the swallowing problems described above. The multi-particles must be further processed into finished dosage forms such as tablets and capsules with the same limitation as the monolithical units or other forms specifically designed for children and/or adults unable to swallow oral solid dosage forms. Finally, some substances are administered in such high doses that the resulting tablets or capsules are either very large or that many tablets or capsules must be administered simultaneously, in either case, causing discomfort. The multi-particles may be presented as a powder. This powder might then be formulated into tablets or capsules meant to be swallowed whole. Those tablets and capsules as such are inappropriate for patients with swallowing difficulties. Patients (or they providers in the case of children) are often instructed to open the capsules (or crush the tablets) and to sprinkle the powder on syrup or pudding or applesauce or similar and then administered. This approach has limitations. The carrier (syrup, pudding, applesauce) is not a well defined entity and different carriers might interact differently with the multiparticles and/or drug and thereby compromise the treatment. Also, children might object to the grittiness in the material. Syrups do not necessarily resemble types of food or beverages that children are used to consume.

Alternatively the powder can be formulated into effervescent granules or tablets. These granules or tablets are intended to be dissolved in an aqueous liquid requiring the provision of a glass of liquid and a waiting period sufficient to allow the tablet to completely dissolve and the resulting volume might be considerable. Often, these dosage forms leave an objectionable deposit in the glass, which may represent a non-ingested part of the drug. Effervescent formulations are, in general more appropriate for adults although some commercial vitamin preparations for children use this approach.

Another category is the fast-melting tablets meant to be put on the tongue and disintegrate upon contact with saliva. The might be effervescent or non-effervescent. Yet another solution is to dispense the multi-particles in lozenges, chewable tablets and chewing gum.

One example of these approaches was described in Wehling et al., U.S. Pat. No. 5,178,878, which relates to certain effervescent dosage forms including microparticles. The effervescent dosage forms of Wehling et al. provide a significant advance over the art in that they provide an effervescent dosage form for direct oral administration. The dosage form is designed to disintegrate rapidly in the mouth releasing its microparticles as a slurry for ingestion. The dosage forms produced in accordance with Wehling et al. can be placed in the patient's mouth and the effervescence contained therein will be activated by contact with the patient's saliva. The tablet will then disintegrate in a number of seconds. However, the effervescence on the tongue may be unpleasant to some adults and to many children.

Kallstrand, et al., U.S. Pat. No. 4,994,260 relates to a pharmaceutical mixture. The mixture is used for the controlled release of a substance. According to Kallstrand et al., a liquid dosage form is produced using either a dry powder or microcapsules, which are suspended in a solution of a release-controlling substance, also referred to as a "sink". Alternatively, it is possible to encapsulate the release-controlling substance, together with a drug, within an encapsulating shell. The release-controlling substance may include, inter alia, carbohydrates and carbohydrate-related compounds, disaccharides, monosaccharides, glycerol, glycol, glycosides of monosaccharides and substances derived from ethyleneglycol.

Boder et al., U.S. Pat. No. 5,126,151 relates to an encapsulation mixture. Boder et al. refers to the construction of gums and candies in oral dosage forms. According to Boder et al., microcapsules are produced including a core material which can be selected from a wide variety of materials including sweeteners, medicaments, drugs, flavoring agents and the like. These materials can be used, either singularly or in combination, in either a single or multiple part delivery systems. That is, one or more of these materials may be present within one coating matrix or maybe separately coated by the matrix and employed alone or in combination in the final product. The resulting formulations are said to be able to provide a masking of unpleasant tasting drugs such as potassium chloride and the like, making consumption of the drug more appealing to the public. The dosage forms may be prepared in chewable tablet form.

Schobel et al., U.S. Pat. No. 4,824,681, and Wei et al., U.S. Pat. No. 4,590,075. Encapsulated sweeteners have also been used to provide an extended release of sweetening in, for example, chewing gum, see for example European patent application EPO 87-810747 to Schobel et al. and in bakery products such as disclosed in WO 91-US9434 filed Dec. 17, 1991 to Redding et al.

Further, in WO 01/76610 Simek et al describe a pharmaceutical composition containing calcium or mixture of calcium and vitamin D or mixture of calcium and magnesium and adjuvants, presented in the form of soluble powder, which by addition of liquids and mechanical mixing, forms a gelatinous suspension resembling a pudding.

U.S. Pat. No. 6,709,678 discloses an oral pharmaceutical composition to be dispersed in an aqueous carrier prior to administration comprising a multiplicity of particles consisting of a drug core individually coated with one or more layers with a hydratable polymer. The preferred hydratable polymers are preferably alginates, carboxymethylcellulose, hydroxypropylmethylcellulose and polyvinylpyrrolidone. The coating is applied by conventional coating methods with a powder mixture in a spheronizer or by spraying on a solution or suspension of the coating materials to the core. The aim of the hydrated formulation is to obtain a formulation in a single, slippery, non disintegrating mouldable coherent viscous plastic mass, which does not adhere to the mucosa.

WO2004/096906 A1 discloses a thickenable composition in water-containing liquid form which upon addition of further water increases in viscosity. The composition comprises different anionic polymers such as xanthan together with alginate, carboxymethyl cellulose, carrageenan, an acrylate polymer or pectin.

WO 2005/007074 A2 published on 27 Jan. 2005 discloses a gellan gum based oral controlled release dosage form for gastric retention. The formulation is swallowed in a non hydrated form such as a tablet and it is expected that the formulation when reaching the aqueous environment of the stomach would form a strong gel.

The present invention proposes an improvement over the art by providing a substantially water free dosage form, containing particulate material such as, e.g., particulate units, that is/are designed for the purpose of masking the taste of drug substance(s) and/or to provide controlled release of a drug substance or drug substances. In turn the particulate material may be coated and/or mixed with components that, upon exposure to water will swell into a soft pudding-like, mousse-like or soufflé-like semisolid mass that has a sensory-acceptable mouth-feel and taste as determined and judged by a professional taste panel. Further, the invention provides a vehicle to be combined prior to administration with particulate matter such as microencapsulated drugs.

SUMMARY OF THE INVENTION

In one aspect, the invention relates to a vehicle for oral administration of one or more active substances, the vehicle comprising a gellan gum arranged in a configuration allowing optimal water diffusion so that upon addition of a predetermined amount of an aqueous medium, without the necessity of applying shear forces or other mixing forces, within a time period of 5 minutes or less swells and/or gels and the texture of the swelled vehicle being similar to that of a soft pudding and having a viscosity of at least about 10,000 cps as measured by a Brookfield Viscometer with a #4 LV spindle at 6 rpm and at 20-25° C.

Dispersing, wetting/hydrating, dissolving gelling agents in water to form colloidal dispersions is a notoriously difficult procedure A discussion of the general properties of colloidal dispersions and their preparation can be found in: Remington; The Science and Practice of Pharmacy, 20$^{th}$ Edition, A. R. Gennaro et al editors, published in 2000 by Lippincott Williams and Wilkins (Chapter 21). Diverse techniques are involved, among them stirring, shaking, heating/cooling, slow and gradual addition of the gelling agent to the liquid, et cetera. This explains why the in the directions of use of the so called "Instant Puddings" or "Instant Creams" or "Instant Sauces" instructions such as "add the powder slowly to the boiling water" or "stir vigorously" or "let it stand for 30 minutes" are often found.

In another aspect, the invention relates to a pharmaceutical composition for oral administration comprising one or more active substances and a gellan gum arranged in a configuration allowing optimal water diffusion so that upon addition of a predetermined amount of an aqueous medium, without the necessity of applying shear forces or other mixing forces, within a time period of 5 minutes or less, the composition swells and/or gels and the texture of the swelled composition being similar to that of a soft pudding and having a viscosity of at least about 10,000 cps as measured by a Brookfield Viscometer with a #4 LV spindle at 6 rpm and at 20-25° C.

In a still further aspect, the invention relates to a dispensing unit comprising a pharmaceutical composition for oral administration comprising one or more active substances and a gellan gum arranged in a configuration allowing optimal water diffusion so that upon addition of a predetermined amount of an aqueous medium, without the necessity of applying shear forces or other mixing forces, within a time period of 5 minutes or less, the composition swells and/or gels and the texture of the swelled composition being similar to that of a soft pudding and having a viscosity of at least about 10,000 cps as measured by a Brookfield Viscometer with a #4 LV spindle at 6 rpm and at 20-25° C.

The pharmaceutical composition and the dispensing unit according to the invention are intended to be contacted with a small amount of water before administration and the water induces the swelling of the gellan gum, which makes the composition easy to ingest and at the same time provides an acceptable mouth-feel.

In the context of the present invention relatively small volumes are contemplated for the ready-to-administer unit (meaning after exposure to water), typically in the range of 1 to 100 mL, in particular 1 to 20 mL. Stirring/shaking or any type of mixing would be difficult and often result in loss of material thus compromising the accuracy of dosing. Therefore it is desirable to have a composition, which, upon exposure to water, will swell without shaking. It was found that if steps are taken to ensure rapid diffusion of water into the bulk, then the desired result is achieved. The steps include: (1) Addition of very soluble substances such as soluble sugars. (2) Using gelling agents presenting as fine powders (3) Granulating the ingredients with small amounts of binding solutions and (4) Packing the granulate (if desired) loosely.

Other possible techniques are forming the components, typically either the gelling agents and/or the sugars into threads which can be subsequently formed into non-woven tissues or forming the gelling agents into films where readily soluble substance are embedded to ensure channel of diffusion for the water. The last mentioned techniques might, in turn, be combined with granulated matter.

In accordance with the present invention, a pharmaceutical unit dosage form is provided that is dispensed as a solid, but which upon contact with a measured amount of water and without application of a shear force such as mixing quickly swells to provide a semi-solid mass that easily can be orally ingested by a patient, in particular patients with swallowing difficulties.

The unit dosage form includes a plurality of particles or a plurality of units. In the following the drug-containing particle or unit is commonly denoted "drug-containing micro-particle". The drug-containing micro-particle carries at least one therapeutically, prophylactically and/or diagnostically active substance and, optionally, components providing taste masking and/or controlled release functionality. Further, the dosage form contains one or more substances that are able to swell upon contact with water. Yet further the dosage form may contain taste modifiers such as sweeteners, flavors, preserving substances, texture modifiers, color modifiers and other additives such as binders. Importantly, the dosage form according to the invention has properties that are acceptable to the patient from a sensory aspect, i.e. when ingested, it does not have an unpleasant mouth-feel and/or a bad taste or odor. These properties are tested by a professional taste panel consisting of at least 6 persons that have been specifically selected due to their tasting ability as well as to children age 5-6 years to evaluate whether the children would have any objections to a repetitive placebo dosage according to the present invention.

The drug-containing micro-particles can be prepared following any of the conventional methods used e.g. in micro-encapsulation, in incorporation into matrices or by crystallization techniques.

In another aspect, the invention relates to a method for preparing a pharmaceutical composition according to the invention, the method comprising blending the dry components to a homogeneous mixture and optionally granulating the mixture with a binder.

DETAILED DESCRIPTION OF THE INVENTION

Vehicles and Compositions

As mentioned above, the invention relates to a vehicle for oral administration of one or more active substances, the vehicle comprising a gellan gum arranged in a configuration allowing optimal water diffusion so that upon addition of a predetermined amount of an aqueous medium, without the necessity of applying shear forces or other mixing forces, within a time period of 5 minutes or less swells and/or gels and the texture of the swelled vehicle being similar to that of a soft pudding and having a viscosity of at least about 10,000 cps as measured by a Brookfield Viscometer with a #4 LV spindle at 6 rpm and at 20-25° C. In a preferred aspect, the swelling and/or gelling agent is a gellan gum as mentioned above, but other swelling and/or gelling agents such as those mentioned herein may be employed as well provided that similar properties are obtained. The other swelling and/or gelling agents mentioned herein may be used together with gellan gum as well. Furthermore, it is important that the swelling takes place rapidly and without the necessity of stirring, shaking or using any other mechanical means. This characteristic of the vehicle (and the composition of the invention based on the vehicle) ensures that a pharmaceutical composition of the invention is easily transformed into a ready-to-use composition without any other means that addition of a small amount of water. Accordingly, the last-minute preparation in order to intake the composition is easy and convenient for the patient and do not require specific equipment.

As it will appear from the description herein, the ready-to-use composition is intended to adhere to the dispensing unit such as e.g. a spoon. Furthermore, it is advantageous that the ready-to-use composition does not fall off the dispensing unit and accordingly, the vehicle and/or the pharmaceutical composition must have a certain viscosity as mentioned above. In specific embodiments, a vehicle and/or composition of the invention has a viscosity in a range from about 10,000 to about 99,000 cps. The viscosity can be measured using a Brookfield Viscometer with a #4 LV spindle at 6 RPM and at 20-25 degrees C., or equivalent. Viscosity decreases slightly with increasing temperature.

The inventive formulations may also have a Brookfield viscosity within the range of about 10,000 cps to about 99,000 cps at room temperature. Below about 20,000 cps, formulations tend to spill but formulations less viscous might be appropriate in some instances, such as reclining patients. Formulations exhibit desirable spill-resistant properties at a viscosity greater than about 20,000 cps.

The ready-to-use compositions are non-Newtonian and time independent fluids. Non-Newtonian refers to a fluid whose behaviour departs from that of an ideal Newtonian fluid. These fluids have different viscosities at different shear rates and fall under two groups: time independent and time dependent. In contrast, for a Newtonian fluid the rate of shear in the fluid under isothermal conditions is proportional to the corresponding stress at the point under consideration. (McGraw-Hill Encyclopedia of Science & Technology, 6<th> edition, 1987, Volume 12, pages 57-60). Time independent fluids are those for which the rate of shear at any point in the fluid is some function of the shear stress at that point and depends on nothing else. These fluids have a constant viscosity value at a given shear rate. The viscosities do not change with time. These solutions may be pseudoplastic according to a rheogram. The viscosity of the gel decreases with increasing shear rate, and the behavior is fully reversible. Pseudoplastic fluids are those that show no yield value, but the ratio of shear stress to the rate of shear, which may be termed the apparent viscosity, falls progressively with shear rate. The decrease in viscosity with an increase in shear rate is also known as shear thinning. This phenomenon of shear thinning is characteristic of solutions of asymmetric particles or solution of polymers such as cellulose derivatives.

Moreover, in order to ensure that the ready-to-use composition does not fall off the dispensing unit, a drop down test has been developed. The vehicles and the compositions according to the invention meet the requirements given in the drop down test.

In order to obtain a suitable gelling and/or swelling a vehicle and/or a composition of the invention may further comprise a swelling and/or gelling agent selected from hydrocolloids and hydrogelling agents such as alginic acid, sodium alginate, potassium alginate, ammonium alginate, calcium alginate, propane-1,2-diol alginate, agar, carrageenan, processed eucheuma seaweed, locust bean gum, guar gum, tragacanth, acacia gum, xanthan gum, karaya gum, tara gum, konjac, pectins, cellulose derivatives such as: methyl cellulose, hydroxypropyl cellulose, hydroxypropyl methyl cellulose, ethyl methyl cellulose, carboxy methyl cellulose, sodium carboxy methyl cellulose, crosslinked sodium carboxy methyl cellulose, enzymatically hydrolysed carboxy methyl cellulose, gelatine, or mixtures thereof.

However, in a particularly preferred aspect of the invention, the vehicle or composition according to the present invention comprises a gellan gum arranged in a configuration allowing optimal water diffusion in order for the formulation to gel and swell within a short time and obtaining a texture like a soft pudding or mousse and which is easy to disperse.

The present invention also relates to a vehicle for oral administration of one or more active substances, the vehicle comprising a swelling and/or gelling agent selected from the group consisting of hydrocolloids, gums and cellulose derivatives, at least a part of the swelling and/or gelling agent arranged in a configuration allowing optimal water diffusion so that upon addition of a predetermined amount of an aqueous medium, without the necessity of applying shear forces or other mixing forces, within a time period of 5 minutes or less swells and/or gels and the texture of the swelled vehicle being similar to that of pudding and having a viscosity of at least about 10,000 cps as measured by a Brookfield Viscometer with a #4 LV spindle at 6 rpm and at 20-25° C.

In a further aspect, the invention relates to a solid dosage form comprising an active substance and a vehicle according to the invention. The solid dosage form may be in the form of a unit dosage form or a dosage kit comprising a dispensing unit incorporating the solid dosage form. Typically the dispensing unit is a spoon and the solid dosage form may be glued to the concave part of the spoon.

Hydrogels—Gellan Gum

In order to swell the gel needs to absorb water and this is associated with dimensional changes and it is necessary for the water molecules to gain access to the inner structure of the materials. The small size of the water molecule and the fact that the material is substantially amorphous in general offer good possibilities of hydrogen bonding, enabling the water molecules to penetrate, and thus swell. The primary mechanism of absorption of water and desorption of drugs from hydrogels is diffusion, occurring through the space available between macromolecular chains. This space is often regarded as the "pore". Depending on the size of these pores, hydrogels can be conveniently classified as (1) macro-porous; (2) micro-porous; and (3), non-porous. The meaning of the term "pore" can sometimes be confusing, as it is only a reflection of the radius of gyration of a probe molecule, which like water may be sorbed in the system. The smallest pore (smaller in 4 Å in radius) represents areas between the polymer chains where mainly bound, or inaccessible water is being held. Other areas in the gels form a polymer network (e.g. amorphous), which holds water in pores (about 10 Å in radius) within the gel structure. Bound water directly adsorbed to the polar groups and free water fills all available space created by swelling within the gel. Larger pores (larger than about 10-15 Å in radius) can be cracks, voids etc, and formed due to various treatments. The larger pores contain mainly free water present in smaller or larger quantities depending on the size of the pore.

Hydration is a general term concerning the amount of bound water but it is poorly defined. Even what is meant by 'bound' is very difficult to explain (or investigate) exactly and has been defined as 'non-bulk' water. Using a simplistic approach to polysaccharide hydration, water can be divided into 'bound water', subcategorized as being capable of freezing or not, and 'unbound water', subcategorized as being trapped or not. 'Unbound' water freezes at the same temperature as normal water (<0° C. dependent on cooling rate).

In practical experience, the effects of water on polysaccharide and polysaccharide on water are complex and become even more complex in the presence of other materials, such as salts. Water competes for hydrogen bonding sites with intra-molecular and intermolecular hydrogen bonding, certainly will determine the carbohydrate's flexibility and may determine the carbohydrate's preferred conformation(s). There is a high entropic cost (up to about 20.8 kJ mol-1 at 25° C. for a totally 'frozen' molecule) when water is bound and this must be reclaimed, for example, by the formation of stronger or extra hydrogen bonds. An additional approach to explain the adsorption of water in hydrophilic polymers in general is the theory of clusters. In this approach, the polymers are said to provide adsorption sites rather than an adsorption surface. Certain adsorptions sites can adsorb one, two and in some cases more water molecules before other sites, less energetically attractive to new water molecules, adsorb their first water molecule. As the water content increases, the tendency for water molecules to cluster also increases, and thus grows in size.

When the number of water molecules in a cluster reaches about four, the interactive forces between the adsorption site and the water molecules are no longer large enough to hold the cluster, and whole clusters may move from one site to another. In an ion free aqueous medium, Gellan gum forms double helices at room temperature. The helices are only weakly associated with each other (by van der walls attraction).

Dynamics of Swelling:

The swelling kinetics of hydrogels can be classified as diffusion controlled (Fickian) and relaxation-controlled (non-Fickian) swelling.

Mechanical Properties:

The mechanical properties of the hydrogels are relevant for the pharmaceutical application; in the present case where it is desirable that the gel formed will not slip the delivery device before applied.

Changing the degree of cross-linking by adding e.g. salt will until a saturation point result in a stronger gel. Hence, there is an optimum degree of cross-linking to achieve a relatively strong and yet elastic hydro gel, e.g. at high ionic content the polysaccharides will form insoluble aggregates which can interconnect and form a weakened gel network.

The plurality of drug-containing micro-particles described above may be mixed with one or more pharmaceutically acceptable excipients or additives. A measured amount of such a mixture in powder form is designed to interact with a specified amount of water to form a semisolid mass meant to resemble in appearance, mouthfeel, taste, texture and color, a form of food of daily occurrence, such as pudding, applesauce, custard, puree, etc. The interaction should lead to the desired semisolid mass in as short a period as possible and without the necessity to apply any external force like e.g. a shear force like mixing. In the case where the active substance is in the form of microencapsule, i.e. the active substance is incorporated in small particles that e.g. is coated by a controlled release or taste-masking coating, a long period would result in release of the active substances trapped in the particles, thereby compromising the controlled release of the drug and/or negatively affect the taste of the composition and/or compromise the stability of the active substances. The desirable range for the swelling is less than 5 minutes, preferably less than 3 minutes and most preferred, less than a minute. In particular for children, a period less than 30 seconds is further preferred as the administering adult has to control the child at the same time. Suitable excipients are any gelling agent or agents capable of forming a semisolid mass in a short time when in contact with water in a temperature range from cold (ice water) to tepid (50 degrees celcius). Typically, the gelling agent or agents or mixtures of gelling agents are selected from the group consisting hydrocolloids such as of gellan (native, or in high acyl form or low acyl form, agar, alginate, modified alginates such as propylene glycol alginate, pectin, iota-carrageenan, kappa-carrageenan and furcelleran, agar, processed eucheuma seaweed, locust bean gum, guar gum, tragacanth, acacia gum, xanthan gum, karaya gum, tara gum, konjac, pectins, cellulose derivatives such as: methyl cellulose, hydroxypropyl cellulose, Hydroxypropyl methyl cellulose, Ethyl methyl cellulose, Carboxy methyl cellulose, Sodium carboxy methyl cellulose, Crosslinked sodium carboxy methyl cellulose, Enzymatically hydrolysed carboxy methyl cellulose, native or modified starches, gelling proteins including whey proteins and caseinates, gelatine etc.

A preferred gelling agent is Gellan having the following chemical structure, show in low acyl form:

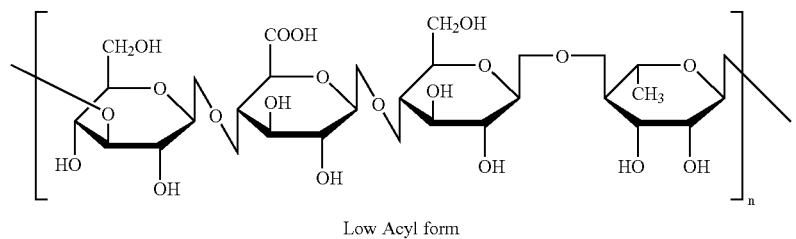

Low Acyl form

Comparison of Physical Properties of High Acyl and Low Acyl Gellan Gum

|  | Kelcogel LT100 (High Acyl) | Kelcogel F (Low acyl) |
| --- | --- | --- |
| Molecular Weight | 1-2 × 106 Daltons | 2-3 × 105 Daltons |
| Solubility | Hot water | Hot or cold water |
| Set temperature | 70°-80° C. | 30°-50° |
| Thermo reversibility | Thermo-reversible | Heat stable |

The molecular structure of gellan gum is straight chain based on repeating glucose, rhamose and glucuronic acid units. In its native or high acyl form, two acyl substituents—acetate and glycerate—are present. Both substituents are located on the same glucose residue, and on average, there is one glycerate per repeat and one acetate per every two repeats. In low acyl gellan gum, the acyl groups are removed completely. The acyl groups have a profound influence on gel characteristics. The high acyl form produces soft, elastic, non-brittle gels, whereas the low acyl form produces firm, non-elastics, and brittle gels. The acylated form is shown below.

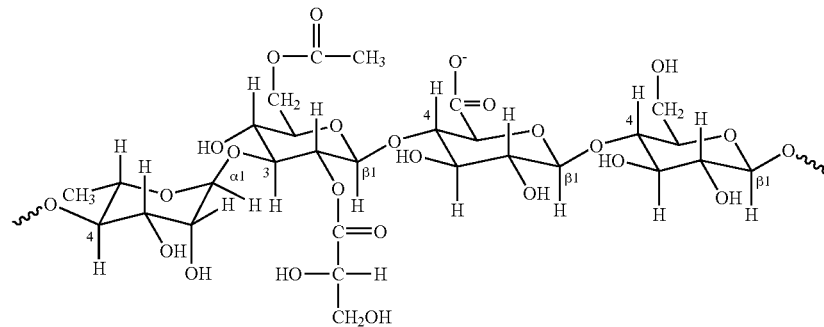

Gellan gum forms a coaxial triangular 3-fold double helix (pitch 56.4 Å) from two left-handed chains coiled around each other with the acetate residues on the periphery and glyceryl groups stabilizing the interchain associations. Hydrogen-bonds are formed between the hydroxy methyl of 4-linked glucosyl units of one chain and the carboxylate group of other. There are ion-binding sites by both carboxylate oxygen atoms and a hydroxyl group in one chain and two hydroxyl groups in the other plus one strongly bound water molecule. Pairs of helices may form antiparallel junction zones with Ca2+.

Functionality:

The functionality depends on the degree of acylation and the ions present. If low acylated, gellan forms soft, elastic, transparent and flexible gels but once de-acylated it forms hard, non-elastic brittle gels. An important feature is the irrevasible gelling properties where gellan gum may form an irrevasible film after dehydration, which will prevent gelling on rehydration. A gel sol transition occurs at about 50° C. dependent on concentration. Thermoreversible gels form on cooling in the presence of cations even at low (0.1% w/w) to very low (0.005% w/w) concentrations.

Gellan is unique in that it forms gels with all ions, including hydrogen. Gellan is compatible with a number of other gums (xanthan, locust bean), starches and gelatin to manipulate the type of gel, elasticity and stability. Gellan may be combined in mixtures producing synergistic properties which mixtures may also include natural seaweeds, natural seed gums, natural plant exudates, natural fruit extracts, bio-synthetic gums, bio-synthetic processed starch or cellulosic materials. More specifically, the mixture may include alginates, agar gum, guar gum, locust bean gum (carob), carrageenan, tara gum, gum arabic, ghatti gum, Khaya grandifolia gum, tragacanth gum, karaya gum, pectin, arabian (araban), xanthan, starch, konjak mannan, galactomannan, funoran.

Another preferred swelling and swelling improving agent is konjak. Konjak contains 50%-60% glucomannan, 20-30% starch, 2-5% fiber, 5-10% crude protein, 3-5% soluble sugars (monosaccharide and oligosaccharide) and 3-5% ash (minerals). Chemical Structure of Konjac Glucomannan (KGM) is shown below. The molecular weight of KGM varied from 1,000,000 to 2,000,000 daltons according to konjac species or variety, processing method and storage time of the raw material.

In a preferred embodiment, the gellan gum has a mean particle size within 25 mesh to 300 mesh in order to allow a suitable distribution of water into the vehicle.

Furthermore, in a specific embodiment, the gellan gum is acylated within a degree of 0 to 4 per every two repeats of the glucose-rhamnose-glucose-glucuronic acid unit of the polymer. The vehicle or composition may contain a mixture of gellan gums having different degrees of acylation and/or different mean particle sizes.

In a specific embodiment, the gellan gum has a degree of acylation of one glycerate per repeat and one acetate per every two repeats.

As mentioned above, the presence of gellan gum in a vehicle or a composition according to the invention may lead to a porous hydrogel when contacted with water such as, e.g., a micro-porous hydrogel having a pore size of at the most 4 Å or a macro-porous hydrogel having a pore size of from about 4 to about 15 Å.

which may be formed by addition or by condensation polymerization, the components of which may comprise hydrophilic and hydrophobic monomers. Preferred polymers for use at the water-swellable hydrophilic polymers include PEO, PEG, PVP, HPMC and polyacrylic acid.

By "osmotically effective solutes" is meant any water-soluble compound that is commonly referred to in the pharmaceutical arts as an "osmogen" or an "osmagent". Typically classes of suitable osmogens are water-soluble organic acids, salts and sugars that are capable of imbibing water to thereby affect an osmotic pressure gradient across the barrier of the surrounding matrix. Typical useful osmogens include magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, inulin, instant sugar, citric acid, succinic acid, tartaric acid, and mixtures thereof. Particularly preferred osmogens are glucose, lactose, sucrose, mannitol, xylitol and sodium chloride.

Electrolytes

The electrolyte's greater hydrophilicity than the other formulation components allows it to hydrate preferentially in Konjak:

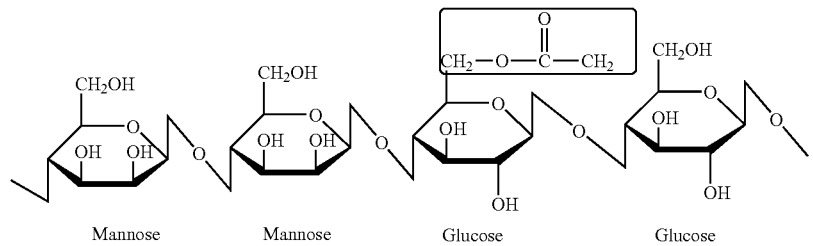

Some of the factors there can effect the swelling include pH, ionic strengths, and temperature. The behaviours of the different hydro gels as drug carrier, is well known. The behaviour of e.g. Gellan gum is quite different from that of PVP and PEO, respectively. In fact, although the gel Gellan Gum with cations shows a very well ordered and regular structure both in the solid state and in solution, when it is tested as a matrix it swells up and it is rapidly dispersed, leading to a quite fast release of the API (active substance).

As mentioned above, a vehicle or a composition according to the invention may further comprise an agent that improves swelling of the gellan gum. Such an agent may be a hydrophilic agent selected from the group consisting of electrolytes, organic acids and osmotic agents, and mixtures thereof.

Osmotic Agents

By the term "osmotic agent" is meant any agent which creates a driving force for transport of water or media (aq.) from the environment of use into the matrix. Exemplary osmotic agents are water swell able or water soluble. The vehicle or composition according to the invention may include water-swell able hydrophilic polymers, both ionic and non-ionic, often refers to as "osmopolymers" and hydro gels. Exemplary materials include hydrophilic vinyl and acryl polymers, poly saccharides, PEO, PEG, PPG, poly(2-hydroxyethyl methacrylate), poly(acrylic)acid, poly(methacrylic)acid, PVP, PVA, PVA/PVP copolymers, HEC, HPC, HPMC, CMC, CEC, sodium alginate, polycarbophil, gelatine and sodium starch glycolate. Other materials include hydrogels comprising interpenetrating networks of polymers, comparison to the surrounding polymers and the drug molecules. This peripheral matrix-hardening creates a controllable micro-environment within the hydrated layer, and make the formulation robust again variable ion strengths from added water to the matrix.

The use of e.g. alkalizing agents to preserve internal dosage form pH though the acid regions of the upper gastrointestinal tract is well established.

One advantage of maintaining a constant internal pH is that a very soluble drug in 0.1 M HCl may be made less soluble if the environmental pH is above the pKa-value of the drugs. Through the application of colloidal chemistry principles, it is possible to provide pH-control via a formulation component that is also active as a release controlling excipient within a hydrophilic matrix.

A vehicle or composition according to the invention may also comprise a pH-adjusting agent selected from the group consisting of any material which is suitable to adjust the pH of an aqueous gel such as, e.g., sodium bicarbonate, sodium phosphate, sodium hydroxide, ammonium hydroxide, sodium stannate, triethanolamine, citric acid, hydrochloric acid, sodium citrate, and combinations thereof. Generally, if present, the pH adjusting agent is present in an amount so as to adjust the pH of the gel formed upon addition of an aqueous medium to about 4.5 to about 11, preferably from about 5 to about 9, and more preferably from about 5 to about 8. A suitable amount is normally in an amount of from about 0.01% to about 15% w/w such as, e.g., from about 0.05% to about 5% w/w.

Upon ingestion, gastric fluid enter into the dosage form, causing the composition to hydrate and activates the pH and release-controlling characteristics of the excipients.

A suitable electrolyte for use according to the invention is a ionizable substance that is selected from the group consisting of monovalent, divalent, or multivalent ionizable salts. More specifically, the salt is selected from inorganic salts, including various alkali metal and/or alkaline earth metal sulfates, chlorides, borates, bromides, etc., and ionizable alkaline earth organic salts such as citrates, acetates, lactates, etc.

In specific embodiments, the salt is selected from calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, alkali metal chlorides, sodium fluoride, organic acids such s citric, succinic, fumaric, malic, maleic, glutaric, lactic and the like; alkali metal sulfates such as sodium sulfate; dihydrogen sodium phosphate, monohydrogen sodium phosphate, disodium hydrogen phosphate, and mixtures thereof, and multivalent metal cations. Notably, the salt is calcium sulfate or sodium chloride.

Organic Acids

The present formulations may also contain organic acids to delay dissolution rate in the acid media and/or to increase the dissolution rate in buffer at pH 6.8 or to ensure drug stability with time and provide a substantially pH independent dissolution profile.

The organic acids are chosen to cover a solubility and pKa-values range, in order to cover a range of pH and to help controlling the release mechanism. The aim is to obtain the same release time in both buffer 6.8 and in 0.1M HCl. Pharmaceutically acceptable organic acids are e.g. Benzoic acid, Succinic acid, Citric acid and Adipic acid but can include other pharmaceutically approved organic acids.

Ionic Strengths

An increase in electrostatic repulsion, by adding e.g. monovalent or/and divalent metal ions (natively present or introduced in the formulation) also promotes a swelling until a saturation point. The driving force necessary to expand the material during swelling is the electrostatic repulsion between different ionic groups with the same charges. The nature of the counter ions is thus of extremely importance for the degree of swelling of such charged gel-like systems. Changing the ionic content in the formulation will affect the water uptake. The nature of the ions (ion pair) has a profound effect on the characteristics of the water adsorption due to the different ability of the ion pair to dissociate.

The ion pairs will compete with the hydro gel about the water molecules, and can thereby increase the hydration and decrease the solubility of the hydro gel, respectively, which can stabilise the gel formation.

Physical and Chemical Properties of Hydrogels

The cross linking ratio is one of the most important factors that effects the swelling of hydro gels. It is defined as the ratio of moles of cross linking agent to the moles of polymer repeating units. The higher the cross linking ratio, the more cross linking agent is incorporated in the hydro gel structure. Highly cross linked hydro gels have a tighter structure, and will swell less compared to the same hydro gel with lower cross linking ratios. Cross linking hinders the mobility of the polymer chains, hence lowering the swelling ratio. The chemical structure of the polymer may also affect the swelling ratio of the hydro gels. Hydro gel contains hydrophilic groups swell to a higher degree compare to those containing hydrophobic groups. Hydrophobic groups collapse in the presence of water, thus minimizing their exposed to the water molecule.

pH-Sensitive Hydro Gels

The hydrogels which exhibiting pH dependent swelling behaviour will in aqueous media of appropriate pH and ionic strengths be ionized. As a result in of the electrostatic repulsions, the uptake of water in the network is increased. Ionic hydrogels are swollen polymer networks containing pendant groups, such as carboxylic acid, which show sudden or gradual changes in their dynamic and equilibrium behaviour as a result of changing the external pH. In these gels, ionization occurs when the ph of the environment is above the pKa of the ionisable group. As degree of ionization increases the number of fixed charges increases resulting in increased electrostatic repulsions between the chains. This in turn, results in an increased hydrophilicity of the network, and greater swelling ratio. The swelling of polyelectrolyte gels is significantly affected by the ionic strengths of the swelling agent. As the ionic strengths of the swelling agent increases, the concentration of ions within the gel must increase in order to satisfy the Donnan equilibrium.

A vehicle or composition according to the invention may also comprise one or more pharmaceutically acceptable excipients or additive.

Excipients

A wetting agent may be used such as one or more selected from the group consisting of pharmaceutically acceptable anionic surfactants, cationic surfactants, amphoteric (amphipathic/amphophilic) surfactants, and non-ionic surfactants including poloxamer, PEG, and PEO; alkane metal sulfates, wherein the alkyl group is from 1 to 14 carbon atoms, such as sodium methyl sulfate, sodium lauryl sulfate and the like as well as dioctyl sodium sulfosuccinate.

In a specific embodiment of the invention, a vehicle or composition further comprises glycerol, cf. the examples herein.

Suitable excipients and/or additives may be selected from the group consisting of surfactants, coloring agents, sweetening agents, taste-masking agents, antioxidants, polysaccharides, sugars, wetting agents, UV-absorbers, suspending agents, stabilizers, solubilizers, preservatives, processing aids, pH controlling agents, plasticizers, odor masking agents, nutrients, flavouring agents, flavour masking agents, emulsifiers, thickening agents, dispersing agents, crystal grow inhibitors, crystallization promoters, chelating agents, buffers, bases, and antimicrobials, and mixtures thereof.

In order to ensure an effective interaction of the water with the gelling agent or agents, the addition of a cation and/or sequestering agent to the mixture might be desirable and is generally depending on the swelling agent or mixtures hereof. Examples of suitable cations and sequestering agents which may be added to cause this gelling agent to gel are well known to persons skilled in the art and include Na+, $Ca^{2+}$, K+ and H+, sodium hexametaphosphate, sodium tripolyphosphate, EDTA, citric acid, sodium citrate and other citric acid salts, phosphoric acid, dicalcium phosphate and tetrasodium pyrophosphate.

An excipient for use in a dosage form according to the present invention may also include one or more other components generally known for use in food products, such as flavourings, colourings, sugar and/or other sweeteners, preservatives, buffering agents, texturing agents, fats, colloids, suspended solids, etc, to give the a desired texture and/or appearance. The amounts of such components are not critical to the invention and may be adjusted according to taste and according to the flavour/texture characteristics desired of the mixture of the invention. The pH of the mixture might be adjusted to the requirements of the active substance(s).

Excipients Used to Change the Hydration and Diffusion of Water into the Matrix System While the slow swelling property is the one that also made hydro gels useful in controlled drug delivery, many applications required fast swelling (i.e. swelling in a matter of minutes or seconds rather than hours) of dried hydro gels.

Being a water soluble polysaccharide e.g. Gellan gum can be difficult to disperse in water due to the formation of a film layer around each Gellan gum particle. This leads to the formation of large agglomerates (lumps), which, due to the protective film layer, are very difficult for the water molecules to penetrate.

The less soluble the Gellan gum is the easier the dispersion, other factors which decrease the solubility of Gelan gum will improve the dispersibility.

Different formulation initiative, by e.g. incorporation of hydrophilic excipients, can change the hydration, and swelling rate:

Fast swelling is usually done by making very small particles of dried hydro gels. The extremely short diffusion path length of micro particles makes it possible to complete swelling in a matter of seconds or minutes.

By creating pores that are interconnected to each other throughout the hydro gel matrix. The interconnected pores allow for fast absorption of water by capillary force. A simple method of making porous hydro gel includes, produce gas bubbles by adding sodium bicarbonate to generate carbon dioxide bubbles, and generation of gas bubbles makes the foam rise.

Another approach is to separate the hydro gel particles from each other before contact with water. If the hydro gel particles are right next to each other then they all try to swell at the same time, and weld themselves together into one large, slow to hydrate lump. If the pectin particles are all slightly separated from each other when they contact the water, then they all have enough room to go through their initial expansion. To achieve a fast hydration, and thereby swelling for the matrix system it is preferable to added hydrophilic or/and ion pair formation excipients.

Hydrophilic Excipients:

Known excipients can be blended with the molecular or dispersed dosage form to provide a controllable water diffusion/drug release mechanism.

Vehicle Form

A vehicle according to the invention may have any suitable form such as, e.g., in the form of a powder blend, in the form of granules, beads, oblates or pellets, or in the form of a granulate. Any additive or excipient, if present, may be incorporated e.g. in the granules etc, or it may be loosely added e.g. after formation of a granulate. As mentioned hereinbefore, the vehicle may be admixed with one or more active substances, i.e. the active substance may be incorporated in the granules etc., or it may be added after formation e.g. of a granulate. The active substance may also be present in a coated and/or microencapsulated form or embedded in a matrix, or in a form that allows for controlled release of the active substance.

Compositions

As mentioned above, the present invention also relates to a pharmaceutical composition for oral administration comprising one or more active substances and a gellan gum arranged in a configuration allowing optimal water diffusion so that upon addition of a predetermined amount of an aqueous medium, without the necessity of applying shear forces or other mixing forces, within a time period of 5 minutes or less, the composition swells and/or gels and the texture of the swelled composition being similar to that of a soft pudding and having a viscosity of at least about 10,000 cps as measured by a Brookfield Viscometer with a #4 LV spindle at 6 rpm and at 20-25° C.

All the details and particulars mentioned hereinbefore relating to other aspects of the invention apply mutatis mutandis to this aspect.

The pharmaceutical composition or the dosage form of the invention includes a plurality of drug-containing micro-particles. Each micro-particle carries at least one active substance and, optionally, components providing taste masking and/or controlled release functionality. The micro-particles can be produced using know micro-encapsulation or by integration into a matrix or by crystallization. The particles may be further fragmented to reduce the particle size. The preferred embodiments are those where the particles are small so as to be imperceptible or nearly imperceptible to the patient, visually and/or tactilely, in particular on the tongue. The preferred embodiments are those where the particle size is less than 500 micrometers and best less than 200 micrometers. However, if the retention in the mouth of even a few particles after a few minutes is not desired (because, for example, the taste being masked leaks), the particles should not be smaller than 100 micrometers so they are not retained in crevices in the pouth or between papillae on the tongue, unless the cohesiveness of the semisolid vehicle ensures that all particles are swallowed with the vehicle.

In another aspect of this invention, the active substances do not require controlled release or taste masking but, because of stability problems, in particular hydrolysis they can not be formulated in water containing dosage forms; also the approach may be useful if very large doses are to be administered. Accordingly, in one aspect of the invention a dosage form is provided having a water content of at the most about 5% w/w such as, e.g., at the most about 4% w/w, at the most about 3% w/w, at the most about 2% w/w, at the most about 1% w/w or at the most about 0.5% w/w.

The dosage form may be dispensed as a granulate in bulk or further processed into discrete units. The discrete units may be capsules or cachets or sachets filled with a measured amount of granulate meant to be opened and the contents poured onto a measured amount of water. However, the capsules or cachets or sachets may be made from fast dissolving materials such as water soluble polymer films, woven or non-woven fabrics made of water soluble materials such as candy floss. Further, the capsules or cachets or sachets might be made of gelling polymers such as those described for the mixture.

The discrete units may also be tablets meant to be put into a measured amount of water. In producing the tables, attention must be paid to the fact that, the more the material is compacted, the more difficult the penetration of water into the unit will be. Therefore, the production method for the tablets must be adapted. Production methods might include low-pressure compression, extruding, molding and calendaring.

In a specific embodiment of interest, the discrete units may be in the form of a disposable spoon where the granulated is fastened, typically by using a hydrocolloid solution as a binder and drying. Such a unit is illustrated in FIG. 1. To this end, it is extremely important that the dosage form of the drug-containing micro-particles is designed so that a suitable texture of the dosage form is obtained after addition of a predetermined amount of an aqueous medium such as water without the necessity of employing any shear force such as e.g. mechanical mixing or stirring.

The dosage form might also be formed into a tape or laminate, with or without the help of water soluble polymer films, woven or non-woven fabrics made of water soluble materials such as candy floss. This laminate can then be cut into discrete portions or dispensed as such, so the user can cut it to the required dose/size.

In some cases, where the purity of the water is an important factor, such as when presence or absence of given ions might interfere with the gelling process, it might be desirable to dispense the water alongside the granulate. In the case of a satchet it might be dispensed as a two compartment plastic bag, one compartment containing the granulate, the other the water. In the case of the spoon, a reservoir might be built-into the handle of the spoon.

Conventional coating procedures and equipment may then be used to coat or embed the drug-containing micro-particles, i.e., the drug-containing beads or particles. For example, a delayed release coating composition may be applied using a coating pan, an airless spray technique, fluidized bed coating equipment, or the like. For detailed information concerning materials, equipment and processes for preparing beads, drug particles, and delayed release dosage forms, reference may be made to Pharmaceutical Dosage Forms: Tablets, eds. Lieberman et al. (New York: Marcel Dekker, Inc., 1989), and to Ansel et al., Pharmaceutical Dosage Forms and Drug Delivery Systems, 6$^{th}$ Ed. (Media, Pa.: Williams & Wilkins, 1995).

Drug Delivery (Release) from the Composition
Swelling-Controlled System:

Formulations consisting of hydrophilic matrixes, and from which the drug release is controlled by the inward flux of solvent molecules and consequent swelling of the polymer matrix, are often referred to as a swelling-controlled systems. In these systems, the drug are initially dissolved or dispersed in the glassy polymers. Upon contact with fluids (pre-hydration with water or/and biological fluids), the polymer matrix begins to swell and two distinct phases can be observed in the polymer: the inner glassy phase and the swollen rubbery phase. The drug molecule are able to diffuse out of the out of the rubbery phase of the polymer. Clearly, the drug release is controlled by the velocity and position of the glass-rubbery interface. A very important phenomenon of macromolecular relaxation takes place at the glass-rubbery interface, and significant affects the drug release.

This is due to the fact that the matrix is exposed to continuous changes in its structure and thickness. The gel layer is a hydrophilic barrier that can controls water penetration and drug diffusion. It begins when the polymer becomes hydrated and swells. Here, the polymer chains are strongly entangled in a network, and the gel layer is highly resistant. However, moving away from this swelling position, the gel layer becomes progressively more hydrated and, when sufficient water has accumulated, the chains disentangle and the polymer dissolves.

In matrix systems, which are also diffusion-controlled, the drug can be either dissolved or dispersed in throughout the network of the hydro gel.

There are different approaches to controlling the release rate from the matrix system. Some of the major formulation parameters, which can be varied to adjust the resulting release patterns to designing a new oral controlled release system can include:
The initial drug loading
The API solubility
Type of matrix forming polymers
Type and load of hydrophilic/hydrophobic excipients Release Mechanisms for API Incorporated in a Primary Based Hydro Gels:

In development of an a delivery system, three significant phenomena (simplified) must be taken into account simultaneously,
Diffusion of water, drug, excipients and disentangled polymer chains,
Polymer hydration and swelling,
Drug, excipient and polymer dissolution.

Furthermore, in a formulation containing an API, polymer(s), and excipients, three different kinds of interaction may affect the release of the API: (i) the API may interact with the polymer, (ii) the drug may interact with the excipients, and (iii) the excipients may interact with the polymer(s) matrix. The rate of API release can be successfully controlled by controlling these interactions.

The dissolution rate is often influenced by a) composition and level of drugs and other additives within the matrix, and b) composition and ionic strengths of electrolytes in the dissolution medium.

It is possible to control or/and change the release rate of the drug from the polymer by varying e.g. the physical-chemical properties of the active drug, excipients or/and the polymer system. Extremely simplified, by adding more soluble excipients compared to the API solubility, will to some extent increase the release rate of the matrix system, and opposite for more hydrophobic excipients the release rate will be slowed down. When e.g. adding very soluble excipients, the network becomes more and more porous upon drug depletion. Consequently, the free volume increases, and thus polymer disentanglement increases giving rise to higher diffusion constants and thus faster dissolution.

The physical-chemical properties of the matrix (composition) components will alter the intermolecular forces, free volume, glass transition temperature, and consequently, can alter the transport mechanisms.

In general, solubility of drug molecule itself crucially governs the rate and extent of diffusion release in both the matrix system, and the delivery sites. For diffusion to occur, the first step is wetting of the drug by water, followed by its dissolution to enable the drug molecule to be available in molecular. Hence, the net release rate observed is a cumulative effect of drug solubility (influence by its structure, molecular weight, pKa), polymer property (hydrophilicity/lipophilicity, molecular weight, tortuosity), excipients (structure, molecular weight, solubility, pKa) and the relative ratio of drug/polymer, and excipient/polymer in the unit.

Initial Load/Dissolution Profiles

Various factors contribute to the overall control of drug release, such as the solubility of the drug within the bulk fluid, drug load, the size of the drug molecule, and it's mobility within the swollen polymeric network.

In the case of poorly water-soluble drugs (solubility <1 g drug/100 mL solution) or high initial loadings of moderately water soluble drugs (1 g drug/10 mL solution), dissolved and non-dissolved drug coexist within the composition. If the total amount of drug exceeds the amount, which is soluble under the actual conditions, it exceeds the amount soluble under the actual conditions, the excess is considered to be non-dissolved and thus not available for diffusion.

With decreasing drug solubility the concentration difference during drug release (matrix position vs. bulk fluid) decreases, and thus the driving force for drug diffusion out of the matrix decreases. Under theses conditions a decrease of the porosity of the matrix upon drug depletion (due to an increase initial drug loading) has probably a more pronounced effect on the resulting absolute drug release rate than in the case of e.g. freely soluble drugs, and thus higher diffusion driving forces. Consequently, the critical initial drug loading increases with decreasing drug solubility.

The effect of the initial drug loading of the tablet on the resulting release kinetic is more complex in the case of poorly soluble drugs compared to freely water soluble drugs.

With decreasing drug solubility the concentration difference during drug release (matrix position vs. bulk fluid) decreases, and thus the driving force for drug diffusion out of the matrix decreases. Under these conditions, decrease of the porosity of the matrix upon depletion (due to an increased initial drug loading) has probably a more pronounced effect on the resulting drug release rate than in the case of higher drug solubility. Consequently, the critical initial drug loading (above which the relative release rate increases) increases with decreasing drug solubility. These phenomena are not straightforward and have to be taken into account when designing the new formulation.

With respect to the blending of the vehicle according to the present invention it should be noticed whether any of the desires excipients or active drugs have a solubility considerable below that of gellan gum as the substance may decrease the hydration of the gellan gum. In such cases the substance should be added to a pre mixture of other ingredients, which pre mixture or blend preferable is granulated before adding the substance with lower solubility. In cases where one of the ingredients is capable of solubilizing the gellan gum, the same procedure is to be used in order to prevent any solubilizing of the gellan gum which will otherwise result in decreased gelling capacity.

Particle and Granular Sizes:

Although it is not required, it is preferred that the API, gellan gum, hydro gel(s), and excipients is in particulate form. The particles should, as a general rule, be of a size, such that, the matrix can hydrate sufficiently, and equally throughout the matrix. To prevent segregation, and consequently inhomogen products it would be preferable to formulate with uniform particle sizes, with exception of PVP, wherein it can also be an advantage to have smaller particles. A suitable granular size should be between 350-500 µm. Furthermore it is an advantage to seal the material after fastened the discrete units on a delivering device. The fastening is easily done by spraying the device with a glue to adhere the discrete unit to the device. Such glue may be produced by mixing a volatile liquid with a binder until a clear solution is achieved, and the formulation is transferred to e.g. by use of an aerosol can to the device, such as a spoon the volatile liquid is evaporated from the spoon in an oven, and thus the device surface is sticky.

The layer thickness of the applied mixtures varies greatly and depends on the processing method or the quantity of additional substances. The thickness ranges from 1-100 µm, preferably from 10-50 µm. This corresponds to a binder application of 0.1-5 wt. %.

The desired dose of the formulation to be applied to the device is weight out separately and distributed by pressing the granules against the spoon with a stopper to a thin layer. The layer thickness will dependent on the formulation, but preferable approximately 2 mm in height in the bottom, and sides of the spoon. The glue attaches the material to the device. When the composition is applied to the device, the glue may be in liquid form or in solution selected from the group consisting of sugar alcohols, sugars, polyvinylpyrrolidone (PVP), gums. Other binders may be employed. Normally, the binder is dissolved in a volatile solvent. As it appears from the examples herein, an especially suitable glue or adhesive agent comprises a mixture of PVP and glycerol.

The composition of the invention may be dispensed in any suitable device. Preferably the device is made of a suitable material such as a plastic based material or glass or metal, preferable a disposable material. In order to adhere to the device it is preferred that the device has a concave surface. Spoons or devices having similar shape and function are suitable in the present context.

Active Substances

In a specific embodiment the vehicle according to the invention comprises one or more active substances. The active substance may be present in admixture with the vehicle, it may be present in the granulate comprising the swelling and/or gelling agent, it may be present in microencapsulated form or embedded in a matrix, and/or it may be present in a form that allows for controlled release of the active substance.

"Drug substances" or "active substances" in accordance with the present invention include systematically distributable therapeutically, prophylactically and/or diagnostically active substances, vitamins, minerals, dietary supplements, as well as non-systemically distributable active substances. Therapeutically, prophylactically and/or diagnostically active substances may include, without limitation, antacids, analgesics, anti-inflammatories, antibiotics, laxatives, anorexics, antihistamines, antiasthmatics, antidiuretics, antiflatuents, antimigraine agents, antispaspodics, sedatives, antihyperactives, antihypertensives, tranquilizers, decongestants, beta blockers and combinations thereof. Also encompassed by the terms "drug substances" and "active substances" are the drugs and pharmaceutical active ingredients described in Mantelle U.S. Pat. No. 5,234,957 includes 18 through 21. This text is hereby incorporated by reference.

With respect to the individual dosages of the active to be incorporated in the novel dosage form this will follow the general recommendations known to the skilled person and are generally calculated based on the body weight or body surface, especially for children, and the daily dosage may naturally be divided in several dosages according to conventional treatment regimens for the active substance in question. Depending of the actual amount, a dosage may be present in a single spoon or similar dosing device or in several spoons to be ingested. Alternatively, the actual dosage can be measured based the content per volume of a pre-prepared product similar with dosing from bottles of mixtures generally employed with liquid formulations.

The active substance administered may be any compound that is suitable for oral drug administration; examples of the various classes of active substances that can be administered using the present dosage forms include, but are not limited to: analgesic agents; anesthetic agents; antiarthritic agents; respiratory drugs; anticancer agents; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antineoplastic agents; antiparkinsonism drugs; antipruritics; antipsychotics; antipyretics; antispasmodics; antitubercular agents; antiulcer agents and other gastrointestinally active agents; antiviral agents; anxiolytics; appetite suppressants; attention deficit disorder (ADD) and attention deficit hyperactivity disorder (ADHD) drugs; cardiovascular preparations including calcium channel blockers, CNS agents, and vasodilators; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nutritional agents, such as vitamins, essential amino acids and fatty acids; parasympatholytics; peptide drugs; psychostimulants; sedatives; steroids; sympathomimetics; and tranquilizers.

Several known drugs are substantially insoluble or only slightly soluble in water and accordingly difficult to formulate in solutions and suspensions for administration to children, elderly or other subjects having difficulties in swallowing and such drugs are therefore of particular interest according to the present invention and include, by way of example, the following:

Gastrointestinally active substances. Gastrointestinally active substances are particularly preferred drugs that can be administered using the present dosage forms. These types of drugs include agents for inhibiting gastric acid secretion, such as the $H_2$ receptor antagonists cimetidine, ranitidine, famotidine, and nizatidine, the $H^+$, $K^+$-ATPase inhibitors (also referred to as "proton pump inhibitors") omeprazole and lansoprazole, and antacids such as calcium carbonate, aluminum hydroxide, and magnesium hydroxide. Also included within this general group are agents for treating infection with *Helicobacter pylori* (*H. pylori*), such as metronidazole, tinidazole, amoxicillin, clarithromycin, tetracycline, thiamphenicol, and bismuth compounds (e.g., bismuth subcitrate and bismuth subsalicylate). Other gastrointestinally active substances administrable using the present dosage forms include, but are not limited to, pentagastrin, carbenoxolone, sulfated polysaccharides such as sucralfate, prostaglandins such as misoprostol, and muscarinic antagonists such as pirenzepine and telenzepine. Additionally included are antidiarrheal agents, antiemetic agents and prokinetic agents such as ondansetron, granisetron, metoclopramide, chlorpromazine, perphenazine, prochlorperazine, promethazine, thiethylperazine, triflupromazine, domperidone, trimethobenzamide, cisapride, motilin, loperamide, diphenoxylate, and octreotide.

Anti-microbial agents. These include: quinolone antibiotics such as nalidixic acid, and particularly fluorinated quinolone antibiotics such as ciprofloxacin, clinafloxacin, enoxacin, gatifloxacin, grepafloxacin, levofloxacin, lomefloxacin, moxifloxacin, norfloxacin, ofloxacin, pefloxacin, sparfloxacin, and trovafloxacin; tetracycline antibiotics and related compounds (chlortetracycline, oxytetracycline, demeclocycline, methacycline, doxycycline, minocycline, rolitetracycline); macrolide antibiotics such as erythromycin, clarithromycin, and azithromycin; streptogramin antibiotics such as quinupristin and dalfopristin; beta-lactam antibiotics, including penicillins (e.g., penicillin G, penicillin VK), anti-staphylococcal penicillins (e.g., cloxacillin, dicloxacillin, nafcillin, and oxacillin), extended spectrum penicillins (e.g., aminopenicillins such as ampicillin and amoxicillin, and the antipseudomonal penicillins such as carbenicillin), and cephalosporins (e.g., cefadroxil, cefepime, cephalexin, cefazolin, cefoxitin, cefotetan, cefuroxime, cefotaxime, ceftazidime, and ceftriaxone), and carbapenems such as imipenem, meropenem and aztreonam; aminoglycoside antibiotics such as streptomycin, gentamicin, tobramycin, amikacin, and neomycin; glycopeptide antibiotics such as teicoplanin; sulfonamide antibiotics such as sulfacetamide, sulfabenzamide, sulfadiazine, sulfadoxine, sulfamerazine, sulfamethazine, sulfamethizole, and sulfamethoxazole; anti-mycobacterials such as isoniazid, rifampin, rifabutin, ethambutol, pyrazinamide, ethionamide, aminosalicylic, and cycloserine; systemic antifungal agents such as itraconazole, ketoconazole, fluconazole, and amphotericin B; antiviral agents such as acyclovir, famcicylovir, ganciclovir, idoxuridine, sorivudine, trifluridine, valacyclovir, vidarabine, didanosine, stavudine, zalcitabine, zidovudine, amantadine, interferon alpha, ribavirin and rimantadine; and miscellaneous antimicrobial agents such as chloramphenicol, spectinomycin, polymyxin B (colistin), bacitracin, nitrofurantoin, methenamine mandelate and methenamine hippurate.

Anti-diabetic agents. These include, by way of example, acetohexamide, chlorpropamide, ciglitazone, gliclazide, glipizide, glucagon, glyburide, miglitol, pioglitazone, tolazamide, tolbutamide, triampterine, and troglitazone.

Analgesics. Non-opioid analgesic agents include apazone, etodolac, difenpiramide, indomethacin, meclofenamate, mefenamic acid, oxaprozin, phenylbutazone, piroxicam, and tolmetin; opioid analgesics include alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, and tramadol.

Anti-inflammatory agents. Anti-inflammatory agents include the nonsteroidal anti-inflammatory agents, e.g., the propionic acid derivatives as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, and fenbufen; apazone; diclofenac; difenpiramide; diflunisal; etodolac; indomethacin; ketorolac; meclofenamate; nabumetone; phenylbutazone; piroxicam; sulindac; and tolmetin. Steroidal anti-inflammatory agents include hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, and methylprednisolone.

Anti-convulsant agents. Suitable anti-convulsant (anti-seizure) drugs include, by way of example, azetazolamide, carbamazepine, clonazepam, clorazepate, ethosuximide, ethotoin, felbamate, lamotrigine, mephenyloin, mephobarbital, phenyloin, phenobarbital, primidone, trimethadione, vigabatrin, topiramate, and the benzodiazepines. Benzodiazepines, as is well known, are useful for a number of indications, including anxiety, insomnia, and nausea.

CNS and respiratory stimulants. CNS and respiratory stimulants also encompass a number of active agents. These stimulants include, but are not limited to, the following: xanthines such as caffeine and theophylline; amphetamines such as amphetamine, benzphetamine hydrochloride, dextroamphetamine, dextroamphetamine sulfate, levamphetamine, levamphetamine hydrochloride, methamphetamine, and methamphetamine hydrochloride; and miscellaneous stimulants such as methylphenidate, methylphenidate hydrochloride, modafinil, pemoline, sibutramine, and sibutramine hydrochloride.

Neuroleptic agents. Neuroleptic drugs include antidepressant drugs, antimanic drugs, and antipsychotic agents, wherein antidepressant drugs include (a) the tricyclic antidepressants such as amoxapine, amitriptyline, clomipramine, desipramine, doxepin, imipramine, maprotiline, nortriptyline, protriptyline, and trimipramine, (b) the serotonin reuptake inhibitors citalopram, fluoxetine, fluvoxamine, paroxetine, sertraline, and venlafaxine, (c) monoamine oxidase inhibitors such as phenelzine, tranylcypromine, and (−)-selegiline, and (d) other, "atypical" antidepressants such as nefazodone, trazodone and venlafaxine, and wherein antimanic and antipsychotic agents include (a) phenothiazines such as acetophenazine, acetophenazine maleate, chlorpromazine, chlorpromazine hydrochloride, fluphenazine, fluphenazine hydrochloride, fluphenazine enanthate, fluphenazine decanoate, mesoridazine, mesoridazine besylate, perphenazine, thioridazine, thioridazine hydrochloride, trifluoperazine, and trifluoperazine hydrochloride, (b) thioxanthenes such as chlorprothixene, thiothixene, and thiothixene hydrochloride, and (c) other heterocyclic drugs such as carbamazepine, clozapine, droperidol, haloperidol, haloperidol decanoate, loxapine succinate, molindone, molindone hydrochloride, olanzapine, pimozide, quetiapine, risperidone, and sertindole.

Hypnotic agents and sedatives include clomethiazole, ethinamate, etomidate, glutethimide, meprobamate, methyprylon, zolpidem, and barbiturates (e.g., amobarbital, apropbarbital, butabarbital, butalbital, mephobarbital, methohexital, pentobarbital, phenobarbital, secobarbital, thiopental).

Anxiolytics and tranquilizers include benzodiazepines (e.g., alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, triazolam), buspirone, chlordiazepoxide, and droperidol.

Anticancer agents, including antineoplastic agents: Paclitaxel, docetaxel, camptothecin and its analogues and derivatives (e.g., 9-aminocamptothecin, 9-nitrocamptothecin, 10-hydroxy-camptothecin, irinotecan, topotecan, 20-O-.beta.-glucopyranosyl camptothecin), taxanes (baccatins, cephalomannine and their derivatives), carboplatin, cisplatin, interferon-.alpha.sub.2A, interferon-.alpha.sub.2B, interferon-.alpha.sub.N3 and other agents of the interferon family, levamisole, altretamine, cladribine, tretinoin, procarbazine, dacarbazine, gemcitabine, mitotane, asparaginase, porfimer, mesna, amifostine, mitotic inhibitors including podophyllotoxin derivatives such as teniposide and etoposide and vinca alkaloids such as vinorelbine, vincristine and vinblastine.

Antihyperlipidemic agents. Lipid-lowering agents, or "hyperlipidemic" agents," include HMG-CoA reductase inhibitors such as atorvastatin, simvastatin, pravastatin, lovastatin and cerivastatin, and other lipid-lowering agents such as clofibrate, fenofibrate, gemfibrozil and tacrine.

Anti-hypertensive agents. These include amlodipine, benazepril, darodipine, dilitazem, diazoxide, doxazosin, enalapril, eposartan, losartan, valsartan, felodipine, fenoldopam, fosinopril, guanabenz, guanadrel, guanethidine, guanfacine, hydralazine, metyrosine, minoxidil, nicardipine, nifedipine, nisoldipine, phenoxybenzamine, prazosin, quinapril, reserpine, and terazosin.

Cardiovascular preparations. Cardiovascular preparations include, by way of example, angiotensin converting enzyme (ACE) inhibitors such as enalapril, 1-carboxymethyl-3-1-carboxy-3-phenyl-(1S)-propylamino-2,3,4,5-tetrahydro-1H-(3S)-1-benzazepine-2-one, amino-1-carboxy-1S-pentyl) amino-2,-3,4,5-tetrahydro-2-oxo-3S-1H-1-benzazepine-1-acetic acid or 3-(1-ethoxycarbonyl-3-phenyl-(1S)-propylamino)-2,3,4,5-tetrahydro-2-oxo-(-3S)-benzazepine-1-acetic acid monohydrochloride; cardiac glycosides such as digoxin and digitoxin; inotropes such as aminone and milrinone; calcium channel blockers such as verapamil, nifedipine, nicardipene, felodipine, isradipine, nimodipine, bepridil, amlodipine and diltiazem; beta-blockers such as atenolol, metoprolol; pindolol, propafenone, propranolol, esmolol, sotalol, timolol, and acebutolol; antiarrhythmics such as moricizine, ibutilide, procainamide, quinidine, disopyramide, lidocaine, phenyloin, tocamide, mexiletine, flecamide, encamide, bretylium and amiodarone; and cardioprotective agents such as dexrazoxane and leucovorin; and vasodilators such as nitroglycerin; and diuretic agents such as hydrochlorothiazide, furosemide, bumetanide, ethacrynic acid, torsemide, azosemide, muzolimine, piretanide, and tripamide.

Anti-viral agents. Antiviral agents that can be delivered using the present dosage forms include the antiherpes agents acyclovir, famciclovir, foscamet, ganciclovir, idoxuridine, sorivudine, trifluridine, valacyclovir, and vidarabine; the antiretroviral agents didanosine, stavudine, zalcitabine, and zidovudine; and other antiviral agents such as amantadine, interferon alpha, ribavirin and rimantadine.

Sex steroids. The sex steroids include, first of all, progestogens such as acetoxypregnenolone, allylestrenol, anagestone acetate, chlormadinone acetate, cyproterone, cyproterone acetate, desogestrel, dihydrogesterone, dimethisterone, ethisterone (17.alpha.-ethinyltestoster-one), ethynodiol diacetate, fluorogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. Also included within this general class are estrogens, e.g.: estradiol (i.e., 1,3,5-estratriene-3,17.beta.-diol, or "17.beta.-estradiol") and its esters, including estradiol benzoate, valerate, cypionate, heptanoate, decanoate, acetate and diacetate; 17.alpha.-estradiol; ethinylestradiol (i.e., 17.alpha.-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Androgenic agents, also included within the general class of sex steroids, are drugs such as the naturally occurring androgens androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 4-dihydrotestosterone (DHT; also termed "stanolone"), 5.alpha.-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone.

Muscarinic receptor agonists and antagonists. Muscarinic receptor agonists include, by way of example: choline esters such as acetylcholine, methacholine, carbachol, bethanechol (carbamylmethylcholine), bethanechol chloride, cholinomimetic natural alkaloids and synthetic analogs thereof, including pilocarpine, muscarine, McN-A-343, and oxotremorine. Muscarinic receptor antagonists are generally belladonna alkaloids or semisynthetic or synthetic analogs thereof, such as atropine, scopolamine, homatropine, homatropine methyl bromide, ipratropium, methantheline, methscopolamine and tiotropium.

Peptide drugs. Peptidyl drugs include the peptidyl hormones activin, amylin, angiotensin, atrial natriuretic peptide (ANP), calcitonin, calcitonin gene-related peptide, calcitonin N-terminal flanking peptide, ciliary neurotrophic factor (CNTF), corticotropin (adrenocorticotropin hormone, ACTH), corticotropin-releasing factor (CRF or CRH), epidermal growth factor (EGF), follicle-stimulating hormone (FSH), gastrin, gastrin inhibitory peptide (GIP), gastrin-releasing peptide, gonadotropin-releasing factor (GnRF or GNRH), growth hormone releasing factor (GRF, GRH), human chorionic gonadotropin (hCH), inhibin A, inhibin B, insulin, luteinizing hormone (LH), luteinizing hormone-releasing hormone (LHRH), .alpha.-melanocyte-stimulating hormone, .beta.-melanocyte-stimulating hormone, .gamma.-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, vasoactive intestinal peptide (VIP), and vasopressin. Other peptidyl drugs are the cytokines, e.g., colony stimulating factor 4, heparin binding neurotrophic factor (HBNF), interferon-a, interferon .alpha.-2a, interferon .alpha.-2b, interferon .alpha.-n3, interferon-.beta., etc., interleukin-1, interleukin-2, interleukin-3, interleukin-4, interleukin-5, interleukin-6, etc., tumor necrosis factor, tumor necrosis factor-.alpha., granuloycte colony-stimulating factor (G-CSF), granulocyte-macrophage colony-stimulating factor (GM-CSF), macrophage colony-stimulating factor, midkine (MD), and thymopoietin. Still other peptidyl drugs that can be advantageously delivered using the present systems include endorphins (e.g., dermorphin, dynorphin, alpha.-endorphin, .beta.-endorphin, .gamma.-endorphin, .sigma.-endorphin, [Leu.sup.5]enkephalin, [Met.sup.5]enkephalin, substance P), kinins (e.g., bradykinin, potentiator B, bradykinin potentiator C, kallidin), LHRH analogues (e.g., buserelin, deslorelin, fertirelin, goserelin, histrelin, leuprolide, lutrelin, nafarelin, tryptorelin), and the coagulation factors, such as .alpha.sub.1-antitrypsin, .alpha.sub.2-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor, plasma thromboplastin component or PTC), factor X (Stuart-Power factor), factor XI (plasma thromboplastin antecedent or PTA), factor XII (Hageman factor), heparin cofactor II, kallikrein, plasmin, plasminogen, prekallikrein, protein C, protein S, and thrombomodulin and combinations thereof.

Genetic material may also be delivered using the present dosage forms, e.g., nucleic acids, RNA, DNA, recombinant RNA, recombinant DNA, antisense RNA, antisense DNA, ribozymes, ribooligonucleotides, deoxyribonucleotides, antisense ribooligonucleotides, and antisense deoxyribooligonucleotides. Representative genes include those encoding for vascular endothelial growth factor, fibroblast growth factor, Bcl-2, cystic fibrosis transmembrane regulator, nerve growth factor, human growth factor, erythropoietin, tumor necrosis factor, and interleukin-2, as well as histocompatibility genes such as HLA-B7.

In a preferred embodiment for a pediatric product and use according to the invention, the active drug is selected from Abacavir; Acetazolamide; Adefovir; Albuterol; Albuterol; Alendronate; Almotriptan; Alosetron; Alprazolam; Amiodarone; Amlexanox; Amlodipine; the combination Amlodipine/Benazepril; Ammonium Lactate; Amphetamine (including mixed salts); Amprenavir; Anagrelide; Anastrozole; Argatroban; Aripiprazole; Atazanavir; Atomoxetine; Atorvastatin; the mixture Atovaquone/Proguanil; Azelastine; Baclofen; Balsalazide; Beclomethasone; Beclomethasone; Benazepril; Betamethasone; Betaxolol; Betaxolol; Bicalutamide; Bisoprolol; Brimonidine; Brinzolamide; Budesonide; Buproprion; Buspirone; Busulfan; C-Urea; Calcitriol; Candesartan; Carboplatin; Carteolol, Carvedilol; Caspofungin; Celecoxib; Cerivastatin; Cetirizine; Cilostazol; Cimetidine; Ciprofloxacin; Ciprofloxacin; Cisatracurium; Citalopram; Clopidogrel; Colesevelam; Cromolyn; Cromolyn; Cytarabine; Desflurane; Desloratadine; Dexrazoxane; Dichlorphenamide; Didanosine; Dorzolamide, Efavirenz; Eletriptan; Emtricitabine; Enalapril; Enfuvirtide (T-20); Enoxaparin; Epirubicin; Eplerenone; Ertapenem, Esmolol; Esomeprazole; Etodolac; Famciclovir; Famotidine; Felodipine; Fenoldopam; Fentanyl; Fentanyl; Fexofenadine; Fluconazole; Fludarabine, Iuocinolone; Fluoxetine; Fluticasone; Fluvastatin; Fluvoxamine; Formoterol; Fosinopril; Fosphenyloin; Fulvestrant; Gabapentin; Gatifloxacin; Gatifloxacin; Gemcitabine; Gemtuzumab; Gentamicin; Glatiramer; Glimepiride; Glipizide/Metformin; Glyburide/Metformin; Granisetron; Hydrocortisone, Hydroxyurea; Ibuprofen; Ibuprofen/pseudoephedrine; Imatinib; Imiquimod; Indinavir; Insulin glargine; Irbesartan; Irinotecan; Isotretinoin; Itraconazole; Ketoconazole, Ketorolac; Labetalol; Lamivudine, Lamotrigine; Lansoprazole; Leflunomide; Levalbuterol; Levetiracetam; Levobetaxolol; Levobunolol; Levofloxacin; Levofloxacin; Linezolid; Lisinopril; Lisinopril; Lopinavir/Ritonavir; Loratadine; Losartan; Lovastatin; Mesalamine; Metformin; Methazolamide; Methylphenidate; Metipranolol; Metoprolol; Midazolam; Milrinone; Minoxidil; Mirtazapine; Modafinil; Moexipril; Mometasone; Montelukast; Morphine; Moxifloxacin; Nabumetone; Nateglinide; Nefazodone; Nelfinavir; Nevirapine; Nicotine; Nizatidine; Norfloxacin; Norgestimate/ethinyl estradiol; Octreotide; Ofloxacin; Olanzapine; Olmesartan; Omeprazole; Ondansetron; Orlistat; Oseltamivir; Oxaprozin; Oxcarbazepine; Oxybutynin; Oxybutynin; Oxycodone; Pantoprazole; Paricalcitol; Paroxetine; Pegvisomant; Pemirolast; Pimecrolimus; Pioglitazone; Pravastatin; Propofol; Quetiapine Fumerate; Quinapril; Rabeprazole; Ramipril; Ranitidine; Remifentanil, Repaglinide; Ribavirin/Interferon alfa-2B, recombinant, Rifapentine; Risedronate; Risperidone; Ritonavir; Rocuronium; Rofecoxib; Ropivacaine; Rosiglitazone; Rosiglitazone; Salmeterol; Saquinavir; Sertraline; Sevelamer; Sevoflurane; Sibutramine; Sildenafil; Simvastatin; Sirolimus; Sodium ferric gluconate complex; Sotalol; Stavudine; Sumatriptan; Tacrolimus; Tamoxifen; Temozolomide; Tenofovir; Terbinafine; Testosterone; Timolol; Tolterodine; Topiramate; Topotecan; Tramadol; Valacyclovir; Valganciclovir, Valproate; Valsartan; Venlafaxine, Verapamil; Vinorelbine; Voriconazole; Zafirlukast; Zanamivir; Ziprasidone; Zoledronic acid; Zolmitriptan; Zonisamide.

As incorporated be reference according to Mantelle U.S. Pat. No. F,234,957:

1. Analgesic anti-inflammatory agents such as, acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and the like;

2. Drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cyclobarbital, codeine, lidocaine, tetracaine, dyclonine, dibucaine, cocaine, procaine, mepivacaine, bupivacaine, etidocaine, prilocaine, benzocaine, fentanyl, nicotine, and the like;

3. Antihistaminics or antiallergic agents such as, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, chlorpheniramine, and the like;

4. Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like;

5. Steroids such as, androgenic steroids, such as, testosterone, methyltestosterone, fluoxymesterone, estrogens such as, conjugated estrogens, esterified estrogens, estropipate, 17-.beta.estradiol, 17-.beta.estradiol valerate, equilin, mestranol, estrone, estriol, 17-.beta.ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-.alpha.hydroxyprogesterone, dydrogesterone, dimethisterone, ethinylestrenol, norgestrel, demegestone, promegestone, megestrol acetate, and the like;

6. Respiratory agents such as, theophilline and beta.sub.2-adrenergic agonists, such as, albuterol, terbutaline, metaproterenol, ritodrine, carbuterol, fenoterol, quinterenol, rimiterol, solmefamol, soterenol, tetroquinol, and the like;

7. Sympathomimetics such as, dopamine, norepinephrine, phenylpropanolamine, phenylephrine, pseudoephedrine, amphetamine, propylhexedrine, arecoline, and the like;

8. local anesthetics such as, benzocaine, procaine, dibucaine, lidocaine, and the like;

9. Antimicrobial agents including antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides, nitrofrantoin, nystatin, amphotericin, fradiomycin, sulfonamides, purrolnitrin, clotrimazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone, and the like;

10. Antihypertensive agents such as, clonidine, alpha.-methyldopa, reserpine, syrosingopine, rescinnamine, cinnarizine, hydrazine, prazosin, and the like;

11. Antihypertensive diuretics such as, chlorothiazide, hydrochlorothiazide, bendoflumethazide, trichlormethiazide, furosemide, tripamide, methylclothiazide, penfluzide, hydrothiazide, spironolactone, metolazone, and the like;

12. Cardiotonics such as, digitalis, ubidecarenone, dopamine, and the like;

13. Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine, and the like;

14. Vasoconstrictors such as, dihydroergotamine, dihydroergotoxine, and the like;

15. .beta.-blockers or antiarrhythmic agents such as, timolol pindolol, propranolol, and the like;

16. Calcium antagonists and other circulatory organ agents, such as, aptopril, diltiazem, nifedipine, nicardipine, verapamil, bencyclane, ifenprodil tartarate, molsidomine, clonidine, prazosin, and the like;

17. Anti-convulstants such as, nitrazepam, meprobamate, phenyloin, and the like;

18. Agents for dizziness such as, isoprenaline, betahistine, scopolamine, and the like;

19. Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam, and the like;

20. Antipsychotics such as, phenothiazines including thiopropazate, chlorpromazine, triflupromazine, mesoridazine, piperracetazine, thioridazine, acetophenazine, fluphenazine, perphenazine, trifluoperazine, and other major tranqulizers such as, chlorprathixene, thiothixene, haloperidol, bromperidol, loxapine, and molindone, as well as, those agents used at lower doses in the treatment of nausea, vomiting, and the like;

21. Muscle relaxants such as, tolperisone, baclofen, dantrolene sodium, cyclobenzaprine;

22. Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, and the like;

23. Respiratory agents such as, codeine, ephedrine, isoproterenol, dextromethorphan, orciprenaline, ipratropium bromide, cromglycic acid, and the like;

24 Non-steroidal hormones or antihormones such as, corticotropin, oxytocin, vasopressin, salivary hormone, thyroid hormone, adrenal hormone, kallikrein, insulin, oxendolone, and the like;

25. Vitamins such as, vitamins A, B, C, D, E and K and derivatives thereof, calciferols, mecobalamin, and the like for dermatologically use;

26. Antitumor agents such as, 5-fluorouracil and derivatives thereof, krestin, picibanil, ancitabine, cytarabine, and the like;

27. Enzymes such as, lysozyme, urokinaze, and the like;

28. Herb medicines or crude extracts such as, glycyrrhiza, aloe, Sikon (Lithospermi Radix), and the like;

29. Miotics such as pilocarpine, and the like; lo 30. Cholinergic agonists such as, choline, acetylcholine, methacholine, carbachol, bethanechol, pilocarpine, muscarine, arecoline, and the like;

31. Antimuscarinic or muscarinic cholinergic blocking agents such as, atropine, scopolamine, homatropine, methscopolamine, homatropine methylbromide, methantheline, cyclopentolate, tropicamide, propantheline, anisotropine, dicyclomine, eucatropine, and the like;

32. Mydriatics such as, atropine, cyclopentolate, homatropine, scopolamine, tropicamide, eucatropine, hydroxyamphetamine, and the like;

33. Psychic energizers such as 3-(2-aminopropy)indole, 3-(2-aminobutyl)indole, and the like;

34. Humoral agents such as, the prostaglandins, natural and synthetic, for example PGE.sub.1, PGE.sub.2.alpha., and PGF.sub.2.alpha., and the PGE.sub.1 analog misoprostol.
35. Antispasmodics such as, atropine, methantheline, papaverine, cinnamedrine, methscopolamine, and the like;
36. Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone, and the like;
37. Anti-diabetics such as, insulin, and anticancer drugs such as, tamoxifen, methotrexate, and the like;
38. Anorectic drugs such as, dextroamphetamine, methamphetamine, phenylpropanolamine, fenfluramine, diethylpropion, mazindol, phentermine, and the like;
39. Anti-allergenics such as, antazoline, methapyrilene, chlorpheniramine, pyrilamine, pheniramine, and the like;
40. Decongestants such as, phenylephrine, ephedrine, naphazoline, tetrahydrozoline, and the like;
41. Antipyretics such as, aspirin, salicylamide, and the like;
42. Antimigrane agents such as, dihydroergotamine, pizotyline, and the like;
43. Anti-malarials such as, the 4-aminoquinolines, alphaminoquinolines, chloroquine, pyrimethamine, and the like;
44. Anti-ulcerative agents such as, misoprostol, omeprazole, enprostil, and the like;
45. Peptides such as, growth releasing factor, and the like;
46. Anti-estrogen or anti-hormone agents such as, tamoxifen or human chorionic gonadotropin, and the like;
47. Antiulcer agents such as, allantoin, aldioxa, alcloxa, N-methylscopolamine methylsuflate, and the like;
48. Antidiabetics, and the like.

The drugs mentioned above can be used in combination as required. Moreover, the above drugs may be used either in the free form or, if capable of forming salts, in the form of a salt with a suitable acid or base. If the drugs have a carboxyl group, their esters can be employed.

The acid mentioned above may be an organic acid, for example, methanesulfonic acid, lactic acid, tartaric acid, fumaric acid, maleic acid, acetic acid, or an inorganic acid, for example, hydrochloric acid, hydrobromic acid, phosphoric acid or sulfuric acid. The base may be an organic base, for example, ammonia, triethylamine, or an inorganic base, for example, sodium hydroxide or potassium hydroxide. The esters mentioned above may be alkyl esters, aryl esters, aralkyl esters, and the like.

In one embodiment of the invention, the active substance is selected from the following:
Antibacterials Including Metronidazole Although antibiotics and other antibacterials are a very diverse class of compounds they are often classified and discussed in groups. They may be classified according to their mode of action or spectrum of antimicrobial activity, but generally those with similar chemical structures are grouped together.
Aminoglycosides Amikacin, Apramycin, Arbekacin, Astromicin, Bekanamycin, Dibekacin, Dihydrostreptomycin, Framycetin, Gentamicin, Isepamicin, Kanamycin, Micronomicin, Neomycin, Netilmicin, Sisomicin, Streptomycin, Tobramycin.
Antimycobacterials Drug Groups: Antimycobacterials Aminosalicylic Acid, Capreomycin, Clofazimine, Cycloserine, Dapsone, Ethambutol, Ethionamide, Isoniazid, Methaniazide, Morinamide, Protionamide, Pyrazinamide, Rifabutin, Rifampicin, Rifamycin, Rifapentine, Rifaximin, Thioacetazone.

Cephalosporins and Related Beta Lactams

Drug Groups: Cephalosporins, related Beta Lactams or cephem antibiotics Aztreonam, Betamipron, Biapenem, Carumonam, Cefaclor, Cefadroxil, Cefalexin, Cefalonium, Cefaloridine, Cefalotin, Cefamandole, Cefazolin, Cefapirin, Cefatrizine, Cefcapene, Cefdinir, Cefditoren, Cefepime, Cefetamet, Cefixime, Cefluprenam, Cefmenoxime, Cefmetazole, Cefminox, Cefodizime, Cefonicid, Cefoperazone, Ceforamide, Cefoselis, Cefotaxime, Cefotetan, Cefotiam, Cefoxitin, Cefozopran, Cefpiramide, Cefpirome, Cefpodoxime, Cefprozil, Cefquinome, Cefsulodin, Ceftazidime, Cefteram, Ceftezole, Ceftibuten, Ceftiofur, Ceftizoxime, Ceftriaxone, Cefuroxime, Cefradine, Cilastatin, Faropenem, Flomoxef, Imipenem, Latamoxef, Loracarbef, Meropenem, Panipenem,
Chloramphenicols Azidamfenicol, Chloramphenicol, Florfenicol, Thiamphenicol, Avoparcin, Ramoplanin, Teicoplanin, Vancomycin,
Lincosamides Clindamycin, Lincomycin, Pirlimycin,
Macrolides Azithromycin, Clarithromycin, Dirithromycin, Erythromycin, Flurithromycin, Josamycin, Kitasamycin, Midecamycin, Oleandomycin, Pristinamycin, Quinupristin/Dalfopristin, Rokitamycin, Roxithromycin, Spiramycin, Tilmicosin, Troleandomycin, Tylosin, Virginiamycin,
Penicillins The beta-lactamase inhibitors clavulanic acid, sulbactam, and tazobactam are used to extend the antimicrobial range of certain beta-lactam antibiotics. Amoxicillin, Ampicillin, Aspoxicillin, Azidocillin, Azlocillin, Bacampicillin, Benethamine Penicillin, Benzathine Benzylpenicillin, Benzathine Phenoxymethylpenicillin, Benzylpenicillin, Carbenicillin, Carfecillin, Carindacillin, Ciclacillin, Clavulanic Acid, Clemizole Penicillin, Clometocillin, Cloxacillin, Dicloxacillin, Flucloxacillin, Mecillinam, Metampicillin, Meticillin, Meziocillin, Nafcillin, Oxacillin, Penethamate, Pheneticillin, Phenoxymethylpenicillin, Piperacillin, Pivampicillin, Pivmecillinam, Procaine Penicillin [Procaine Benzylpenicillin], Propicillin, Sulbactam, Sulbenicillin, Sultamicillin, Tazobactam, Temocillin, Ticarcillin,
Quinolones Acrosoxacin [Rosoxacin], Alatrofloxacin, Balofloxacin, Cinoxacin, Ciprofloxacin, Clinafloxacin, Danofloxacin, Difloxacin, Enoxacin, Enrofloxacin, Fleroxacin, Flumequine, Gatifloxacin Gemifloxacin, Grepafloxacin, Levofloxacin, Lomefloxacin, Marbofloxacin, Moxifloxacin, Nadifloxacin, Nalidixic Acid, Norfloxacin, Ofloxacin, Orbifloxacin, Oxolinic Acid, Pefloxacin, Pipemidic Acid, Piromidic Acid, Prulifloxacin, Rufloxacin, Sarafloxacin, Sparfloxacin, Temafloxacin, Tosufloxacin, Trovafloxacin,
Sulfonamides and Diaminopyrimidines Baquiloprim, Brodimoprim, Calcium Sulfaloxate, Co-tetroxazine, Co-trifamole, Co-trimazine, Co-trimoxazole, Formosulfathiazole Mafenide, Ormetoprim, Phthalylsulfathiazole, Succinylsulfathiazole, Sulfabenzamide, Sulfaclozine, Sulfachrysoidine, Sulfadicramide, Sulfadoxine, Sulfamerazine, Sulfamethylthiazole, Sulfametopyrazine, Sulfametrole, Sulfamonomethoxine, Sulfaquinoxaline, Sulfasuccinamide, Sulfatroxazole, Sulfacetamide, Sulfachlorpyridazine, Sulfadiazine, Sulfadiazine Silver, Sulfadimethoxine, Sulfadimidine, Sulfafurazole, Sulfaguanidine, Sulfamethizole, Sulfamethoxazole, Sulfamethoxypyridazine, Sulfamoxole, Sulfanilamide, Sulfapyridine, Sulfisomidine, Sulfathiazole, Sulfacarbamide, Tetroxoprim, Trimethoprim, Tetracyclines Chlortetracycline, Demeclocycline, Doxycycline, Lymecycline, Meclocycline, Methacycline, Minocycline, Oxytetracycline, Rolitetracycline, Tetracycline, Miscellaneous Antibacterials Acediasulfone, Arsanilic Acid, Avilamycin, Bacitracin, Bambermycin, Carbadox, Chlorquinaldol, Clioquinol, Clofoctol, Colistin, Daptomycin, Evernimicin, Fosfomycin, Furaltadone, Fusafungine, Fusidic Acid, Gramicidin, Halquinol, Methenamine, Linezolid, Magainins, Mandelic Acid, Mupirocin, Nifuroxazide, Nifurtoinol, Nifurzide, Nisin, Nitrofurantoin, Nitrofurazone, Nitroxoline, Novobiocin, Polymyxin B, Spectinomycin, Sulfamazone, Taurolidine, Telithromycin, Terizidone, Thenoic Acid, Thiostrepton, Tiamulin, Trospectomycin, Tyrothricin, Valnemulin, Xibornol, Anthelmintics Albendazole, Diethylcarbamazine, Ivermectin, Levamisole, Mebendazole, Niclosamide, Oxamniquine, piperazine, Praziquantel, Pyrantel, Thiabendazole.

Antimalarial Drugs 4-methanolquinoline derivatives such as the cinchona alkaloids and mefloquine. The 4-aminoquinolines, such as chloroquine, hydroxychloroquine, and amodiaquine. The 8-aminoquinolines such as primaquine and tafenoquine. The biguanides, such as proguanil and chlorproguanil. The diaminopyrimidines such as pyrimethamine. The dichlorobenzylidine lumefantrine. The hydroxynaphthoquinones, such as atovaquone. The 9-phenanthrenemethanols such as halofantrine. The sesquiterpene lactones such as artemisinin and its derivatives. The sulfonamides sulfadoxine and sulfametopyrazine. The tetracyclines, such as doxycycline and tetracycline. The lincosamide, clindamycin. The sulfones such as dapsone.

Antiprotozoals

The antimony compounds including meglumine antimonate and sodium stibogluconate, the aromatic diamidines including pentamidine, the arsenicals including the pentavalent compounds acetarsol and tryparsamide, and melarsoprol which is trivalent, the dichloroacetamides including diloxanide, the halogenated hydroxyquinolines including diiodohydroxyquinoline, the nitrofurans including furazolidone, nifuratel, and nifurtimox, and the 5-nitroimidazoles including metronidazole, nimorazole, ornidazole, secnidazole, and tinidazole. Other drugs include atovaquone, benznidazole, dehydroemetine, eflornithine, mepacrine, and suramin.

Antivirals

Anti-Asthma Drug Groups

Antimuscarinics and Beta Agonists.

such as the quaternary ammonium compounds ipratropium bromide and oxitropium bromide, Salmeterol, Albuterol, Bitolterol, Isoetharine, Metaproterenol, Pirbuterol, Terbutaline, Isoproterenol, Ephedrine, Epinephrine Salbutamol.

Corticosteroids.

Beclomethasone dipropionate, Budesonide Turbuhaler, Flunisolide, Fluticasone, Triamcinolone acetonide.

Leukotriene Inhibitors and Antagonists.

Zafirlukast, Montelukast.

Mast Cell Stabilisers.

Sodium cromoglicate and Nedocromil sodium.

Xanthines.

Theophylline and its derivatives.

Antifungals

Flucytosine, Griseofulvin, Ketoconazole, Miconazole.

As used herein, the term vitamin refers to trace organic substances that are required in the diet. For the purposes of the present invention, the term vitamin(s) include, without limitation, thiamine, riboflavin, nicotinic acid, pantothenic acid, pyrdoxine, biotin, folic acid, vitamin B.sub.12, lipoic acid, ascorbic acid, vitamin A, vitamin D, vitamin E and vitamin K. Also included within the term vitamin are the coenzymes thereof. Coenzymes are specific chemical forms of vitamins. Coenzymes include thiamine pyrophosphates (TPP), flavin mononucleotide (FMM), flavin adenine dinucleotive (FAD), Nicotinamide adenine dinucleotide (NAD), Nicotinamide adenine dinucleotide phosphate (NADP) Coenzyme A (CoA) pyridoxal phosphate, biocytin, tetrahydrofolic acid, coenzyme B.sub.12, lipoyllysine, 11-cis-retinal, and 1,25-dihydroxycholecalciferol. The term vitamin(s) also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The term "dietary supplement" as used herein means a substance, which has an appreciable nutritional effect when administered in small amounts. Dietary supplements include, without limitation, such ingredients as bee pollen, bran, wheat germ, kelp, cod liver oil, ginseng, and fish oils, amino acids, proteins and mixtures thereof. As will be appreciated, dietary supplements may incorporate vitamins and minerals.

In general, the amount of the active substance incorporated in the dosage form according to the invention may be selected according to known principles of pharmacy. An effective amount of pharmaceutical ingredient is specifically contemplated. By the term effective amount, it is understood that, with respect to for example pharmaceuticals, a therapeutically, prophylactically and/or diagnostically effective amount is contemplated. An effective amount is the amount or quantity of a drug substance, which is sufficient to elicit the required or desired therapeutic response, or in other words, the amount, which is sufficient to elicit an appreciable biological response when administered to a patient. As used herein the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA. The amount of active agent used can vary widely from a few milligrams to 100,000 milligrams or more.

Preparation of a Pharmaceutical Composition

A pharmaceutical composition according to the invention may be prepared by blending of at least:

1) One or more active substances as particulate matter. Either as pure material (crystals or amorphous, in powder form) or encapsulated by a coat or trapped in a matrix or bound to an ion-exchange resin.

2) One or more swelling/gelling materials and, optionally:

3) Sweetening agents

4) Flavours

5) Colorants

In one embodiment it is possible to use the gelling agent in solution as a binder in granulating and as a glue for giving the formulation the desired shape, however once the gelling agent has been hydrated, the gelling properties may be reduced, accordingly sometimes the gelling agent used in solution as a binder is identical with the bulk gelling agent (example Kelcogel® LT100), sometimes it is a different grade of the same gelling agent (Kelcogel® LT100 bulk, Kelcogel® F as binder) and sometimes a different binder altogether (Kelcogel® LT100 as bulk, Keltrol as binder). The desired shape mentioned could be, for example, granulating the mixture of active substances, gelling agent, sweetener and flavour and subsequently moulding and gluing the granules to the concave surface of a spoon, preferable in a relative thin layer of 0.5 to 5 mm thick. This strategy contributes to that the powder/particulate material obtained as the novel dosage form can be converted into a pudding-like mass without application of any shear force and within the desired time period. This feature is very advantageous in that it is possible to use the novel dosage form also for very small amounts of active substances as there is no risk that active substance will be lost e.g. on a spoon or stirrer during stirring or mechanical mixing. In other words, the dose form presents the active substance in a form that ensures the right dose to be ingested. To the best of the inventors' knowledge this is the first comparable semi-liquid alternative in this respect to a tablet or capsule dosage form.

More specifically, the invention relates to a method for preparing a pharmaceutical composition according to the invention, the method comprising blending the dry components to a homogeneous mixture and optionally granulating the mixture with a binder.

In a specific embodiment, the invention relates to a method for preparing a pharmaceutical composition according to the invention comprising one or more excipients and/or active ingredients which have a solubility substantial lower than the solubility of the gellan gum, wherein the method comprises
i) granulating a first blend comprising gellan gum but essentially not containing the one or more excipients and/or active ingredients which have a solubility substantial lower than the solubility of the gellan gum,
ii) adding the one or more excipients and/or active ingredients which have a solubility substantial lower than the solubility of the gellan gum to the granulated first blend.

In a subsequent step, the one or more excipients and/or active ingredients which have a solubility substantial lower than the solubility of the gellan gum is added to the granulated first blend as a blend or granulate with additional excipients.

The foregoing will be better understood with reference to the following examples which detail certain procedures for manufacture of tablets in accordance to the present invention. All references made to these examples are for the purposes of illustration. They are not to be considered limiting as to the scope and nature of the present invention.

FIGURES

Figure 6:
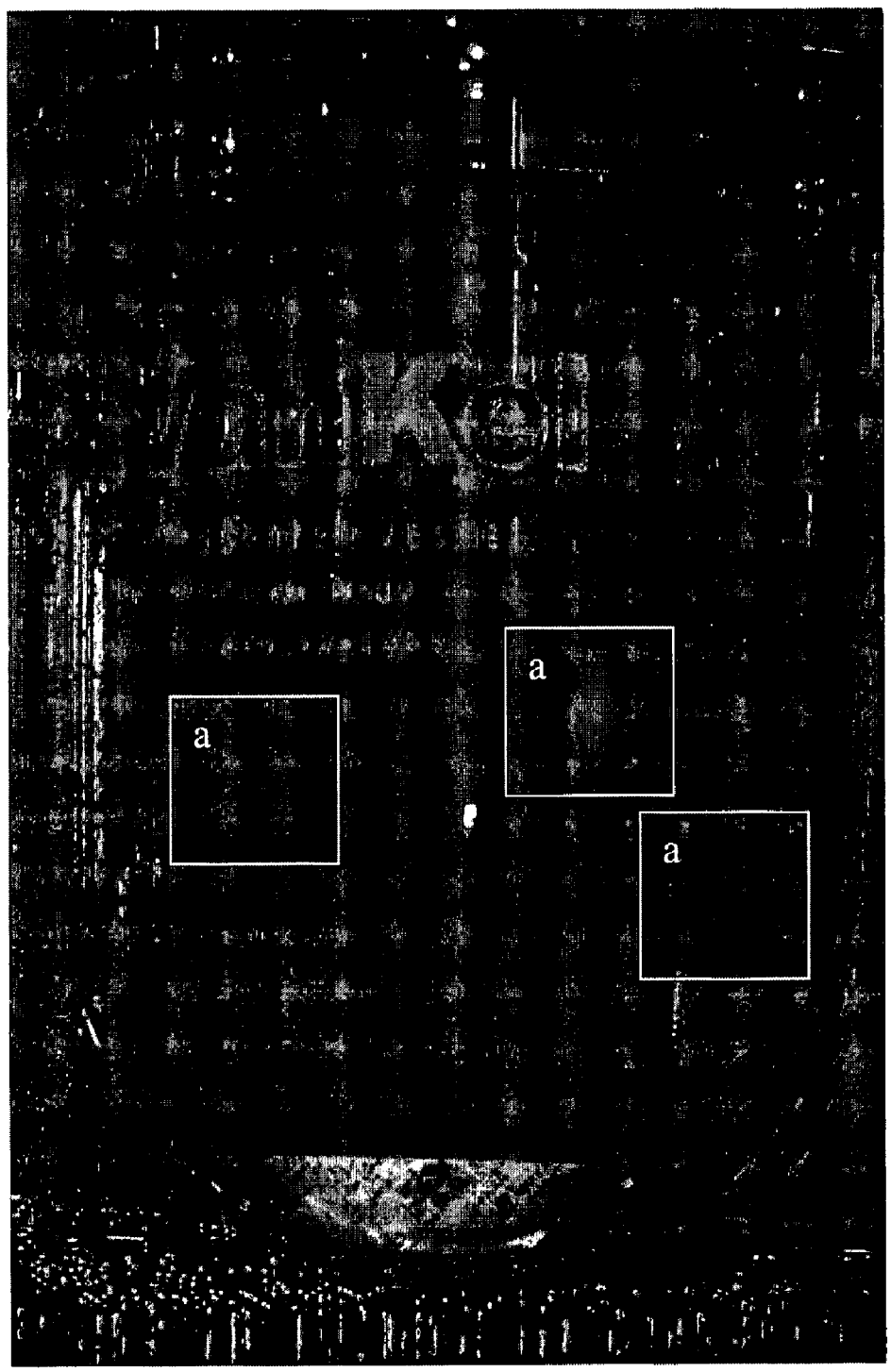
FIG. 6 shows the dissolution at low pH of the formulation according to Example 24 demonstrating disintegration into material with individual flakes varying in size from approximately 1 to 5 mm.
Figure 7:
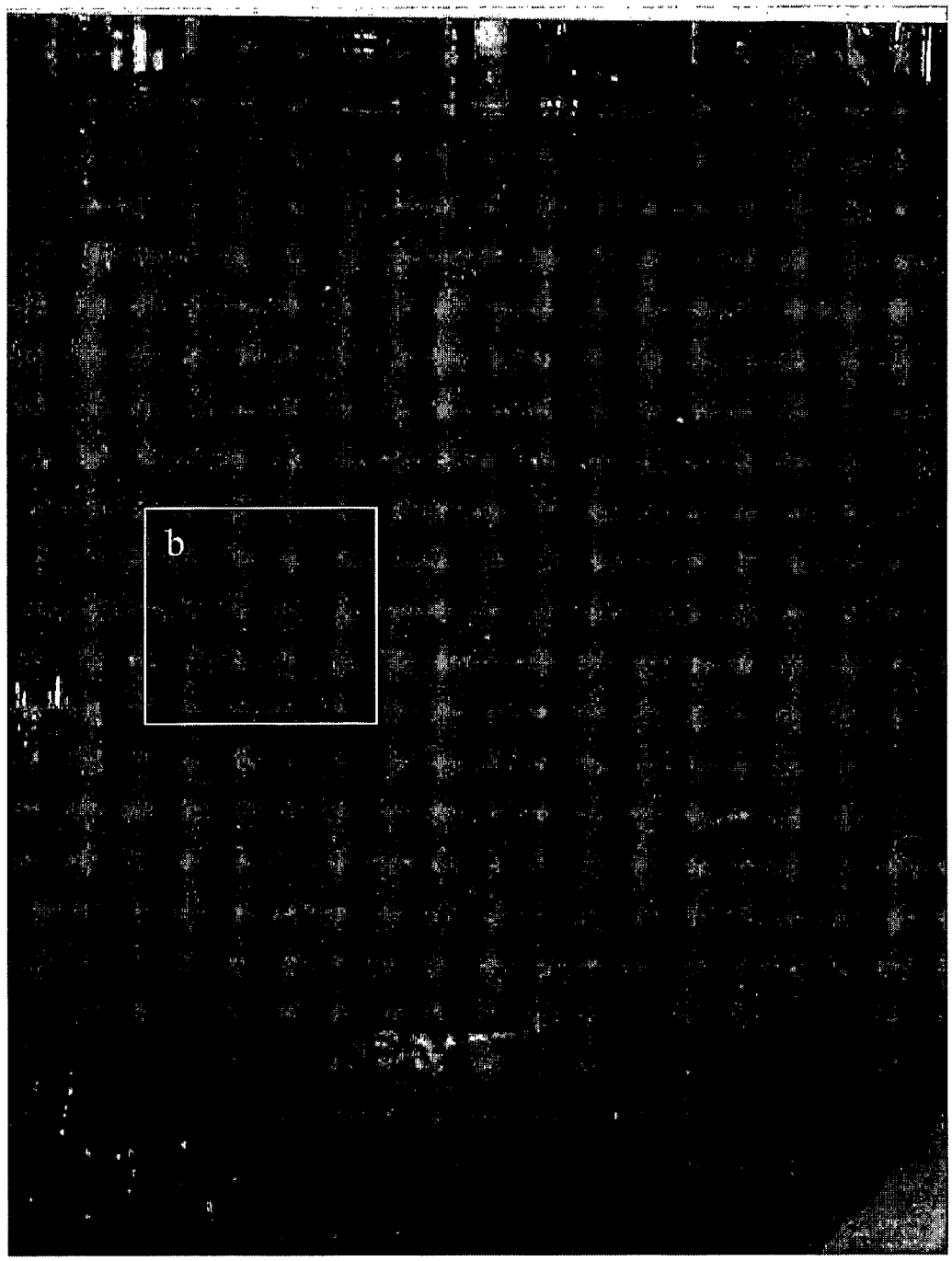
Figure 8:
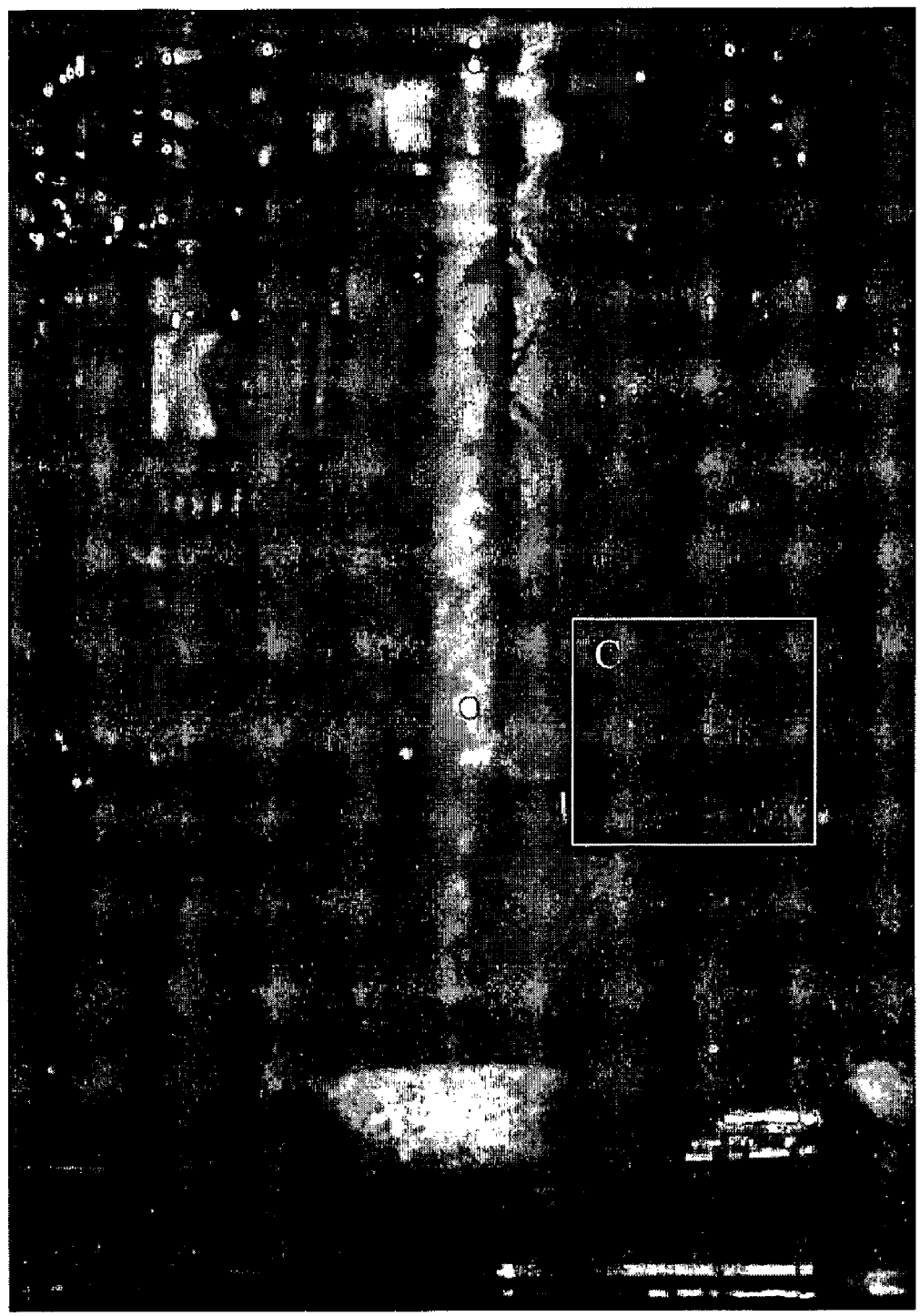

FIG. 7 demonstrates the dissolution similar to FIG. 6 in a media at pH 4.8 demonstrating complete disintegration of the material FIG. 8 demonstrates the dissolution similar to FIG. 6 in a media at pH 6.8 demonstrating complete disintegration of the material into very small and fluffy material representing the non soluble material of the formulation.

Figure 9:
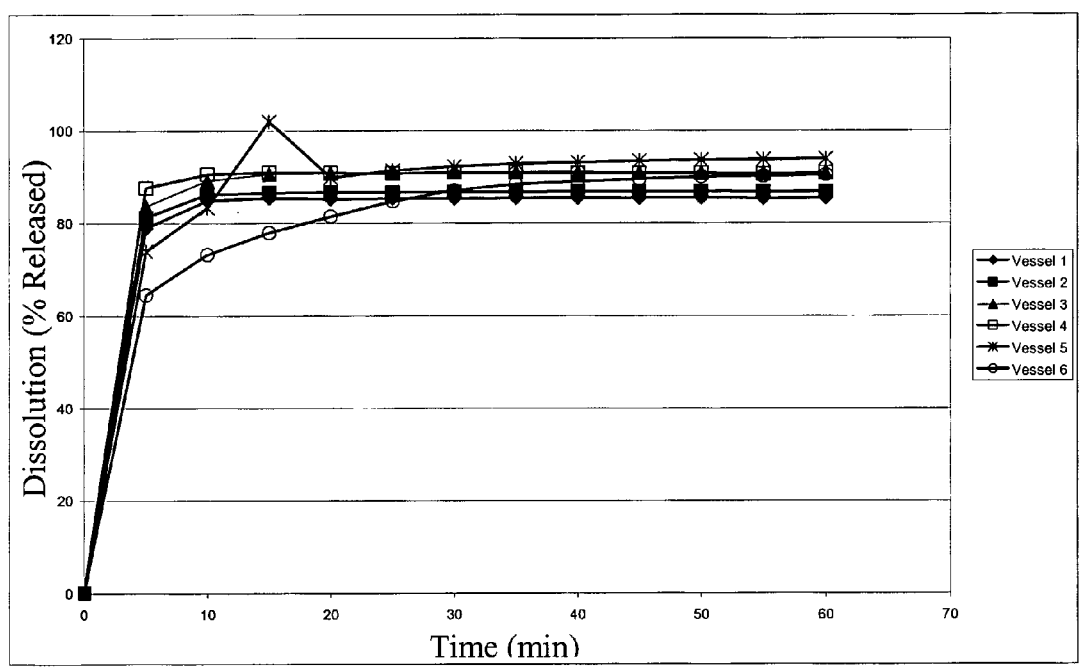

FIG. 9 shows the dissolution of the formulation according to Example 24 resulting in a fast dissolution rate of the paracetamol at different pH values. Similar effect is also obtained with simulated gastric fluid.

Figure 10:
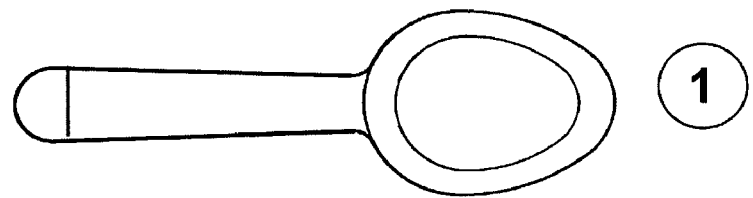
Figure 10:
Figure 10:
Figure 10:
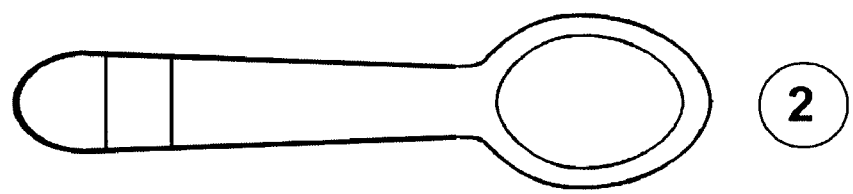
Figure 10:
Figure 10:
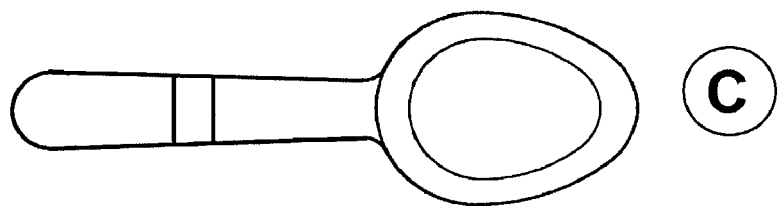
Figure 10:
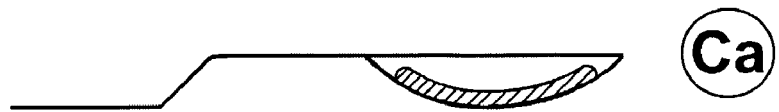

FIG. 10 shows 3 different spoons for use as delivery devices according to the present invention. All spoons are prepared in order to be able to be left on a table or similar place without tilting and at the same time easy to pick up providing an easy handling during administration. The means for preventing the spoons for tilting when left is self-explanatory from the drawings in that either the shaft is bend or more times and or the "floor" of the spoon is flattened. The latter may further be provided with an ordinary concave inner lining of the spoon to avoid material to be left on the spoon after application to the mouth.

MATERIALS AND METHODS

Several of the below Examples have been produced without an active ingredient and used for demonstrating different compositions to which an active can be added (i.e. they are vehicles). Several of these formulations have been used for consumer testing. The term Parvulet as used herein represents any formulation according to the invention and is a trademark for the products.

The following materials have been employed:
Absolute alcohol 99.9%, De danske spritfabrikker, pharmaceutical grade
Aerosil, Unikem, pharmaceutical grade
Caramel flavour, Frutarom
Cefuxime Axetil, Stragen Nordic
Chocolate flavour, Kiranto food
Ferrous fumarate coated, Ferrosan, pharmaceutical grade
Gellan, Kelcogel LT100, CpKelco ApS, pharmaceutical grade
Gellan, Kelcogel F, CpKelco ApS, pharmaceutical grade
Glycerol, Uniqema, pharmaceutical grade
Ibuprofen Coated, Nycomed DK, pharmaceutical grade
Instant sugar, Danisco Oy, pharmaceutical grade
Inulin instant, Fibruline
Ispaghulae Husks, Vi-siblin, Pfizer
Maize Starch Ultrasprese HV, National Starch & Chemical
Medium Chain Triglyceride EP (Labrafac cc), Gattefossé SAS, pharmaceutical grade
PVP (Plastdone® K-25, ISP (Switzerland) AG
Pyridoxine Coated, Ferrosan, pharmaceutical grade
Sodium Citrate, Unikem, pharmaceutical grade
Sodium hydrogen carbonate, Unikem, pharmaceutical grade
Sodium starch glycolate, Explotab, JRS Pharma
Strawberry flavour, Kiranto food
Tutti-frutti flavour, Frutarom
Vanilla flavour, Keranto food A/S
Xanthan gum, Keltrol CpKelco ApS, pharmaceutical grade
Xylitol, Danisco Sweeteners LtD Coat:
    Eudragite EPO, Rohm
    Lauryl sulphate, Sigma
    Altalc 500V, Luzenac America
    Eudragit NE30D, Rohm
Granulation
    Performed by hand mixing until homogenous slightly sticky relative small particles are present Suitable equipment includes High Shear mixer such as in a Zanchetta Roto P100-100 liter capacity or a MTI mixer.
Drop Down Test
    The drop down test apparatus is a medical plastic spoon obtained from Nomeco (DBI Plastic type 115022) with markings for 2½ and 5 ml liquid) see FIG. 1, e.g. drawing E.
Test Method
    In a test spoon 0.5 g-0.7 g test material is accurately weighed. 3 ml-5 ml tapped water is added. Wait ½ min, turn the spoon around, and if the test material does not drop down (fall off the spoon) within 2 min, the material has passed the test.
Viscosity Test
Apparatus:
Brookfield Viscometer Model LVF, Serie 56779
Spindel No. #4 diameter 3.2 mm, length 33.96 mm
Beaker 500 ml low form (approximately 90 mm internal diameter)
Termometer
Parameter:
Speed: 6 rpm
Spindle: The Viscometer spindle is centered in the test sample container. The spindle is properly immersed to the midpoint of the shafts narrow portion.
Test Method
    Into a 500 ml beaker 22-88 g test material is accurately weighed, 500 ml tapped water is added. Mix until all the material is dispersed/dissolved, and after about 5 min the viscosity and the temperature are measured.
Sensory Test
    Tapped water is added to the formulation and when all the liquid is absorbed (visually confirmed), the test can start. Taste the formulation and rank the taste from 1-10, where 10 is the most pleasant taste.

Example 1

A Composition According to the Invention Containing 250 mg Coated Cefuxime Dosage Unit A composition that has a shape as outlined in FIG. 1 containing cefuxime as active substance was prepared as follows:

|  | % w/w | g |
|---|---|---|
| Blend 1: | | |
| Explotab | 46.3[1] | 0.97 |
| Instant sugar | 46.3[2] | 0.97 |
| Aerosil | 0.5[3] | 0.011 |
| Vanilla flavor | 4.6[4] | 0.096 |
| Glycerol | 2.3[5] (binder) | 0.048 |
| Blend 2: | | |
| Blend 1 | 60 | 2.1 |
| Coated Cefuxime | 40 | 1.4 |

The ingredients (1-4) of Blend 1 are mixed ½ min (depending on the amount of powder) in a mortar, transferred to a Philips Food processor, Electronic type HR 2377/D, ingredient 5 is added and mixed for about ½ min (depending on the amount of powder) at speed 4. The ingredients from blend 2 are mixed in a mortar for about ½ min (depending on the amount of powder).

In this example, Explotab is used as a gelling agent that is granulated with glycerol.

The granules are divided into 570 mg/dose. The dose is weight out into a medical spoon and moulded by gently pressing the granules against the spoon with a mortar pistil to a thin layer about 1-3 mm in high in the bottom of the spoon. The water is evaporated at ambient temperature.

Drop Down Test:
    To the above dosage form, 4 ml tapped water is added. After about ½ min the liquid is absorbed. The spoon is turned around and held upside down for 2 min. The test material did not fall out and passed the test.

Example 2

A Composition According to the Invention Containing 250 mg Coated Cefuxime in the Dosage Unit A composition that has a shape as outlined in FIG. 1 containing Cefuxime as active substance, was prepared as follows (given as % w/w):

|  | % w/w | g |
|---|---|---|
| Blend 1: | | |
| Explotab | 46.3[1] | 0.87 |
| Instant sugar | 46.3[2] | 0.87 |
| Aerosil | 0.5[3] | 0.0094 |
| Vanilla flavour | 4.6[4] | 0.086 |
| Glycerol | 2.3[5] | 0.043 |
| Blend 2: | | |
| Blend 1 | 53.6 | 1.87 |
| Coated Cefuxime | 35.7 | 1.25 |
| Vi-siblin | 10.7 | 0.38 |

The ingredients (1-4) of Blend 1 are mixed ½ min (depending on the amount of powder) in a mortar transferred to a Philips Food processor Electronic type HR 2377/D, ingredient 5 is added and mixed for about ½ min (depending on the amount of powder) at speed 4. The ingredients from blend 2 are mixed in a mortar for about ½ min (depending on the amount of powder).

The granules are divided into 700 mg/dose. The dose is weight out into a medical spoon and moulded by gently pressing the granules against the spoon with a mortar pistil to a thin layer about 1-3 mm in high in the bottom of the spoon. The water is evaporated at ambient temperature.

Drop Down Test:
    To the above dosage form 4 ml tapped water is added. After about ½ min the liquid is absorbed. The spoon is turned around and held upside down for 2 min. The test material did not fall out and passed the test.

Example 3

A Composition According to the Invention Containing 250 mg Coated Cefuxime Dosage Unit A composition that has a shape as outlined in FIG. 1 containing cefuxime as active substance was prepared as follows % w/w:

|                | % w/w            | g     |
|----------------|------------------|-------|
| Blend 1:       |                  |       |
| Kelcogel LT100 | 23.1[1]          | 0.52  |
| Xylitol        | 69.1[2]          | 1.55  |
| Aerosil        | 0.5[3]           | 0.011 |
| Vanilla flavour| 5[4]             | 0.112 |
| Glycerol       | 2.3[5]           |       |
| Blend 2:       |                  |       |
| Blend 1        | 64.3             | 2.25  |
| Coated Cefuxime| 35.7             | 1.24  |

The ingredients (1-4) of Blend 1 are mixed ½ min (depending on the amount of powder) in a mortar transferred to a Philips Food processor Electronic type HR 2377/D, ingredient 5 is added and mixed for about ½ min (The granules are made by adding in this case glycerol to the dry mixed powder, i.e. Kelcogel LT100 is pre-swelled in glycerol) at speed 4. The ingredients from blend 2 are mixed in a mortar for about ½ min (depending on the amount of powder).

The granules are divided to 700 mg/dose. The dose is weight out into a medical spoon and moulded by gently pressing the granules against the spoon with a mortar pistil to a thin layer about 1-3 mm in high in the bottom of the spoon. The water is evaporated at ambient temperature.

Drop Down Test:

To the above dosage form 4 ml tapped water is added. After about ½ min the liquid is absorbed. The spoon is turned around and held upside down for 2 min. The test material did not fall out and passed the test.

Example 4

A Composition According to the Invention Containing 150 mg Coated Pyridoxine in the Dosage Unit A composition that has a shape as outlined in FIG. 1 containing coated pyridoxine as active substance was prepared as follows:

|                  | % w/w   | g     |
|------------------|---------|-------|
| Blend 1:         |         |       |
| Kelcogel LT100   | 50[1]   | 0.938 |
| Xylitol          | 47.5[2] | 0.89  |
| Vanilla flavour  | 2.5[3]  | 0.047 |
| Blend 2:         |         |       |
| Blend 1          | 75      | 1.875 |
| Pyridoxine coated| 25      | 0.625 |
| Blend 3:         |         |       |
| Blend 2          | 71.4[1] | 2.50  |
| Kelcogel F       | 14.3[2] | 0.5   |
| Water            | 14.3[3] | 0.5   |

The ingredients (1-3) of Blend 1 are mixed ½ min (depending on the amount of powder) in a mortar. The ingredients from blend 2 are mixed in a mortar for about ½ min (depending on the amount of powder).

The ingredients (2-3 (binding solution) from blend 3 are mixed ½ min and ingredient 1 is added to the blend and mixed for about % min (depending on the amount of powder) and forming the granules.

The granules are divided to 700 mg/dose. The dose is weight out into a medical spoon and moulded by gently pressing the granules against the spoon with a mortar pistil to a thin layer about 1-3 mm in high in the bottom of the spoon. The water is evaporated at ambient temperature.

Drop Down Test:

To the above dosage form 3 ml tapped water is added. After about ½ min the liquid is absorbed. The spoon is turned around and held upside down for 2 min. The test material did not fall out and pass the test.

Example 5

A Composition According to the Invention Containing 150 mg Coated Ferro Fumarate in the Dosage Unit A composition that has a shape as outlined in FIG. 1 containing coated Ferro fumarate as active substance was prepared as follows:

|                | % w/w   | g     |
|----------------|---------|-------|
| Blend 1:       |         |       |
| Kelcogel LT100 | 50[1]   | 0.938 |
| Xylitol        | 47.5[2] | 0.89  |
| Vanilla flavour| 2.5[3]  | 0.047 |
| Blend 2:       |         |       |
| Blend 1        | 75      | 1.875 |
| Ferro fumarate | 25      | 0.625 |
| Blend 3:       |         |       |
| Blend 2        | 71.4[1] | 2.50  |
| Kelcogel F     | 14.3[2] | 0.5   |
| Water          | 14.3[3] | 0.5   |

The ingredients (1-3) of Blend 1 are mixed ½ min (depending on the amount of powder) in a mortar. The ingredients from blend 2 are mixed in a mortar for about ½ min (depending on the amount of powder).

The ingredients (2-3) from blend 3 are mixed ½ min and ingredient 1 is added to the blend and mixed for about ½ min (depending on the amount of powder).

The granules are divided into 700 mg/dose. The dose is weight out into a medical spoon and moulded by gently pressing the granules against the spoon with a mortar pistil to a thin layer about 1-3 mm in high in the bottom of the spoon. The water is evaporated at ambient temperature.

Drop Down Test:

To the above dosage form 3 ml tapped water is added. After about ½ min the liquid is absorbed. The spoon is turned around and held upside down for 2 min. The test material did not fall out and pass the test.

Example 6

A Composition According to the Invention Containing 125 mg Coated Ibuprofen in the Dosage Unit A composition that has a shape as outlined in FIG. 1 containing coated ibuprofen as active substance was prepared as follows:

|  | % w/w | g |
|---|---|---|
| Blend 1: | | |
| Kelcogel LT100 | 52.6[1] | 0.87 |
| Xylitol | 47.4[2] | 0.79 |
| Blend 2: | | |
| Blend 1 | 64.1 | 1.66 |
| Ibuprofen | 20.9 | 0.54 |
| Vanilla flavour | 15 | 0.39 |
| Blend 3: | | |
| Blend 2 | 74.2[1] | 2.59 |
| Kelcogel F | 12.9[2] | 0.45 |
| Water | 12.9[3] | 0.45 |

The ingredients of Blend 1 are mixed ½ min (depending on the amount of powder) in a mortar. The ingredients from blend 2 are mixed in a mortar for about ½ min (depending on the amount of powder).

The ingredients (2-3) from blend 3 are mixed ½ min and ingredient 1 is added to the blend and mixed for about ½ min (depending on the amount of powder).

The granules are divided to 700 mg/dose. The dose is weight out into a medical spoon and moulded by gently pressing the granules against the spoon with a mortar pistil to a thin layer about 1-3 mm in high in the bottom of the spoon. The water is evaporated at ambient temperature, or moulded to a sphere or stripe. The water is evaporated in an oven at 70° C. to constant temperature.

Drop Down Test:

To the above dosage form 3 ml tapped water is added. After about ½ min the liquid is absorbed. The spoon is turned around and held upside down for 2 min. The test material did not fall out and pass the test.

Example 7

A Composition According to the Invention Containing 125 mg Coated Ibuprofen in the Dosage Unit A composition that has a shape as outlined in FIG. 1 containing coated ibuprofen dosage as active substance was prepared as follows:

|  | % w/w | g |
|---|---|---|
| Blend 1: | | |
| Kelcogel LT100 | 52.6[1] | 0.95 |
| Xylitol | 47.4[2] | 0.86 |
| Blend 2: | | |
| Blend 1 | 69.7 | 1.81 |
| Ibuprofen coated | 22.7 | 0.58 |
| Tutti-frutti flavour | 7.6 | 0.20 |
| Blend 3: | | |
| Blend 2 | 74.2[1] | 2.59 |
| Kelcogel F | 12.9[2] | 0.45 |
| Water | 12.9[3] | 0.45 |

The ingredients of Blend 1 are mixed ½ min (depending on the amount of powder) in a mortar. The ingredients from blend 2 are mixed in a mortar for about ½ min (depending on the amount of powder).

The ingredients (2-3) from blend 3 are mixed ½ min and ingredient 1 is added to the blend and mixed for about ½ min (depending on the amount of powder).

The granules are divided into 700 mg/dose. The dose is weight out into a medical spoon and moulded by gently pressing the granules against the spoon with a mortar pistil to a thin layer about 1-3 mm in high in the bottom of the spoon.

Drop Down Test:

To the above dosage form 3 ml tapped water is added. After about ½ min the liquid is absorbed. The spoon is turned around and held upside down for 2 min. The test material did not fall out and pass the test.

Example 8

A Composition According to the Invention Containing 125 mg Coated Ibuprofen in the Dosage Unit A composition that has a shape as outlined in FIG. 1 containing coated ibuprofen as active substance was prepared as follows:

|  | % w/w | g |
|---|---|---|
| Blend 1: | | |
| Kelcogel LT100 | 52.6[1] | |
| Xylitol | 47.4[2] | |
| Blend 2: | | |
| Blend 1 | 71 | 1.83 |
| Ibuprofen coated | 23.2 | 0.6 |
| Caramel flavour | 5.8 | 0.15 |
| Blend 3: | | |
| Blend 2 | 74.2[1] | 2.59 |
| Kelcogel F | 12.9[2] | 0.45 |
| Water | 12.9[3] | 0.45 |

The ingredients of Blend 1 are mixed ½ min (depending on the amount of powder) in a mortar. The ingredients from blend 2 are mixed in a mortar for about ½ min (depending on the amount of powder).

The ingredients (2-3) from blend 3 are mixed ½ min and ingredient 1 is added to the blend and mixed for about ½ min (depending on the amount of powder).

The granules are divided into 700 mg/dose. The dose is weight out into a medical spoon and moulded by gently pressing the granules against the spoon with a mortar pistil to a thin layer about 1-3 mm in high in the bottom of the spoon. The water is evaporated at ambient temperature to a final amount of approximately 575 mg/dose Drop Down Test:

To the above dosage form 3 ml tapped water is added. After about ½ min the liquid is absorbed. The spoon is turned around and held upside down for 2 min. The test material did not fall out and pass the test. The average absorption rate of water by the dosage per second measured in gram water absorb per gram dosage per second is 3 g/0.575 g/30 sec corresponding to a water absorption rate of 0.1739 g/g/s

Example 9

A Composition According to the Invention Containing 125 mg Coated Ferro Fumarate in the Dosage Unit A composition that has a shape as outlined in FIG. 1 containing coated ferro fumarate dosage as active substance was prepared as follows:

|  | % w/w | g |
|---|---|---|
| Blend 1: | | |
| Kelcogel LT100 | 52.6[1] | 0.91 |
| Xylitol | 47.4[2] | 0.83 |
| Blend 2: | | |
| Blend 1 | 67.2 | 1.74 |
| Ferro fumerate coated | 21.9 | 0.56 |
| Chocolate flavour | 10.9 | 0.29 |
| Blend 3: | | |
| Blend 2 | 74.2[1] | 2.59 |
| Kelcogel F | 12.9[2] | 0.45 |
| Water | 12.9[3] | 0.45 |

The ingredients of Blend 1 are mixed ½ min (depending on the amount of powder) in a mortar. The ingredients from blend 2 are mixed in a mortar for about ½ min (depending on the amount of powder).

The ingredients (2-3) from blend 3 are mixed ½ min and ingredient 1 is added to the blend and mixed for about ½ min (depending on the amount of powder).

The granules are divided into 700 mg/dose. The dose is weight out into a medical spoon and moulded By gently pressing the granules against the spoon with a mortar pistil to a thin layer about 1-3 mm in high in the bottom of the spoon. The water is evaporated at ambient temperature to a final amount of approximately 575 mg/dose.

Drop Down Test:

To the above dosage form 3 ml tapped water is added. After about ½ min the liquid is absorbed. The spoon is turned around and held upside down for 2 min. The test material did not fall out and pass the test.

The average absorption rate of water by the dosage per second measured in gram water absorb per gram dosage per second is 3 g/0.575 g/120 sec corresponding to a water absorption rate of 0.0435 g/g/s Example 10

A Placebo Composition According to the Invention

A composition that has a shape as outlined in FIG. 1 was prepared as follows:

|  | % w/w | g |
|---|---|---|
| Blend 1: | | |
| Kelcogel LT100 | 22.5[1] | 0.675 |
| Xylitol | 67.5[2] | 2.025 |
| Ultrasperse HV | 10.0[3] | 0.3 |
| Blend 2: | | |
| Blend 1 | 94.0 | 3.0 |
| Strawberry flavour | 6.0 | 0.2 |
| Blend 3: | | |
| Blend 2 | 91.4[1] | 3.20 |
| Sodium citrate | 1.2[2] | 0.042 |
| Water | 8.4[3] | 0.294 |

The ingredients of Blend 1 are mixed ½ min (depending on the amount of powder) in a mortar. The ingredients from blend 2 are mixed in a mortar for about ½ min (depending on the amount of powder).

The ingredients (2-3) from blend 3 are mixed ½ min and ingredient 1 is added to the blend and mixed for about ½ min (depending on the amount of powder).

The granules are divided into 550 mg/dose. The dose is weight out into a medical spoon and moulded by gently pressing the granules against the spoon with a mortar pistil to a thin layer about 1-3 mm in high in the bottom of the spoon. The water is evaporated at ambient temperature to a final amount of approximately 502 mg/dose.

Drop Down Test:

To the above dosage form 3.5 ml tapped water is added. After about ½ min the liquid is absorbed. The spoon is turned around and held upside down for 2 min. The test material did not fall out and pass the test.

The average absorption rate of water by the dosage per second measured in gram water absorb per gram dosage per second is 3.5 g/0.502 g/120 sec corresponding to a water absorption rate of 0.0581 g/g/s Example 11

A Placebo Composition According to the Invention

A composition that has a shape as outlined in FIG. 1 was prepared as follows:

|  | % w/w | g |
|---|---|---|
| Blend 1: | | |
| Kelcogel LT100 | 25[1] | 0.65 |
| Xylitol | 75[2] | 1.94 |
| Blend 2: | | |
| Blend 1 | 80.3 | 2.59 |
| Inulin | 13.1 | 0.42 |
| Caramel flavour | 6.6 | 0.21 |
| Blend 3: | | |
| Blend 2 | 92 | 3.22 |
| Water | 8 | 0.28 |

The ingredients of Blend 1 are mixed ½ min (depending on the amount of powder) in a mortar. The ingredients from blend 2 are mixed in a mortar for about ½ min (depending on the amount of powder).

Blend 3 is mixed for about ½ min (depending on the amount of powder).

The granules are divided into 550 mg/dose. The dose is weight out into a medical spoon and moulded by gently pressing the granules against the spoon with a mortar pistil to a thin layer about 1-3 mm in high in the bottom of the spoon. The water is evaporated at ambient temperature to a final dosage of 506 mg.

Drop Down Test:

To the above dosage form 3.5 ml tapped water is added. After about ½ min the liquid is absorbed. The spoon is turned around and held upside down for 2 min. The test material did not fall out and pass the test.

The average absorption rate of water by the dosage per second measured in gram water absorb per gram dosage per second is 3.5 g/0.506 g/120 sec corresponding to a water absorption rate of 0.0576 g/g/s Example 12

A Placebo Composition According to the Invention

A composition that has a shape as outlined in FIG. 1 was prepared as follows:

|  | % w/w | g |
|---|---|---|
| Blend 1: | | |
| Kelcogel LT100 | 50[1] | 1.2 |
| Xylitol | 50[2] | 1.2 |
| Blend 2: | | |
| Blend 1 | 80 | 2.4 |
| Keltrol | 20 | 0.6 |
| Blend 3: | | |
| Blend 2 | 71.4[1] | 3.0 |
| Caramel flavour | 14.3[2] | 0.5 |
| Water | 14.3[3] | 0.5 |

The ingredients (1-2) of Blend 1 are mixed ½ min (depending on the amount of powder) in a mortar. The ingredients from blend 2 are mixed in a mortar for about ½ min (depending on the amount of powder).

The ingredients (2-3) from blend 3 are mixed ½ min and ingredient 1 is added to the blend and mixed for about ½ min (depending on the amount of powder).

The granules are divided into 500 mg/dose. The dose is weight out into a medical spoon and moulded by gently pressing the granules against the spoon with a mortar pistil to a thin layer about 1-3 mm in high in the bottom of the spoon. The water is evaporated at ambient temperature to a final dosage of 429 mg Drop Down Test:

To the above dosage form 3 ml tapped water is added. After about ½ min the liquid is absorbed. The spoon is turned around and held upside down for 2 min. The test material did not fall out and pass the test.

Example 13

Figure 1:
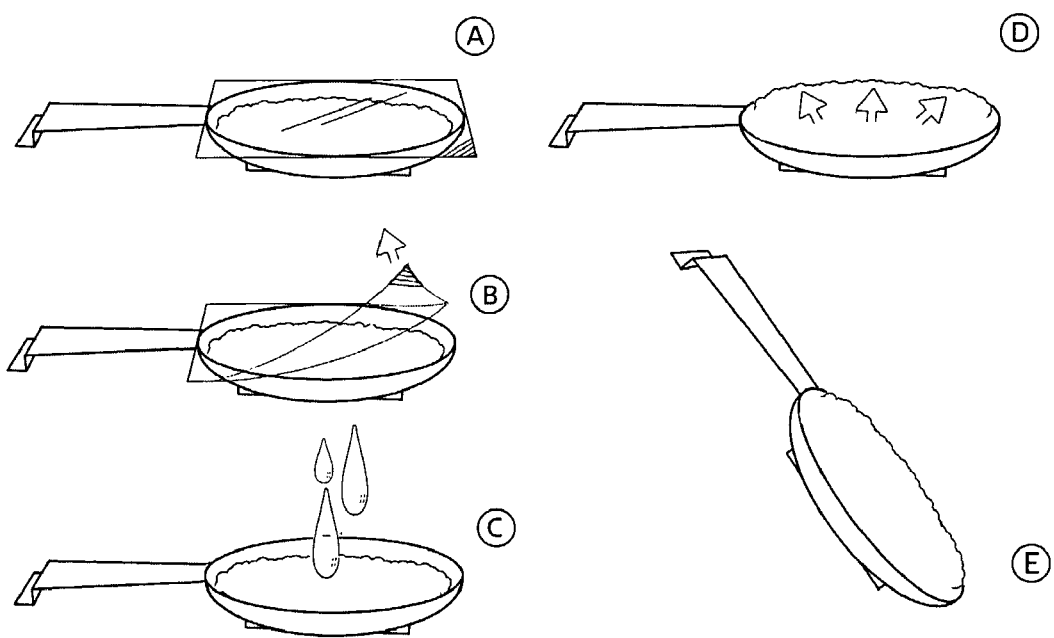
FIG. 1 shows a (A) spoon with the dryg composition adhering to it and covered with a "peel off" film which in (B) is remove and water (C) is added where upon gelling (D) takes place with expansion of the material which do no not slip the spoon (E) when this is tipped the other way round.

A Composition According to the Invention Containing 120 mg Coated Cefuxime in the Dosage Unit A composition in percentage having a shape as outlined in FIG. 1 containing cefuxime as active substance was prepared as follow:

|  | % w/w | g |
|---|---|---|
| Blend 1: | | |
| Sodium citrate | 25[1] | 0.157 |
| Dem. water | 75[2] | 0.470 |
| Blend 2: | | |
| Blend 1 | 98.04[1] | 0.627 |
| Keltrol | 1.96[2] | 0.013 |
| Blend 3: | | |
| Blend 2 | 60 | 0.64 |
| Microencapsulated Cefuxime | 40 | 0.42 |
| Blend 4: | | |
| Kelcogel LT100 | 50[1] | 0.98 |
| Xylitol | 50[2] | 0.98 |
| Blend 5 | | |
| Blend 4 | 56.1 | 1.96 |
| Blend 3 | 30.3 | 1.06 |
| Ketrol | 9.1 | 0.32 |
| Apple fruit | 4.5 | 0.16 |

Blend 1: the ingredient 1 is dissolved in ingredient 2. Blend 2: the ingredient 2 is dissolved in ingredient 1. The ingredient from blend 3 is mixed in a mortar with a scraper or a card until all is blend.

The ingredient from blend 4 is mixed in a mortar with a scraper or a card until all is blend.

The granules are divided to 600 mg/dose. The dose is weight out into a medical spoon and moulded by pressing the granules against the spoon with a stopper to a thin layer about 1-3 mm in high in the bottom of the spoon. The water is evaporated at ambient temperature.

Drop Down Test:

To the above dosage form 4 ml tapped water (temp. between 15-20° C.) is added. After about 15 sec the liquid is absorbed. The spoon is turned around and held upside down for 2 min. The test material did not fall out and pass the test.

Example 14

A Composition According to the Invention Containing 120 mg Coated Cefuxime in the Dosage Unit A composition in percentage having a shape as outlined in FIG. 1 containing cefuxime as active substance was prepared as follow:

|  | % w/w | g |
|---|---|---|
| Blend 1: | | |
| Kelcogel LT100 | 40 | 1.195 |
| Xylitol | 40 | 1.195 |
| Ketrol | 20 | 0.60 |
| Blend 2: | | |
| Sodium citrate | 25[1] | 0.128 |
| Dem. water | 73[3] | 0.372 |
| Keltrol | 2[2] | 0.011 |
| Blend 3 | | |
| Blend 1 | 85.4 | 2.99 |
| Blend 2 | 14.6 | 0.51 |

The ingredients Blend 1 are mixed in a Braun electronic mixer type 4202 for about 1 min. The ingredients (1-2) blend 2 are dissolved in ingredient 3. Blend 3 is mixed to granules in a Braun electronic mixer type 4202 with a dough shaft.

The granules are divided to 600 mg/dose. The dose is weight out into a medical spoon and moulded by pressing the granules against the spoon with a stopper to a thin layer about 1-3 mm in high in the bottom of the spoon. The water is evaporated at ambient temperature.

Drop Down Test:

To the dosage form 4 ml tapped water (temp. between 15-20° C.) is added. After about 15 sec the liquid is absorbed. The spoon is turned around and held upside down for 2 min. The test material did not fall out and pass the test.

Viscosity Test:

Transfer 43.75 g test materials Accurately weighed into a 500 ml beaker, and disperse/dissolve with 500 ml tapped water.

The viscosity is measured to 60500 cps.

Example 15

A Composition According to the Invention Containing 50 mg Coated Paracetamol in the Dosage Unit A composition in percentage having a shape as outlined in FIG. 1 containing paracetamol as active substance was prepared as follow:

| Blend 1: | |
| --- | --- |
| Sodium citrate | 25 |
| Dem. water | 75 |
| Blend 2: | |
| Kelcogel LT100 | 50 |
| Xylitol | 50 |
| Blend 3: | |
| Blend 2 | 75 |
| Keltrol | 12.5 |
| Apple fruit | 12.5 |
| Blend 4: | |
| Blend 3 | 74.22 |
| Blend 1 | 12.13 |
| Microencapsulated paracetamol | 13.65 (61% pure paracetamol) |

Blend 1: Sodium citrate is dissolved in dem. water. Blend 2: The ingredient from blend 2 is mixed in a mortar with a scraper or a card until all is blend. Blend 3: The ingredient from blend 3 is mixed in a mortar with a scraper or a card until all is blend. The ingredient from blend 4 is mixed in a mortar with a scraper or a card until a homogeneous blend is obtained.

The blend 4 is divided to 600 mg/dose. The dose is weight out into a medical spoon and molded by pressing the granules against the spoon with a stopper to a thin layer about 1-3 mm in high in the bottom of the spoon. The water is evaporated at ambient temperature.

Drop Down Test:

To the above dosage form 4 ml tapped water (temp. between 15-20° C.) is added. After about 15 sec the liquid is absorbed. The spoon is turned around and held upside down for 2 min. The test material did not fall out and pass the test.

Example 16

A Composition According to the Invention Containing 50 mg Coated Paracetamol in the Dosage Unit A composition in percentage having a shape as outlined in FIG. 1 containing paracetamol as active substance was prepared as follow:

| Blend 1: | |
| --- | --- |
| Sodium citrate | 25 |
| Dem. water | 75 |
| Blend 2: | |
| Blend 1 | 50 |
| Sodium citrate | 11 |
| PEG 200 | 39 |
| Blend 3: | |
| Kelcogel LT100 | 42.86 |
| Xylitol | 42.86 |
| Keltrol | 14.28 |
| Blend 4: | |
| Blend 2 | 80.50 |
| Blend 3 | 19.50 |
| Blend 5: | |
| Blend 4 | 90.00 |
| Microencapsulated paracetamol | 10.00 (61% pure paracetamol) |

Blend 1: Sodium citrate is dissolved dem. water. Blend 2: The ingredient is mixed.

Blend 3: the ingredient is mixed in a mortar with a scraper or a card until all is blend.

The ingredient from blend 4 is mixed in a mortar with a scraper or a card until all is blend. Blend 5: The ingredient from blend 5 is mixed in a mortar with a scraper or a card until homogeneous blend is obtained.

| Blend 6: | |
| --- | --- |
| PVP (kollidon 25k) | 9.52 |
| Ethanol 99.9% | 85.72 |
| Glycerol | 4.76 |

Blend 6: PVP (kollidon 25k) is dissolved in Ethanol 99.9%, when dissolved Glycerol is added and blend. Blend 6 is poured in a 50 ml spray flask with a nozzle.

Prepared spoon: The concave side of the spoons are sprayed twice with blend 4. The EtOH is evaporated in an oven at 45° C. for one hour.

The blend 5 is divided to 820 mg/dose. The dose is weight out into a prepared medical spoon and moulded by pressing the granules against the spoon with a stopper to a thin layer about 1-3 mm in high in the bottom of the spoon. The water is evaporated at ambient temperature.

Drop Down Test:

To the above dosage form 4 ml tapped water (temp. between 15-20° C.) is added. After about 15 sec the liquid is absorbed. The spoon is turned around and held upside down for 2 min. The test material did not fall out and pass the test.

Example 17

A Composition According to the Invention Containing 200 mg Coated Paracetamol in the Dosage Unit A composition in percentage having a shape as outlined in FIG. 1 containing paracetamol as active substance was prepared as follow:

| Blend 1: | |
| --- | --- |
| Gellan gum (Kelcogel LT100) | 50.00 |
| Xylitol | 50.00 |
| Blend 2: | |
| Blend 1 | 37.5 |
| Microencapsulated paracetamol | 52 (61% pure paracetamol) |
| Glycerin | 10.5 |

Blend 2: The ingredients from blend 1 are mixed in a mortar with a pestle, scraping as needed until homogeneous blend.

| Blend 3: | |
|---|---|
| Povidone (kollidon 25k) | 9.52 |
| Ethanol 99.9% | 85.72 |
| Glycerol | 4.76 |

Blend 3: Povidone (kollidon 25k) is dissolved Ethanol 99.9% and then Glycerol is added and dissolved. Blend 4 is poured in a 50 ml spray flask with nozzle.

Prepared spoon: The concave side of the spoons are sprayed twice with blend 4. The EtOH is evaporated in an oven at 45° C. for one hour.

The blend 2 is divided to 630 mg/dose. The dose is weight out into a prepared medical spoon and moulded by pressing the granules against the spoon with a stopper to a thin layer about 1-3 mm in high in the bottom of the spoon. The water is evaporated at ambient temperature.

Drop Down Test:

To the above dosage form 4 ml tapped water (temp. between 15-20° C.) is added. After about 15 sec the liquid is absorbed. The spoon is turned around and held upside down for 2 min. The test material did not fall out and pass the test.

Dissolution
Material and Methods
Simulated gastric Fluid: For 1 L; 0.1H HCl

Dissolution system consists of online system model SOTAX AT7 and UV detector Model PE lambda 2 using Disslab version 1.1.

The dissolutions curve was obtain with Temp 37° C., Speed 120 rpm, 280 nm and a factor of 108 over a period of 1 h.

Results and Discussion

Figure 2:
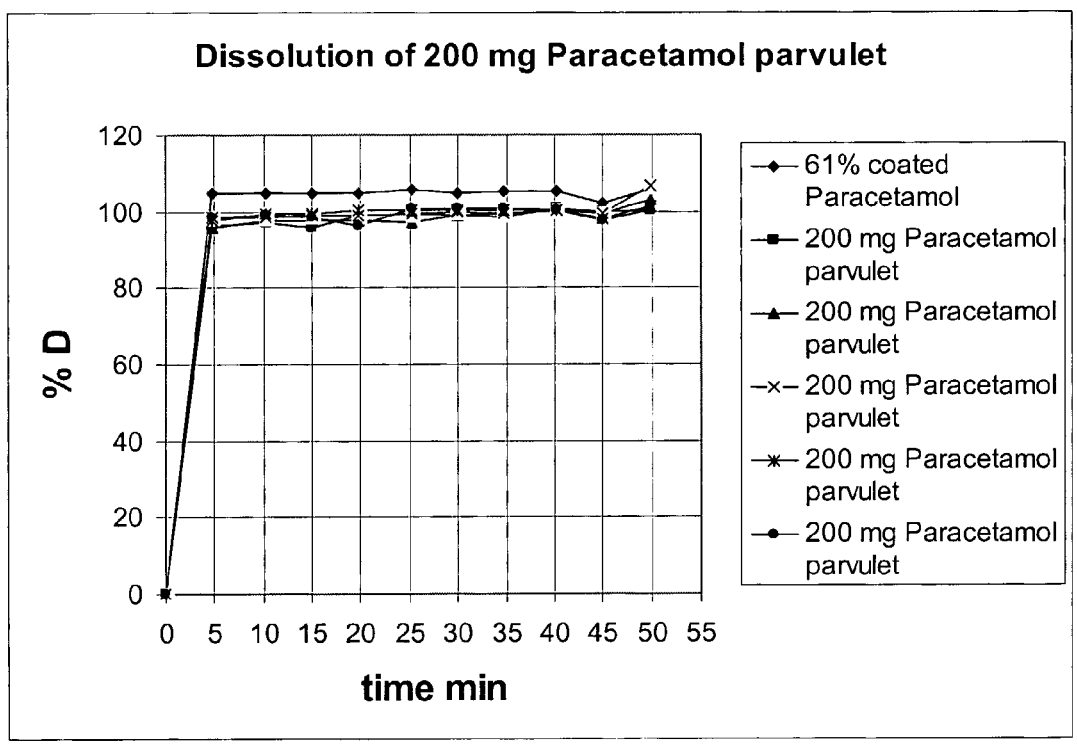
FIG. 2 shows the dissolution curve according to the formulation of Example 17 of a Paracetamol dosage unit in simulated gastric fluid demonstrating a very fast release of at least 96% within 5 minutes.

FIG. 2 illustrates the dissolutions profile of a Paracetamol dosage unit in simulated gastric fluid. After 5 min at least 96% of the Paracetamol is released.

The curve with the dot-line is pure coated paracetamol used in the dosage form; After 5 min at least 96% of the Paracetamol is released.

Comparing pure coated paracetamol and the Paracetamol dosage unit no differences between the release profiles are seen.

Example 18

A Composition According to the Invention Containing 250 mg Coated Paracetamol in the Dosage Unit A composition in percentage having a shape as outlined in FIG. 1 containing paracetamol as active substance was prepared as follow:

| Blend 1: | |
|---|---|
| Sodium citrate | 25 |
| Demineralized water | 75 |
| Blend 2, | |
| Gellan gum (Kelcogel LT100) | 50.00 |
| Xylitol | 50.00 |

| Blend 3: | |
|---|---|
| Blend 1 | 42.7 |
| Blend 2 | 9.8 |
| Microencapsulated paracetamol | 38.7 |
| (61% pure paracetamol) | |
| Sodium Hydrogen Carbonate | 2.9 |
| Strawberry flavour | 5.8 |

Blend 1: Sodium citrate is dissolved Dem. water.
Blend 2: The ingredients from blend are mixed in a mortar with a pestle, scraping as needed until homogeneous blend.
Blend 3: The ingredients from blend are mixed in a mortar with a pestle, scraping as needed until homogeneous blend.

| Blend 4: | |
|---|---|
| Povidone (kollidon 25k) | 9.52 |
| Ethanol 99.9% | 85.72 |
| Glycerol | 4.76 |

Blend 4: Povidone (kollidon 25k) is dissolved Ethanol 99.9% and then Glycerol is added and dissolved. Blend 4 is poured in a 50 ml spray flask with nozzle.

Prepared spoon: The concave side of the spoons are sprayed twice with blend 4. The EtOH is evaporated in an oven at 45° C. for one hour.

The blend 3 is divided to 880 mg/dose. The dose is weight out into a prepared medical spoon and moulded by pressing the granules against the spoon with a stopper to a thin layer about 1-3 mm in high in the bottom of the spoon. The water is evaporated at ambient temperature.

Drop Down Test:

To the above dosage form 4 ml tapped water (temp. between 15-20° C.) is added. After about 15 sec the liquid is absorbed. The spoon is turned around and held upside down for 2 min. The test material did not fall out and pass the test.

Example 19

A Placebo Composition According to the Invention

A composition that has a shape as outlined in FIG. 1 was prepared as follows (given as % w/w):

| Blend 1: | |
|---|---|
| Sodium citrate | 25 |
| Demineralized water | 75 |
| Blend 2: | |
| Kelcogel LT100 | 50 |
| Xylitol | 50 |
| Blend 3: | |
| Blend 1 | 11.2 |
| Blend 2 | 80 |
| Sodium hydrogen carbonates | 3 |
| Strawberry flavor/banana flavor | 5.8 |

Blend 1: Sodium citrate is dissolved dem. Water.
Blend 2: The ingredients from blend are mixed in a mortar with a pestle, scraping as needed until homogeneous blend.
Blend 3: The ingredients from blend are mixed in a mortar with a pestle, scraping as needed until homogeneous blend.

The blend 3 is divided into 250 mg/dose. The dose is weight out into a medical spoon and molded by gently pressing the granules against the spoon with a mortar pistil to a thin layer about 1-3 mm in high in the bottom of the spoon. The water is evaporated at ambient temperature.

Drop Down Test:

To the above dosage form 3 ml tapped water is added. After about ½ min the liquid is absorbed. The spoon is turned around and held upside down for 2 min. The test material did not fall out and pass the test.

In-Vivo Ultra Sound Scanning Test

In vivo properties of the above placebo formulations were determined in a subject who had fasted for 8-12 hours prior to ingesting 250 mL of water and 5 min after having ingested the prepared dosages form. Ultrasound imaging was performed in sitting position throughout the procedure.

B-mode ultrasound imaging of the gastrointestinal tract was done with a LOGIQ (4-10 MHz) linear transducer (Linear 10L H40412LG) coupled to a LOGIQ 9 Ultrasound instrument with software version R3.0.11 abdominal program (8 MHz). Images were videotaped before ingestion of water and immediately prior to ingestion of the dosage form (time 0) and at five minutes intervals thereafter.

Figure 3:
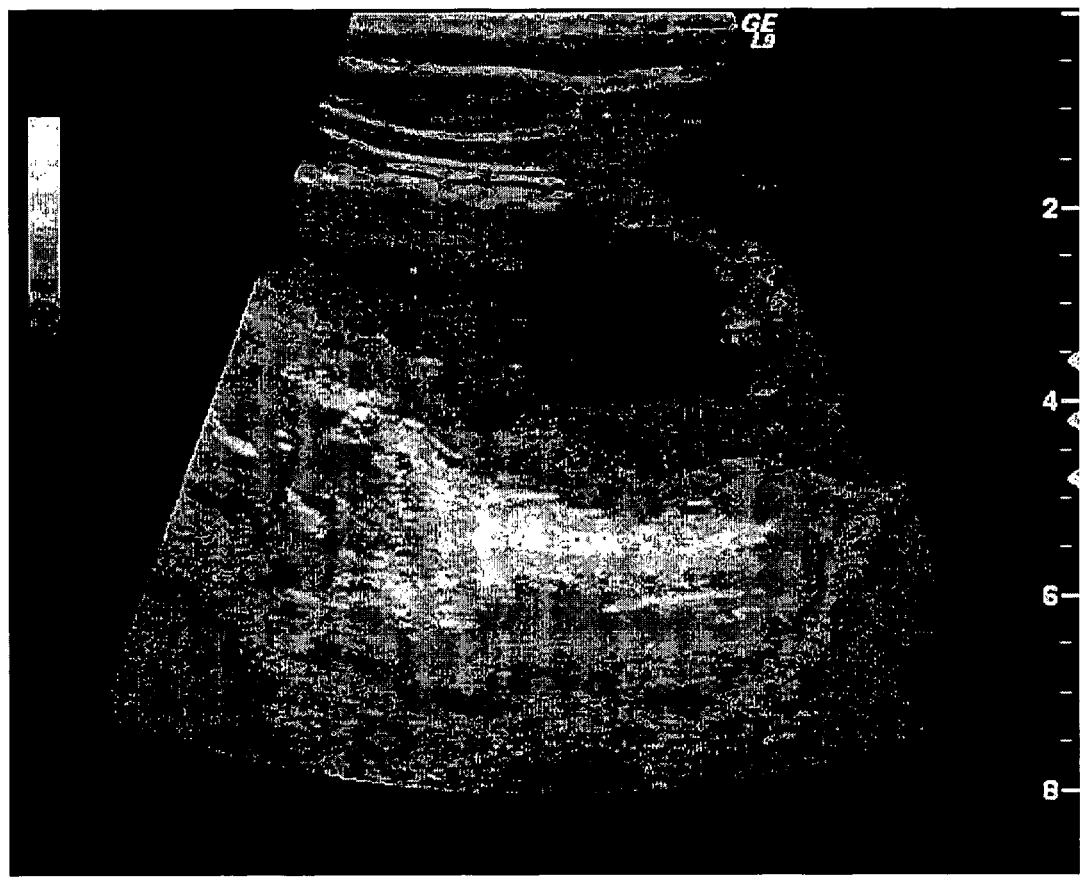
FIG. 3 shows the stomach recorded by in vivo ultrasonic measures after ingestion of water and before ingestion of the formulation according to Example 19.

FIG. 3 demonstrates that the ingested water appeared "black" in the ultrasonic image.

Figure 4:
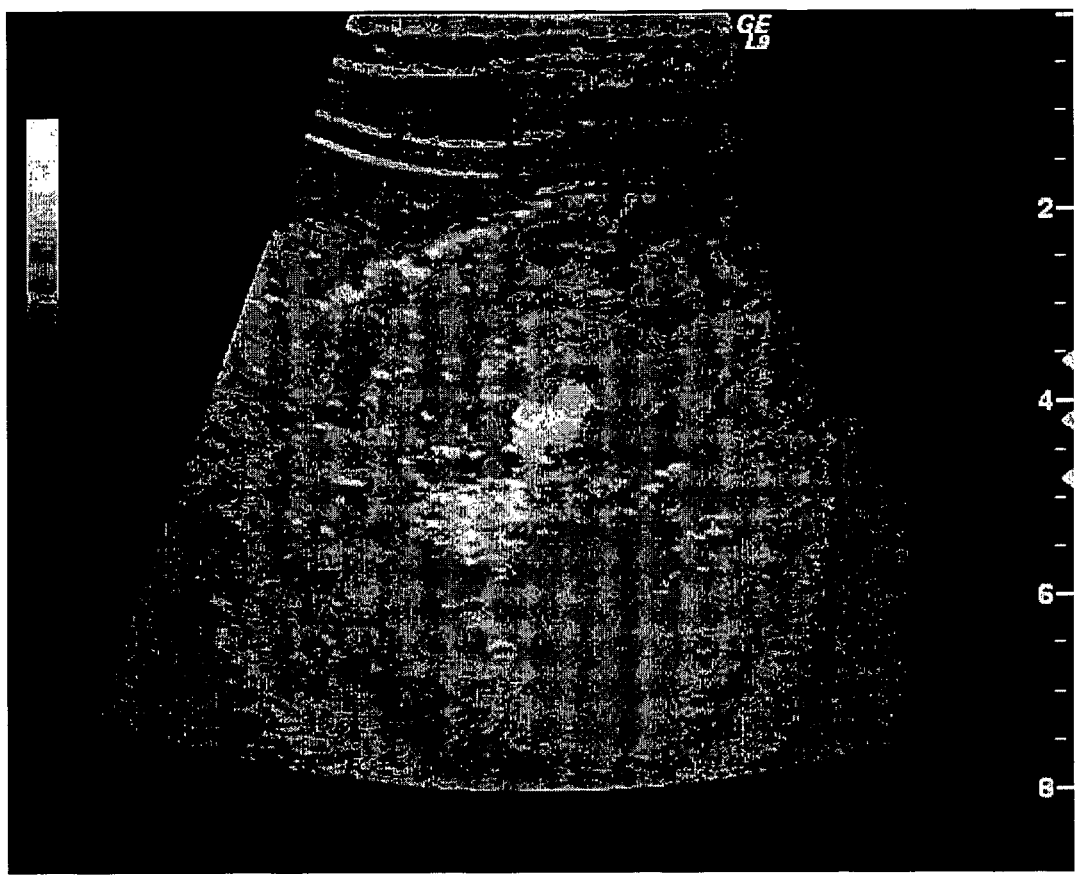
FIG. 4 shows the subsequent ultrasonic pictures just after ingestion of the formulation according to Example 19.

FIG. 4 demonstrates that the ingested dosages form appeared "white" in the ultrasonic image.

Figure 5:
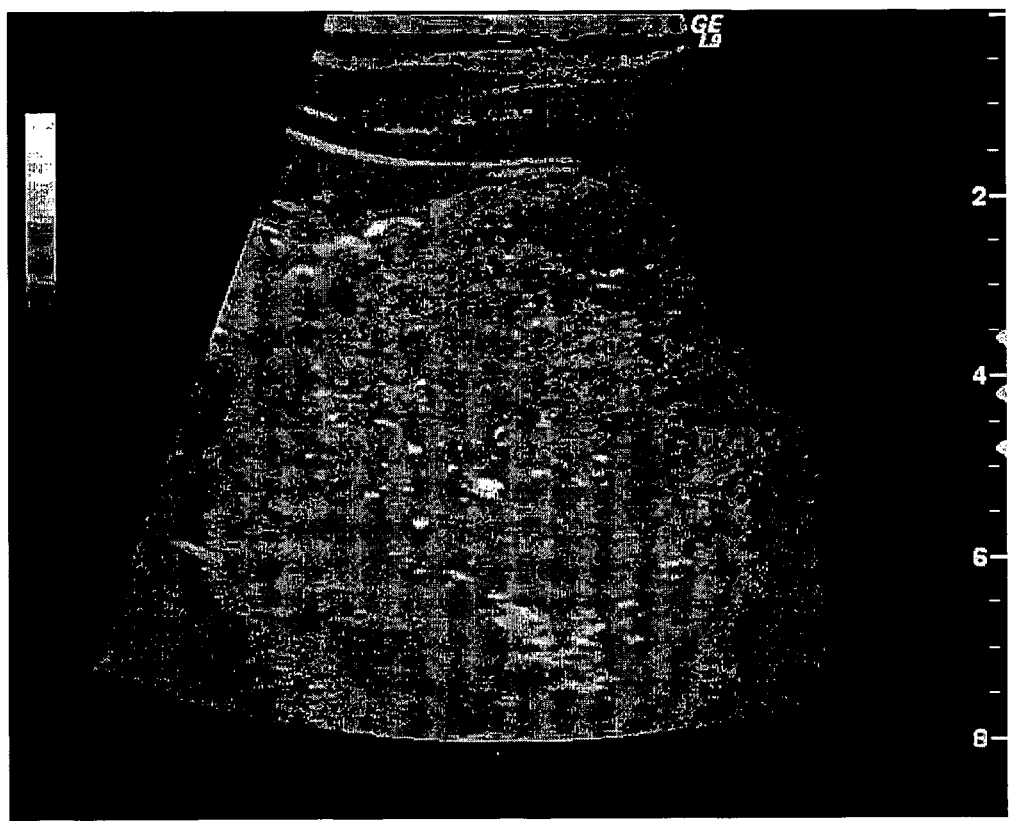
FIG. 5 shows the complete dispersion of the formulation according to Example 19 and as shown in FIG. 4.

Shortly after ingestion of the water the stomach lumen became sonolucent and non-echogenic and thus appeared "black" in the ultrasonic image and after ingestion of the dosage form the stomach lumen became sonolucent and echogenic and thus appeared "white" in the ultrasonic image. As seen from the picture FIG. 5 the dosage form is spread through out the stomach, which indicate that the dosage form is totally disintegrated when reaching the stomach.

Example 20

A Placebo Composition for Use According to the Invention

A composition that has a shape as outlined in FIG. 1 was prepared as follows (given as % w/w):

| Blend 1: | |
| --- | --- |
| Kelcogel LT100 | 50 |
| Xylitol | 50 |
| Blend 2: | |
| Blend 1 | 92.4 |
| Povidone (kollidon 25k) | 0.5 |
| Strawberry flavor/banana/vanilla flavor | 7.1 |
| Blend 3: | |
| Blend 1 | 93.8 |
| Ethanol 99.9% | 6.2 |

Blend 1: Kelcogel LT100 and Xylitol are mixed in a mortar with a pestle, scraping as needed until homogeneous blend.

Blend 2: The ingredients from blend 2 are mixed in a mortar with a pestle, scraping as needed until homogeneous blend.

Blend 3: The ingredients from blend 3 are mixed in a mortar with a pestle, scraping as needed until homogeneous blend.

| Blend 4: | |
| --- | --- |
| Povidone (kollidon 25k) | 9.52 |
| Ethanol 99.9% | 85.72 |
| Glycerol | 4.76 |

Blend 4: Povidone is dissolved in Ethanol and then Glycerol is added and dissolved.

Blend 4 is poured in a 50 ml spray flask with nozzle.

Prepared spoon: The concave side of the spoons are sprayed twice with blend 4. The EtOH is evaporated in an oven at 45° C. for one hour.

The granules are divided to 300 mg/dose. The dose is weight out into a prepared medical spoon and moulded by pressing the granules against the spoon with a stopper to a thin layer about 1-3 mm in high in the bottom of the spoon. The water is evaporated at ambient temperature.

Drop Down Test:

To the above dosage form 3 ml tapped water is added. After about ½ min the liquid is absorbed. The spoon is turned around and held upside down for 2 min. The test material did not fall out and pass the test.

Example 21

A Placebo Composition for Use According to the Invention

A composition that has a shape as outlined in FIG. 1 was prepared as follows (given as % w/w):

| Blend 1: | |
| --- | --- |
| Kelcogel LT100 | 50 |
| Xylitol | 50 |
| Blend 2: | |
| Blend 1 | 83.3 |
| Medium Chain Triglyceride EP (Labrafac cc) | 5.6 |
| Povidone (kollidon 25k) | 5.6 |
| Vanilla flavour | 5.6 |

Blend 1: The ingredients from blend are mixed in a mortar with a pestle, scraping as needed until homogeneous blend.

Blend 2: blend 1 is mixed with Medium Chain Triglyceride EP (Labrafac cc) in a mortar with a pestle, scraping as needed until homogeneous blend and Povidone (kollidon 25k) is added mixed to a homogeneous blend, Vanilla flavour is added to the mixture and blend to a homogeneous mass.

| Blend 3: | |
| --- | --- |
| Povidone (kollidon 25k) | 9.52 |
| Ethanol 99.9% | 85.72 |
| Glycerol | 4.76 |

Blend 3: Povidone (kollidon 25k) is dissolved in Ethanol 99.9% and Glycerol is added to the mixture and dissolved. Blend 4 is poured in a 50 ml spray flask with nozzle.

Prepared spoon: The concave side of the spoons are sprayed twice with blend 3. The EtOH is evaporated in an oven at 45° C. for one hour.

The granules are divided to 250 mg/dose. The dose is weight out into a prepared medical spoon and moulded by pressing the granules against the spoon with a stopper to a thin layer about 1-3 mm in high in the bottom of the spoon. The water is evaporated at ambient temperature.

Drop Down Test:

To the above dosage form 3 ml tapped water is added. After about ½ min the liquid is absorbed. The spoon is turned around and held upside down for 2 min. The test material did not fall out and pass the test.

Example 22

Oral Hygiene Composition for Use Directly in the Mouth Cavity with or without Prehydration A composition in percentage having a shape as outlined in FIG. 1 was prepared as follow:

| Blend 1: | |
|---|---|
| Xylitol | 86.6 |
| Glycerol | 13.4 |
| Blend 2: | |
| Blend 1 | 53.6 |
| Kelcogel LT100 | 46.4 |

Blend 1: Xylitol is mixed with glycerol in a Braun electronic kitchen mixer at level 4, for 2 min. Blend 2: The ingredient from blend 2 is mixed in the Braun Electronic kitchen mixer until all is blend. Sieved through a sieve mesh.

The two blends are mixed and pressed into plates with a thickness of approximately 2 mm and cut into pieces of 1×2 cm. The flakes are dried in an oven (Electrolux) at 45° C. for ½ h.

The flakes are placed in the oral cavity where the formulation will be hydrated by the saliva and any local active released or the formulation can be added conventional toot paste components and dried on tooth brushes or on other devices for mechanical cleaning within the oral cavity.

Example 23

A Placebo Composition According to the Invention

A composition that has a shape as outlined in FIG. 1 was prepared as follows:

| | % w/w | g |
|---|---|---|
| Blend 1 | | |
| Kelcogel LT100 | 50 | 18.78 |
| Xylitol | 50 | 18.78 |
| Blend 2 | | |
| Vanilla Flavour | 92.2 | 2.25 |
| PVP K25 | 7.8 | 0.19 |
| Blend 3 | | |
| Blend 1 | 88.89 | 37.56 |
| Blend 2 | 5.78 | 2.44 |
| Glycerol | 5.33 | 2.25 |

| | % w/w | g |
|---|---|---|
| Blend 4 | | |
| PVP K25 | 9.5 | 4.00 |
| Glycerol | 4.8 | 2.00 |
| Ethanol 99.9% | 85.7 | 36.01 |

Blend 1: Kelcogel LT100 and Xylitol is mixed in a mortar until a homogeneous blend is formed.

Blend 2: The vanilla flavour is grinded in a mortar and the PVP K25 is added stepwise under mixing to form a homogeneous blend.

Blend 3: Blend 1 is volumetrically mixed stepwise into Blend 2 with a dough scraper or mixing card. The Glycerol is added stepwise under continuous slow mixing and a uniform granulate is formed.

Blend 4: Ethanol and PVP K25 is mixed and stirred until a clear mixture is obtained. The Glycerol is added and stirred until a clear mixture is obtained. Blend 4 is poured into a 50 ml spray flask with nozzle.

Medical spoon preparation: The concave side of a medical spoon is sprayed twice with Blend 4 (approximately 60 mg) and placed in an oven at 45° C. for 30 minutes.

335±17.5 mg/dose of Blend 3 is weight into a prepared medicine spoon and distributed by pressing the granules against the spoon with a stopper. The final layer of granules lay in the bottom of the spoon and is approximately 2 mm in height. The spoon is sprayed twice with blend 4 (approximately 60 mg) and placed in an oven at 45° C. for 30 minutes, evaporating the ethanol.

Drop Down Test:

To the above dosage form 5 Ml tapped water is added. After about 30 seconds the liquid is absorbed. The spoon is turned around and held upside down for 2 min. The test material did not fall out and pass the test.

Example 24

A Composition According to the Invention Containing 250 mg Paracetamol

A composition that has a shape as outlined in FIG. 1 was prepared as follows:

| | % w/w | g |
|---|---|---|
| Blend 1: | | |
| Kelcogel LT100 | 50 | 18.78 |
| Xylitol | 50 | 18.78 |
| Blend 2: | | |
| Vanilla Flavour | 92.2 | 2.25 |
| PVP K25 | 7.8 | 0.19 |
| Blend 3: | | |
| Blend 1 | 42.8 | 6.24 |
| Blend 2 | 2.76 | 0.402 |
| Glycerol | 3.42 | 0.499 |
| Paracetamol | 40.6 | 5.92 |
| Glycerol | 10.5 | 1.53 |
| Blend 4: | | |
| PVP K25 | 9.5 | 4.00 |
| Glycerol | 4.8 | 2.00 |
| Ethanol 99.9% | 85.7 | 36.01 |

Blend 1: Kelcogel LT100 and Xylitol is mixed in a mortar until a homogeneous blend is formed.

Blend 2: The vanilla flavour is grinded in a mortar and the PVP K25 is added stepwise under mixing to form a homogeneous blend.

Blend 3: Blend 1 is volumetrically mixed stepwise into Blend 2 with a dough scraper or mixing card. Glycerol is added stepwise under continuous slow mixing and a uniform granulate is formed. Paracetamol is added under continuous slow mixing and the final part of Glycerol is added to form a uniform granulate.

Blend 4: Ethanol and PVP K25 is mixed and stirred until a clear mixture is obtained. The Glycerol is added and stirred until a clear mixture is obtained. Blend 4 is poured into a 50 ml spray flask with nozzle.

Medical spoon preparation: The concave side of a medical spoon is sprayed twice with Blend 4 (approximately 60 mg) and placed in an oven at 45° C. for 30 minutes.

616±20 mg/dose is weight into a prepared medicine spoon and distributed by pressing the granules against the spoon with a stopper. The final layer of granules lay in the bottom of the spoon and is approximately 2 mm in height. topspray Drop Down Test:

To the above dosage form 5 ml tapped water is added. After about 30 seconds the liquid is absorbed. The spoon is turned around and held upside down for 2 min. The test material did not fall out and pass the test.

Example 25

A Composition According to the Invention Containing 415 mg Coated Paracetamol (Corresponding to 250 mg Paracetamol)

A composition that has a shape as outlined in FIG. 1 was prepared as follows:

|  | % w/w | g |
|---|---|---|
| Blend 1: | | |
| Kelcogel LT100 | 50 | 18.78 |
| Xylitol | 50 | 18.78 |
| Blend 2: | | |
| Vanilla Flavour | 92.2 | 2.25 |
| PVP K25 | 7.8 | 0.19 |
| Blend 3: | | |
| Blend 1 | 33.2 | 10.5 |
| Blend 2 | 2.15 | 0.678 |
| Glycerol | 2.66 | 0.840 |
| Coated Paracetamol | 57.1 | 18.06 |
| Glycerol | 4.81 | 1.52 |
| Blend 4: | | |
| PVP K25 | 9.5 | 4.00 |
| Glycerol | 4.8 | 2.00 |
| Ethanol 99.9% | 85.7 | 36.01 |

Blend 1: Kelcogel LT100 and Xylitol is mixed in a mortar until a homogeneous blend is formed.

Blend 2: The vanilla flavour is grinded in a mortar and the PVP K25 is added stepwise under mixing to form a homogeneous blend.

Blend 3: Blend 1 is volumetrically mixed stepwise into Blend 2 with a dough scraper or mixing card. Glycerol is added stepwise under continuous slow mixing and a uniform granulate is formed. Coated Paracetamol is added under continuous slow mixing and the final part of Glycerol is added to form a uniform granulate.

Blend 4: Ethanol and PVP K25 is mixed and stirred until a clear mixture is obtained. The Glycerol is added and stirred until a clear mixture is obtained. Blend 4 is poured into a 50 ml spray flask with nozzle.

Medical spoon preparation: The concave side of a medical spoon is sprayed twice with Blend 4 (approximately 60 mg) and placed in an oven at 45° C. for 30 minutes.

720±20 mg/dose is weight into a prepared medicine spoon and distributed by pressing the granules against the spoon with a stopper. The final layer of granules lay in the bottom of the spoon and is approximately 2 mm in height.

Drop Down Test:

To the above dosage form 5 Ml tapped water is added. After about 30 seconds the liquid is absorbed. The spoon is turned around and held upside down for 2 min. The test material did not fall out and pass the test.

Dissolution Testing:

For dissolution spoons prepared as described above was places in a dissolution medium after removal of the handle and aided by a sinker glued to the outer concave bottom whereby the spoons were located in the bottom of each of the dissolution vessels comprising 900 ml medium and equipped with a paddle rotating at 50 rpm.

Media:

0.1 N HCl ~pH 1 (test media 1): Vessel 5 and 6

Ad 1000 ml of purified water in to a 5000 ml blue cap flask.

Add carefully 25.5 ml 37 w/w % HCl in to the 5000 ml blue cap flask.

Add purified water until 3000 ml is reached.

Measure the pH of the Solution 0.05M Phosphate solution pH 4.5 (test media 2): Vessels 3 and 4

Add 750 ml of a 0.2 M KH2PO4 solution (prepare according to QCF026) in to a 5000 ml blue cap flask.

Add 2250 ml Elix water.

Measure the pH of the solution. The pH changed to 4.8 after addition of sample.

0.05M Phosphate standard solution pH 6.8 (test media 3) Vessel 1 and 2

Dissolution Procedure:

Place 895 g of degassed dissolution medium in vessel 1 to 6.

Vessel 1 and 2: Phosphate buffer pH 6.8.

Vessel 3 and 4: Phosphate solution pH 4.5.

Vessel 5 and 6: 0.1N HCl.

Place 200 ml of Diluent buffer in the Standard vessel.

After cell diagnostics, replace Diluent buffer from the Standard vessel with 250 ml of standard solution (0.2 mg paracetamol/ml).

| Analytical principle | Online UV |
|---|---|
| API | Paracetamol |
| Method | USP 2 (paddle) |
| Degassing | Vacuum filtration at 41° C. |
| Temperature | 37° C. ± 0.5° C. |
| Volume | 900 ± 0.2% (895 ml + 4 ml) |
| Detection | 280 nm |
| Rotation speed | 50 rpm |
| Filters | 0.7µ Full Flow Filter |
| Detection frequency | every 5 min. in 60 minutes |

Sample Preparation:

Carefully remove the shaft from the spoon using a pair of scissors.

Place sinker on outer bottom of the spoon unit.

Add 4 ml of tapped water (room temperature) to the test unit.

Results:

TABLE 1

Release Time and % dissolved material as a function of pH.

| Solution | pH | Release time where less than 0.5% increase from last measurement (Δ<0.5% absolute) | % Dissolved, 60 min. |
|---|---|---|---|
| 0.1 N HCl | 1 | 35 | 93.9 |
|  |  | 50 | 90.4 |
| 0.05 M Phosphate | 4.5 | 15 | 90.8 |
|  |  | 10 | 90.8 |
| 0.05 M Phosphate | 6.8 | 15 | 85.4 |
|  |  | 10 | 86.8 |

CONCLUSIONS

The results demonstrate a fast dissolution rate of the paracetamol from the test product. However, at low pH the release is relatively slower compared to pH 4.5 and 6.8. Note that the gellan gum does not dissolve once gelled hence all dissolution vessels contain a high amount of non-dissolving substances. Besides the pH difference of the media the difference in ionic composition should be noted as this possibly could affect drug release. Furthermore, it is noted that drug release is approx. 91-94% at pH 1 and 4.5 and 85-87% at pH 6.8. As this test was done on n=2 it is not possible to conclude if this is significant and it could be related to the specific coating of the paracetamol.

During dissolution it is seen that the formulation disintegrates in all 3 media as illustrated in the photographs presented in FIGS. 6, 7, and 8 with fine homogeneous material most prominent in buffer solution pH 6.8 (FIG. 8). Slightly bigger, however still homogeneous fluffy flakes of material are seen at pH 4.8 (FIG. 7). At low pH, the formulation still completely disintegrates into more inhomogeneous material with individual flakes varying in size from approximately 1 to 5 mm (FIG. 6).

The dissolution result appears from FIG. 9

A similar result has been obtained with the following media:

Simulated Gastric Fluid, (0.072M cation)-modified SGF USP as without enzymes and with 2.1× cat ions in 6 vessels:

Add 5000 ml of purified water in to a 25 L plastic container.

Add carefully 70 ml 37 w/w % HCl in to the plastic container.

Weigh 42.07 g±0.1 g NaCl and add it to the plastic container.

Dissolve the salt and add purified water until 10000 ml is reached.

Measure the pH of the solution.

Example 26

A Composition According to the Invention Containing 200 mg Coated Ibuprofen

A composition that has a shape as outlined in FIG. 1 was prepared as follows:

|  | % w/w | g |
|---|---|---|
| Blend 1: |  |  |
| Kelcogel LT100 | 50 | 18.72 |
| Xylitol | 50 | 18.76 |
| Blend 2: |  |  |
| Vanilla Flavour | 92.2 | 2.24 |
| PVP K25 | 7.8 | 0.19 |
| Blend 3: |  |  |
| Blend 1 | 50.7 | 5.67 |
| Blend 2 | 3.29 | 0.33 |
| Glycerol | 6.00 | 0.60 |
| Coated Ibuprofen | 40.0 | 4.00 |
| Blend 4: |  |  |
| PVP K25 | 9.5 | 4.00 |
| Glycerol | 4.8 | 2.00 |
| Ethanol 99.9% | 85.7 | 36.01 |

Blend 1: Kelcogel LT100 and Xylitol is mixed in a mortar until a homogeneous blend is formed.

Blend 2: The vanilla flavour is grinded in a mortar and the PVP K25 is added stepwise under mixing to form a homogeneous blend.

Blend 3: Blend 1 is volumetrically mixed stepwise into Blend 2 with a dough scraper or mixing card. Glycerol is added stepwise under continuous slow mixing and a uniform granulate is formed. Ibuprofen is added stepwise under continuous slow mixing.

Blend 4: Ethanol and PVP K25 is mixed and stirred until a clear mixture is obtained. Glycerol is added and stirred until a clear mixture is obtained. Blend 4 is poured into a 50 ml spray flask with nozzle.

Medical spoon preparation: The concave side of a medical spoon is sprayed twice with Blend 4 (approximately 60 mg) and placed in an oven at 45° C. for 30 minutes.

500±20 mg/dose is weight into a prepared medicine spoon and distributed by pressing the granules against the spoon with a stopper. The final layer of granules lay in the bottom of the spoon and is approximately 2 mm in height. The spoon is sprayed twice with blend 4 (approximately 60 mg) and placed in an oven at 45° C. for 30 minutes, evaporating the ethanol.

Drop Down Test:

To the above dosage form 5 Ml tapped water is added. After about 30 seconds the liquid is absorbed. The spoon is turned around and held upside down for 2 min. The test material did not fall out and pass the test.

Example 27

Guideline Regarding Effective Ratio Between Gellan Gum Granulated with Xylitol with Respect to Gelling Time and Amount of Water Necessary for Obtaining an Efficient Gel (300 mg of Mixture)

Xylitol enables water penetration in the granula and secure a fast and efficient hydration of the gum. Binder used is glycerol 7.0% weight of total formulation. Granulating procedure identical with placebo formulation of Example 23. As appears from the Table 2 Xylitol decreases the gelling time and increases the range of water resulting necessary for obtaining a sufficient gelling as the 50%/50% mixture is less sensitive to the amount of water added than the mixture comprising 20% Xylitol. Clearly the less gellan gum present, the less water shall be added to avoid inconvenient presence of excess water in the formulation.

TABLE 2

|  | A | B | C | D | E (blind) |
|---|---|---|---|---|---|
| Gellan Gum % | 100 | 80 | 50 | 20 | 0 |
| Xylitol % | 0 | 20 | 50 | 80 | 100 |
| Water added to spoon(s) | 3, 4, 5 ml | 4 and 5 ml | 4 and 5 ml | 3 ml | 3 ml |
| Gelling quality and time | Insufficient gelling for all 3 spoons as dry granule is still present in the spoons after 30 seconds. | Sufficient gelling with 5 ml only. Gelling time between 10-12 sec. | Sufficient gelling with 4 ml as well as 5 ml water added and completed within 10 seconds. | Good gelling, however excess water present | No gelling |

The invention claimed is:

1. A swellable vehicle for oral administration of one or more active substances, the vehicle comprising 20-80% by weight of a swellable gellan gum, or swellable mixture of gellan gums, arranged in a configuration allowing optimal water diffusion so that upon addition of a predetermined amount of an aqueous medium, without the necessity of applying shear forces or other mixing forces, within a time period of 5 minutes or less swells and/or gels;
wherein the gellan gum is acylated within a degree of up to 4 per every two repeats of the glucose-rhamnose-glucose-glucoronic acid unit of the polymer, and the vehicle further comprises a hydrophilic agent selected from the group consisting of electrolytes, organic acids and osmotic agents, and mixtures thereof, that improves swelling of the gellan gum; and
the texture of the swelled vehicle being similar to that of a soft pudding and having a viscosity of at least about 10,000 cps as measured by a Brookfield Viscometer with a #4 LV spindle at 6 rpm and at 20-25° C.; the Viscometer spindle is centered in the test sample container, the spindle is properly immersed to the mid-point of the shafts narrow portion; test method: Into a 500 ml beaker 22-88 g test material is accurately weighed, 500 ml tapped water is added, mix until all the material is dispersed/dissolved, and after about 5 min the viscosity and the temperature are measured.

2. A vehicle according to claim 1, wherein the viscosity is in a range from about 10,000 to about 99,000 cps.

3. A vehicle according to claim 1 further comprising a swelling and/or gelling agent selected from hydrocolloids and hydrogelling agents, and cellulose derivatives or mixtures thereof.

4. A vehicle according to claim 1, wherein the gellan gum has a mean particle size within 25 mesh to 300 mesh.

5. A vehicle according to claim 1, wherein the gellan gum is acylated within a degree of 0 to 4 per every two repeats of the glucose-rhamnose-glucose-glucoronic acid unit of the polymer.

6. A vehicle according to claim 5, wherein the gellan gum has a degree of acylation of one glycerate per repeat and one acetate per every two repeats.

7. A vehicle according to claim 1, which—when contacted with water—forms a micro-porous hydrogel having a pore size of at the most 4 Å.

8. A vehicle according to claim 1, which—when contacted with water—forms a macro-porous hydrogel having a pore size of from about 4 to about 15 Å.

9. A vehicle according to claim 1, wherein the hydrophilic agent is an osmotic agent selected from the group consisting of hydrophilic vinyl and acryl polymers, poly saccharides, PEO, PEG, PPG, poly(2-hydroxyethyl methacrylate), poly (acrylic)acid, poly(methacrylic)acid, PVP, PVA, PVA/PVP copolymers, HEC, HPC, HPMC, CMC, CEC, sodium alginate, polycarbophil, gelatine and sodium starch glycolate, and mixtures thereof.

10. A vehicle according to claim 9, wherein the hydrophilic agent is an osmotic agent selected from the group consisting of PEO, PEG, PVP, HPMC and polyacrylic acid, and mixtures thereof.

11. A vehicle according to claim 1, wherein the hydrophilic agent is an osmotic agent selected from the group consisting of magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, inulin, instant sugar, citric acid, succinic acid, tartaric acid, and mixtures thereof.

12. A vehicle according to claim 11, wherein the hydrophilic agent is an osmotic agent selected from the group consisting of glucose, lactose, sucrose, mannitol, xylitol and sodium chloride, and mixtures thereof.

13. A vehicle according to claim 1, wherein the hydrophilic agent is an electrolyte is a ionizable substance that is selected from the group consisting of monovalent, divalent, or multivalent ionizable salts.

14. A vehicle according to claim 13, wherein the salt is selected from the group consisting of alkali metal salts, alkaline earth metal salts ionizable alkaline earth metal salts and organic salts.

15. A vehicle according to claim 14, wherein the salt is selected from the group consisting of calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, alkali metal chlorides, sodium fluoride, organic acids, sodium sulfate, dihydrogen sodium phosphate, monohydrogen sodium phosphate, disodium hydrogen phosphate, and mixtures thereof, and multivalent metal cations.

16. A vehicle according to claim 15, wherein the salt is calcium sulfate or sodium chloride.

17. A vehicle according to claim 1, wherein the hydrophilic agent is an organic acid selected from the group consisting of benzoic acid, succinic acid, citric acid and adipic acid and other pharmaceutically approved organic acids.

18. A vehicle according to claim 1 further comprising one or more additives selected from the group consisting of surfactants, coloring agents, sweetening agents, taste-masking agents, antioxidants, polysaccharides, sugars, wetting agents, UV-absorbers, suspending agents, stabilizers, solubilizers, preservatives, processing aids, pH controlling agents, plasticizers, odor masking agents, nutrients, flavouring agents, flavour masking agents, emulsifiers, thickening agents, dispersing agents, crystal grow inhibitors, crystallization promoters, chelating agents, buffers, bases, and antimicrobials, and mixtures thereof.

19. A vehicle according to claim 1 further comprising glycerol.

20. A vehicle according to claim 1 further comprising a pH-adjusting agent.

21. A vehicle according to claim 20, wherein the pH adjusting agent is present in an amount so as to adjust the pH of the gel formed upon addition of an aqueous medium to about 4.5 to about 11.

22. A vehicle according to claim 20, wherein the pH adjusting agent is present in an amount of from about 0.01% to about 15% w/w.

23. A vehicle according to claim 1 comprising a wetting agent selected from the group consisting of pharmaceutically acceptable anionic surfactants, cationic surfactants, amphoteric (amphipathic/amphophilic) surfactants, and non-ionic surfactants; and alkane metal sulfates, wherein the alkyl group is from 1 to 14 carbon atoms.

24. A vehicle according to claim 1 in the form of a powder blend.

25. A vehicle according to claim 1 in the form of granules, beads, oblates or pellets.

26. A vehicle according to claim 1, wherein at least one of the additives selected from the group consisting of surfactants, coloring agents, sweetening agents, taste-masking agents, antioxidants, polysaccharides, sugars, wetting agents, UV-absorbers, suspending agents, stabilizers, solubilizers, preservatives, processing aids, pH controlling agents, plasticizers, odor masking agents, nutrients, flavouring agents, flavour masking agents, emulsifiers, thickening agents, dispersing agents, crystal grow inhibitors, crystallization promoters, chelating agents, buffers, bases, and antimicrobials, and mixtures thereof, and/or the hydrophilic agent and/or the swelling and/or gelling agent is added to a granulate material.

27. A vehicle according to claim 1 in the form of a granulate.

28. A vehicle according to claim 1 further comprising one or more active substances.

29. A vehicle according to claim 28, wherein an active substance is present in admixture with the vehicle.

30. A vehicle according to claim 26, wherein an active substance is present in the granulate material.

31. A vehicle according to claim 28, wherein the active substance is present in a coated and/or microencapsulated form or embedded in a matrix.

32. A vehicle according to claim 28, wherein the active substance is present in a form that allows for controlled release of the active substance.

33. A vehicle according to claim 1, wherein the vehicle passes the drop down test: in a test spoon 0.5 g-0.7 g test material is accurately weighed; 3 ml-5 ml tapped water is added; wait ½ min, turn the spoon around, and if the test material does not drop down (fall off the spoon) within 2 min, the material has passed the test.

34. A swellable pharmaceutical composition for oral administration comprising one or more active substances and a swellable vehicle comprising 20-80% by weight of a swellable gellan gum, or swellable mixture of gellan gums, arranged in a configuration allowing optimal water diffusion so that upon addition of a predetermined amount of an aqueous medium, without the necessity of applying shear forces or other mixing forces, within a time period of 5 minutes or less, the composition swells and/or gels;
wherein the gellan gum is acylated within a degree of up to 4 per every two repeats of the glucose-rhamnose-glucose-glucoronic acid unit of the polymer, and the vehicle further comprises a hydrophilic agent selected from the group consisting of electrolytes, organic acids and osmotic agents, and mixtures thereof, that improves swelling of the gellan gum; and
the texture of the swelled composition being similar to that of a soft pudding and having a viscosity of at least about 10,000 cps as measured by a Brookfield Viscometer with a #4 LV spindle at 6 rpm and at 20-25° C.; the Viscometer spindle is centered in the test sample container, the spindle is properly immersed to the mid-point of the shafts narrow portion; test method: Into a 500 ml beaker 22-88 g test material is accurately weighed, 500 ml tapped water is added, mix until all the material is dispersed/dissolved, and after about 5 min the viscosity and the temperature are measured.

35. A pharmaceutical composition according to claim 34, wherein the viscosity is in a range from about 10,000 to about 99,000 cps.

36. A pharmaceutical composition according to claim 34, further comprising a swelling and/or gelling agent selected from hydrocolloids and hydrogelling agents, and cellulose derivatives, or mixtures thereof.

37. A pharmaceutical composition according to claim 34, wherein the gellan gum has a mean particle size within 25 mesh to 300 mesh.

38. A pharmaceutical composition according to claim 34, wherein the gellan gum is acylated within a degree of 0 to 4 per every two repeats of the glucose-rhamnose-glucose-glucuronic acid unit of the polymer.

39. A pharmaceutical composition according to claim 34, wherein the gellan gum has a degree of acylation of one glycerate per repeat and one acetate per every two repeats.

40. A pharmaceutical composition according to claim 34, which—when contacted with water—forms a micro-porous hydrogel having a pore size of at the most 4 Å.

41. A pharmaceutical composition according to claim 34, which—when contacted with water—forms a macro-porous hydrogel having a pore size of from about 4 to about 15 Å.

42. A pharmaceutical composition according to claim 34, wherein the hydrophilic agent is an osmotic agent selected from the group consisting of hydrophilic vinyl and acryl polymers, poly saccharides, PEO, PEG, PPG, poly(2-hydroxyethyl methacrylate), poly(acrylic)acid, poly(methacrylic)acid, PVP, PVA, PVA/PVP copolymers, HEC, HPC, HPMC, CMC, CEC, sodium alginate, polycarbophil, gelatine and sodium starch glycolate, and mixtures thereof.

43. A pharmaceutical composition according to claim 34, wherein the hydrophilic agent is an osmotic agent selected from the group consisting of PEO, PEG, PVP, HPMC and polyacrylic acid, and mixtures thereof.

44. A pharmaceutical composition according to claim 34, wherein the hydrophilic agent is an osmotic agent selected from the group consisting of magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, inulin, instant sugar, citric acid, succinic acid, tartaric acid, and mixtures thereof.

45. A pharmaceutical composition according to claim 34, wherein the hydrophilic agent is an osmotic agent selected from the group consisting of glucose, lactose, sucrose, mannitol, xylitol and sodium chloride, and mixtures thereof.

46. A pharmaceutical composition according to claim 34, wherein the hydrophilic agent is an electrolyte is a ionizable substance that is selected from the group consisting of monovalent, divalent, or multivalent ionizable salts.

47. A pharmaceutical composition according to claim 46, wherein the salt is selected from the group consisting of alkali metal salts, alkaline earth metal salts, ionizable alkaline earth metal salts and organic salts.

48. A pharmaceutical composition according to claim 47, wherein the salt is selected from the group consisting of calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, alkali metal chlorides, sodium fluoride, organic acids, sodium sulfate, dihydrogen sodium phosphate, monohydrogen sodium phosphate, disodium hydrogen phosphate, and mixtures thereof, and multivalent metal cations.

49. A pharmaceutical composition according to claim 48, wherein the salt is calcium sulfate or sodium chloride.

50. A pharmaceutical composition according to claim 34, wherein the hydrophilic agent is an organic acid selected from the group consisting of benzoic acid, succinic acid, citric acid and adipic acid and other pharmaceutically approved organic acids.

51. A pharmaceutical composition according to claim 34, further comprising one or more additives selected from the group consisting of surfactants, coloring agents, sweetening agents, taste-masking agents, antioxidants, polysaccharides, sugars, wetting agents, UV-absorbers, suspending agents, stabilizers, solubilizers, preservatives, processing aids, pH controlling agents, plasticizers, odor masking agents, nutrients, flavouring agents, flavour masking agents, emulsifiers, thickening agents, dispersing agents, crystal grow inhibitors, crystallization promoters, chelating agents, buffers, bases, and antimicrobials, and mixtures thereof.

52. A pharmaceutical composition according to claim 34, further comprising glycerol.

53. A pharmaceutical composition according to claim 34, further comprising a pH-adjusting agent.

54. A pharmaceutical composition according to claim 53, wherein the pH adjusting agent is present in an amount so as to adjust the pH of the gel formed upon addition of an aqueous medium to about 4.5 to about 11.

55. A pharmaceutical composition according to claim 53, wherein the pH adjusting agent is present in an amount of from about 0.01% to about 15% w/w.

56. A pharmaceutical composition according to claim 34, comprising a wetting agent selected from the group consisting of pharmaceutically acceptable anionic surfactants, cationic surfactants, amphoteric (amphipathic/amphophilic) surfactants, and non-ionic surfactants and alkane metal sulfates, wherein the alkyl group is from 1 to 14 carbon atoms.

57. A pharmaceutical composition according to claim 34, in the form of a powder blend.

58. A pharmaceutical composition according to claim 34, wherein at least one of the additives selected from the group consisting of surfactants, coloring agents, sweetening agents, taste-masking agents, antioxidants, polysaccharides, sugars, wetting agents, UV-absorbers, suspending agents, stabilizers, solubilizers, preservatives, processing aids, pH controlling agents, plasticizers, odor masking agents, nutrients, flavouring agents, flavour masking agents, emulsifiers, thickening agents, dispersing agents, crystal grow inhibitors, crystallization promoters, chelating agents, buffers, bases, and antimicrobials, and mixtures thereof, and/or the hydrophilic agent and/or the swelling and/or gelling agent is added to a granulate material.

59. A pharmaceutical composition according to claim 34, wherein the active substance is present in a coated and/or microencapsulated form or embedded in a matrix.

60. A pharmaceutical composition according to claim 34, wherein the active substance is present in a form that allows for controlled release of the active substance.

61. A pharmaceutical composition according to claim 34, wherein the active substance is in admixture with the vehicle.

62. A pharmaceutical composition according to claim 34, wherein the active substance and the vehicle is in the form of granules, beads, oblates or pellets.

63. A pharmaceutical composition according to claim 34, wherein the active substance and the vehicle is in the form of a granulate.

64. A pharmaceutical composition according to claim 34, which passes the drop down test: in a test spoon 0.5 g-0.7 g test material is accurately weighed; 3 ml-5 ml tapped water is added; wait ½ min, turn the spoon around, and if the test material does not drop down (fall off the spoon) within 2 min, the material has passed the test.

65. A pharmaceutical composition according to claim 34, in the form of a solid dosage form.

66. A pharmaceutical composition according to claim 65 in the form of a unit dosage form.

67. A pharmaceutical composition according to claim 65 in the form of a dosage kit comprising a dispensing unit incorporating the solid dosage form.

68. A pharmaceutical composition according to claim 67, wherein the dispensing unit is a spoon.

69. A dispensing unit comprising a swellable pharmaceutical composition for oral administration comprising one or more active substances and a swellable vehicle comprising 20-80% by weight of a swellable gellan gum, or swellable mixture of gellan gums, arranged in a configuration allowing optimal water diffusion so that upon addition of a predetermined amount of an aqueous medium, without the necessity of applying shear forces or other mixing forces, within a time period of 5 minutes or less, the composition swells and/or gels;
    wherein the gellan gum is acylated within a degree of up to 4 per every two repeats of the glucose-rhamnose-glucose-glucoronic acid unit of the polymer, and the vehicle further comprises a hydrophilic agent selected from the group consisting of electrolytes, organic acids and osmotic agents, and mixtures thereof, that improves swelling of the gellan gum; and
    the texture of the swelled composition being similar to that of a soft pudding and having a viscosity of at least about 10,000 cps as measured by a Brookfield Viscometer with a #4 LV spindle at 6 rpm and at 20-25° C.; the Viscometer spindle is centered in the test sample container, the spindle is properly immersed to the mid-point of the shafts narrow portion; test method: Into a 500 ml beaker 22-88 g test material is accurately weighed, 500 ml tapped water is added, mix until all the material is dispersed/dissolved, and after about 5 min the viscosity and the temperature are measured.

70. A dispensing unit according to claim 69 in unit dosage form.

71. A dispensing unit according to claim 69, wherein the pharmaceutical composition is adhered or glued to a surface of the dispensing unit.

72. A dispensing unit according to claim 69 having a concave surface.

73. A dispensing unit according to claim 69 in the form of a spoon.

74. A dispensing unit according to claim 73 in which the pharmaceutical composition is adhered or glued to the concave part of the spoon.

75. A dispensing unit according to any of claim 71 or 74, wherein the glue comprises one or more components in liquid form or in solution selected from the group consisting of sugar alcohols, sugars, polyvinylpyrrolidone (PVP), gums.

76. A dispensing unit according to any of claim 71 or 74, wherein the glue comprises a mixture of PVP and glycerol.

77. A method for preparing a pharmaceutical composition according to claim 34, the method comprising blending the dry components and optionally granulating the mixture with a binder.

78. A method according to claim 77, wherein the pharmaceutical composition further comprises one or more excipients and/or active ingredients which have an aqueous solubility substantially lower than the aqueous solubility of the gellan gum.

79. A method according to claim 78 comprising
(i) granulating a first blend comprising swellable gellan gum but essentially not containing the one or more excipients and/or active ingredients which have an aqueous solubility substantially lower than the aqueous solubility of the gellan gum,
(ii) adding the one or more excipients and/or active ingredients which have an aqueous solubility substantially lower than the aqueous solubility of the gellan gum to the granulated first blend.

80. A method according to claim 79 wherein the one or more excipients and/or active ingredients which have an aqueous solubility substantially lower than the aqueous solubility of the gellan gum is added to the granulated first blend as a blend or granulate with additional excipients.

81. A vehicle according to claim 3, wherein the swelling and/or gelling agent is selected from the group consisting of alginic acid, sodium alginate, potassium alginate, ammonium alginate, calcium alginate, propane-1,2-diol alginate, agar, carrageenan, processed eucheuma seaweed, locust bean gum, guar gum, tragacanth, acacia gum, xanthan gum, karaya gum, tara gum, konjac, pectins, methyl cellulose, hydroxypropyl cellulose, hydroxypropyl methyl cellulose, ethyl methyl cellulose, carboxy methyl cellulose, sodium carboxy methyl cellulose, crosslinked sodium carboxy methyl cellulose, enzymatically hydrolysed carboxy methyl cellulose, gelatin, and mixtures thereof.

82. A vehicle according to claim 15, wherein the salt is a salt of an organic acid selected from the group consisting of citric, succinic, fumaric, malic, maleic, glutaric, and lactic acid.

83. A vehicle according to claim 20, wherein the pH-adjusting agent is selected from the group consisting of sodium bicarbonate, sodium phosphate, sodium hydroxide, ammonium hydroxide, sodium stannate, triethanolamine, citric acid, hydrochloric acid, sodium citrate, and combinations thereof.

84. A vehicle according to claim 21, wherein the pH adjusting agent is present in an amount so as to adjust the pH of the gel formed upon addition of an aqueous medium to about 5 to about 9.

85. A vehicle according to claim 21, wherein the pH adjusting agent is present in an amount so as to adjust the pH of the gel formed upon addition of an aqueous medium to about 5 to about 8.

86. A vehicle according to claim 22, wherein the pH adjusting agent is present in an amount of from about 0.05% to about 5% w/w.

87. A vehicle according to claim 23, wherein the wetting agent selected from the group consisting of poloxamer, PEG, PEO, sodium methyl sulfate, sodium lauryl sulfate and dioctyl sodium sulfosuccinate.

88. A pharmaceutical composition according to claim 36, wherein the hydrogelling agent is selected from the group consisting of alginic acid, sodium alginate, potassium alginate, ammonium alginate, calcium alginate, propane-1,2-diol alginate, agar, carrageenan, processed eucheuma seaweed, locust bean gum, guar gum, tragacanth, acacia gum, xanthan gum, karaya gum, tara gum, konjac, pectins, methyl cellulose, hydroxypropyl cellulose, hydroxypropyl methyl cellulose, ethyl methyl cellulose, carboxy methyl cellulose, sodium carboxy methyl cellulose, crosslinked sodium carboxy methyl cellulose, enzymatically hydrolysed carboxy methyl cellulose, gelatin, and mixtures thereof.

89. A pharmaceutical composition according to claim 47, wherein the salt is a salt of an organic acid selected from the group consisting of citric, succinic, fumaric, malic, maleic, glutaric, and lactic acid.

90. A pharmaceutical composition according to claim 53, wherein the pH-adjusting agent is selected from the group consisting of sodium bicarbonate, sodium phosphate, sodium hydroxide, ammonium hydroxide, sodium stannate, triethanolamine, citric acid, hydrochloric acid, sodium citrate, and combinations thereof.

91. A pharmaceutical composition according to claim 54, wherein the pH adjusting agent is present in an amount so as to adjust the pH of the gel formed upon addition of an aqueous medium to about 5 to about 9.

92. A pharmaceutical composition according to claim 54, wherein the pH adjusting agent is present in an amount so as to adjust the pH of the gel formed upon addition of an aqueous medium to about 5 to about 8.

93. A pharmaceutical composition according to claim 55, wherein the pH adjusting agent is present in an amount of from about 0.05% to about 5% w/w.

94. A pharmaceutical composition according to claim 56, wherein the wetting agent is selected from the group consisting of poloxamer, PEG, PEO, sodium methyl sulfate, sodium lauryl sulfate and dioctyl sodium sulfosuccinate.

95. A vehicle according to claim 1, comprising at least 22.5% by weight of the swellable gellan gum, or swellable mixture of gellan gums.

96. A vehicle according to claim 1, comprising from 22.5% to about 53% by weight of the swellable gellan gum, or swellable mixture of gellan gums.

97. A vehicle according to claim 1, wherein the swellable gellan gum, or swellable mixture of gellan gums is in an amount by weight selected from the group consisting of 22.5%, 23.1%, 25%, 40%, 42.86%, 46.4%, 50%, and 52.6%.

98. A pharmaceutical composition according to claim 34, wherein the swellable vehicle comprises at least 22.5% by weight of the swellable gellan gum, or swellable mixture of gellan gums.

99. A pharmaceutical composition according to claim 34, wherein the swellable vehicle comprises from 22.5% to about 53% by weight of the swellable gellan gum, or swellable mixture of gellan gums.

100. A pharmaceutical composition according to claim 34, wherein the swellable vehicle comprises the swellable gellan gum, or swellable mixture of gellan gums in an amount by weight selected from the group consisting of 22.5%, 23.1%, 25%, 40%, 42.86%, 46.4%, 50%, and 52.6%.

101. A pharmaceutical composition according to claim 34, wherein the composition comprises at least about 15% by weight of the swellable gellan gum, or swellable mixture of gellan gums.

102. A pharmaceutical composition according to claim 34, wherein the composition comprises from about 15% to about 46% by weight of the swellable gellan gum, or swellable mixture of gellan gums.

103. A pharmaceutical composition according to claim 34, wherein the composition comprises the swellable gellan gum, or swellable mixture of gellan gums in an amount by weight selected from the group consisting of about 15%, about 17%, about 18%, about 19%, about 20%, about 21%, about 25%, about 26%, about 27% about 28%, about 34%, about 40%, about 42%, about 44%, and about 46%.

104. A dispensing unit according to claim 69, wherein the swellable vehicle comprises at least 22.5% by weight of the swellable gellan gum, or swellable mixture of gellan gums.

105. A dispensing unit according to claim 69, wherein the swellable vehicle comprises from 22.5% to about 53% by weight of the swellable gellan gum, or swellable mixture of gellan gums.

106. A dispensing unit according to claim 69, wherein the swellable vehicle comprises the swellable gellan gum, or swellable mixture of gellan gums in an amount by weight selected from the group consisting of 22.5%, 23.1%, 25%, 40%, 42.86%, 46.4%, 50%, and 52.6%.

* * * * *

UNITED STATES PATENT AND TRADEMARK OFFICE
CERTIFICATE OF CORRECTION

PATENT NO. : 8,383,154 B2  
APPLICATION NO. : 11/596123  
DATED : February 26, 2013  
INVENTOR(S) : Daniel Bar-Shalom et al.

Page 1 of 1

It is certified that error appears in the above-identified patent and that said Letters Patent is hereby corrected as shown below:

On the title page item (73) change: "EGALET A/S" to: -- EGALET LTD. --.

Signed and Sealed this  
Seventeenth Day of September, 2013

Teresa Stanek Rea  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,383,154 B2 | Page 1 of 1 |
| APPLICATION NO. | : 11/596123 | |
| DATED | : February 26, 2013 | |
| INVENTOR(S) | : Bar-Shalom et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1658 days.

Signed and Sealed this
Eleventh Day of November, 2014

Michelle K. Lee
*Deputy Director of the United States Patent and Trademark Office*